US008580263B2

(12) United States Patent  
Adams et al.

(10) Patent No.: US 8,580,263 B2
(45) Date of Patent: Nov. 12, 2013

(54) ANTI-EGFR FAMILY ANTIBODIES, BISPECIFIC ANTI-EGFR FAMILY ANTIBODIES AND METHODS OF USE THEREOF

(75) Inventors: Gregory P. Adams, Hatboro, PA (US); Eva M. Horak, West Oragne, NJ (US); Louis M. Weiner, Washington, DC (US); James D. Marks, Kensington, CA (US)

(73) Assignees: The Regents of the University of California, Oakland, CA (US); Fox Chase Cancer Center, Philadelphia, PA (US)

( * ) Notice: Subject to any disclaimer, the term of this patent is extended or adjusted under 35 U.S.C. 154(b) by 795 days.

(21) Appl. No.: 12/515,522

(22) PCT Filed: Nov. 20, 2007

(86) PCT No.: PCT/US2007/024287
§ 371 (c)(1),
(2), (4) Date: Apr. 1, 2010

(87) PCT Pub. No.: WO2008/140493
PCT Pub. Date: Nov. 20, 2008

(65) Prior Publication Data
US 2010/0196265 A1 Aug. 5, 2010

Related U.S. Application Data

(60) Provisional application No. 60/860,750, filed on Nov. 21, 2006, provisional application No. 60/867,015, filed on Nov. 22, 2006.

(51) Int. Cl.
*A61K 38/00* (2006.01)

(52) U.S. Cl.
USPC .................. 424/143.1; 424/136.1; 424/155.1; 530/387.1; 530/387.7; 530/388.22

(58) Field of Classification Search
None
See application file for complete search history.

(56) References Cited

U.S. PATENT DOCUMENTS

| | | | |
|---|---|---|---|
| 4,444,878 A | 4/1984 | Paulus | |
| 4,801,575 A | 1/1989 | Pardridge | |
| 4,902,505 A | 2/1990 | Pardridge et al. | |
| 5,292,668 A | 3/1994 | Paulus | |
| 5,523,210 A | 6/1996 | Paulus | |
| 5,601,819 A | 2/1997 | Wong et al. | |
| 5,932,448 A | 8/1999 | Tso et al. | |
| 5,959,084 A | 9/1999 | Ring et al. | |
| 5,977,322 A | 11/1999 | Marks et al. | |
| 5,985,276 A | 11/1999 | Lindhofer et al. | |
| 5,990,275 A | 11/1999 | Whitlow et al. | |
| 6,010,902 A | 1/2000 | Ledbetter et al. | |
| 6,060,285 A | 5/2000 | Lenz et al. | |
| 6,106,833 A | 8/2000 | Ring et al. | |
| 6,129,914 A | 10/2000 | Weiner et al. | |
| 6,210,668 B1 | 4/2001 | Lindhofer et al. | |
| 6,245,523 B1 | 6/2001 | Altieri | |
| 6,287,792 B1 | 9/2001 | Pardridge et al. | |
| 6,451,980 B1 | 9/2002 | Khaw et al. | |
| 6,458,933 B1 | 10/2002 | Hansen | |
| 6,512,097 B1 | 1/2003 | Marks et al. | |
| 6,723,538 B2 | 4/2004 | Mack et al. | |
| 6,794,128 B2 | 9/2004 | Marks et al. | |
| 7,332,580 B2 | 2/2008 | Adams et al. | |
| 7,332,585 B2 | 2/2008 | Adams et al. | |
| 8,329,873 B2 | 12/2012 | Adams et al. | |
| 2001/0036459 A1 | 11/2001 | Ravetch | |
| 2002/0132990 A1 | 9/2002 | Huston et al. | |
| 2004/0071696 A1* | 4/2004 | Adams et al. | 424/143.1 |
| 2004/0071896 A1 | 4/2004 | Kang et al. | |
| 2006/0099205 A1 | 5/2006 | Adams et al. | |
| 2011/0059076 A1* | 3/2011 | McDonagh et al. | 424/133.1 |
| 2012/0003221 A1* | 1/2012 | McDonagh et al. | 424/134.1 |

FOREIGN PATENT DOCUMENTS

| | | |
|---|---|---|
| EP | 0 592 564 | 9/1996 |
| EP | 1 187 634 B1 | 12/2007 |
| EP | 1 889 631 A1 | 2/2008 |
| WO | WO00/78347 | 12/2000 |
| WO | WO02/00914 | 1/2002 |
| WO | WO2004/032961 | 4/2004 |
| WO | WO2006/091209 | 8/2006 |
| WO | WO2007/084181 | 7/2007 |
| WO | WO2008/140493 | 11/2008 |

OTHER PUBLICATIONS

Perez-Soler (The Oncologist, 2004, 9:58-67.*
U.S. Appl. No. 13/710,146, filed Dec. 10, 2012, Adams et al.
US Office Action dated Mar. 14, 2007 issued in U.S. Appl. No. 10/406,830.
US Notice of Allowance dated Aug. 7, 2007 issued in U.S. Appl. No. 10/406,830.
US Notice of Allowance dated Sep. 17, 2007 issued in U.S. Appl. No. 11/154,103.
US Notice of Allowance dated Mar. 31, 2010 issued in U.S. Appl. No. 11/943,367.
US Notice of Allowance dated Aug. 16, 2010 issued in U.S. Appl. No. 11/943,367.
US Notice of Allowance dated Oct. 2, 2012 issued in U.S. Appl. No. 11/943,367.
US Supplemental Examiner's Amendment dated Nov. 5, 2012 issued in U.S. Appl. No. 11/943,367.
PCT International Search Report dated Jun. 17, 2008 issued in PCT/US2006/023479 (WO 2007/084181).
PCT International Preliminary Report on Patentability and Written Opinion dated Jul. 22, 2008 issued in PCT/US2006/023479 (WO 2007/084181).

(Continued)

*Primary Examiner* — Sean E Aeder
*Assistant Examiner* — Julie Wu
(74) *Attorney, Agent, or Firm* — Tom Hunter; Weaver Austin Villeneuve & Sampson LLP

(57) ABSTRACT

Anti-EGFR family member antibodies and bispecific antibodies comprising one or more anti-EGFR family member antibodies are disclosed. These antibodies can be used to advantage to specifically target forms of cancer associated with the overexpression of members of the EGFR protein family.

18 Claims, 25 Drawing Sheets

(56) References Cited

OTHER PUBLICATIONS

PCT Written Opinion dated Jun. 17, 2008 issued in PCT/US2006/023479 (WO 2007/084181).
Australian Examiner's First Report dated Apr. 18, 2011 issued in AU2006336279.
Chinese Notice of Payment of the Restoration Fee for Unity of Invention dated Sep. 1, 2010 issued in CN200680029687.5.
Chinese First Office Action dated Jan. 4, 2011 issued in CN200680029687.5.
Chinese Second Office Action dated Sep. 9, 2011 issued in CN200680029687.5.
Chinese Decision on Rejection dated Jun. 12, 2012 issued in CN200680029687.5.
Chinese Reexamination Decision dated Jan. 9, 2013 issued in CN200680029687.5.
Chinese Third Office Action dated Mar. 8, 2013 issued in CN200680029687.5.
European Supplementary Search Report dated Apr. 23, 2009 issued in EP 06784990.
European Examination Report-1 dated Aug. 20, 2009 issued in EP 06 784 990.1.
European Examination Report-2 dated Mar. 19, 2010 issued in EP 06 784 990.1.
Response including references to European Patent Office dated Sep. 28, 2010 regarding EP Office Action of Mar. 19, 2010 issued in EP 06 784 990.1.
European Summons to attend Oral Proceedings pursuant to Rule 115(1) EPC dated Nov. 2, 2010 issued in EP 06 784 990.1-2406 / 1912674.
EP Correction of a decision under Rule 140 EPC dated Mar. 7, 2012 issued in EP 06 784 990.1-2406, 1 page.
European Communication (PCT prosecution documents) dated Oct. 10, 2008 issued in EP 06 784 990.1-2406, 13 pages.
European Communication (with amended claims; Form 1037) dated Nov. 4, 2008 issued in EP 06 784 990.1-2406, 15 pages.
European Communication dated Mar. 5, 2009 (including Invitation dated Jan. 8, 2009; sequence listing; Annex) issued in EP 06 784 990.1-2406, 6 pages.
European Communication dated May 12, 2009 with European Supplementary Search Report dated Apr. 23, 2009 issued in EP 06 784 990.1-2406, 10 pages.
European Communication (with Amended claims 1-25, Form 1005) dated Jul. 20, 2009 issued in EP 06 784 990.1-2406, 6 pages.
European Examination Report dated Aug. 20, 2009 issued in EP 06 784 990.1-2406, 3 pages.
European Response to Communication of Aug. 20, 2009 (including Amended claims; marked up claims; Sequence listing in TXT and PDF format) dated Dec. 23, 2009 issued in EP 06 784 990.1-2406, 12 pages.
European Examination Report dated Mar. 19, 2010 issued in EP 06 784 990.1-2406, 7 pages.
European Communication dated Jul. 27, 2010 and Extension of Time dated Jul. 20, 2010 issued in EP 06 784 990.1-2406, 3 pages.
European letter in response to communication dated Mar. 19, 2010 (with claims; Stratagene technical information; Normanly et al. article; Replacement pp. 9 and 10 of sequence listings) dated Sep. 28, 2010 issued in EP 06 784 990.1-2406, 18 pages.
European Communication regarding Summons to attend oral proceedings pursuant to Rule 115(1) EPC dated Nov. 2, 2010 issued in EP 06 784 990.1-2406, 11 pages.
European Communication regarding Oral Proceedings (Main Request Claims; Replacement Pages; First and Second Auxiliary Request claims; Replacement sequence listing; Declaration by Dr. Ulrik Nielsen, including Appendices I-III and Figures 1-9) dated Dec. 21, 2010 issued in EP 06 784 990.1-2406, 10 pages.
European Communication regarding Result of consultation dated Feb. 1, 2011 (with letter dated Jan. 20, 2011 including claims, Declaration and prosecution) issued in EP 06 784 990.1-2406, 56 pages.
European Communication regarding result of consultation (Feb. 1, 2011) dated Feb. 9, 2011 issued in EP 06 784 990.1-2406, 5 pages.
European Communication regarding filed amendments, claims and replacement sequence listing dated Feb. 7, 2011 issued in EP 06 784 990.1-2406, 42 pages.
European Communications dated Feb. 7, 2011 and Feb. 9, 2011 (regarding claims and filed amendments) issued in EP 06 784 990.1-2406, 59 pages.
European prosecution letter and amended claims dated Feb. 16, 2011 issued in EP 06 784 990.1-2406, 102 pages.
European Brief Communication dated Feb. 22, 2011 (faxed Feb. 17, 2011) issued in EP 06 784 990.1-2406 7 pages.
European Communication regarding Result of Consultation (Feb. 16, 2011) dated Feb. 23, 2011 issued in EP 06 784 990.1-2406, 3 pages.
European Communication under Rule 71(3) EPC for Grant (Bibliographical data; Description) dated Apr. 11, 2011 issued in EP 06 784 990.1- 2406, 106 pages.
Response to EP Communication under Rule 71(3) EPC for Grant (Apr. 11, 2011) dated Aug. 17, 2011 issued in EP 06 784 990.1-2406, 18 pages.
EP Documents for Grant of a patent dated Aug. 30, 2011 issued in EP 06 784 990.1-2406, 4 pages.
EP Grant Documents for patent dated Nov. 9, 2011 issued in EP 06 784 990.1-2406, 8 pages.
European Extended Search Report dated Apr. 19, 2012 issued in EP 11 177 829.6-2406/2425850.
Japanese Office Action dated Sep. 30, 2011 issued in JP2008-517139.
PCT International Search Report dated Mar. 20, 2009 issued in PCT/US07/24287 (WO 2008/140493).
PCT Written Opinion dated Mar. 20, 2009 issued in PCT/US07/24287 (WO2008/140493).
PCT International Preliminary Report on Patentability dated May 26, 2009 issued in PCT/US07/24287 (WO2008/140493).
European Search Report dated Apr. 19, 2013 issued in EP 07 874 142.8.
European Communication dated May 8, 2013 issued in EP 07 874 142.8.
Adams et al. (1992) "Comparison of the Pharmacokinetics in Mice and the Biological Activity of Murine L6 and Human-Mouse Chimeric Ch-L6 Antibody." *Antibody, Immunoconjugates and Radiopharmaceuticals*, 5(1):81-95.
Adams et al. (Sep. 1, 1993) "Highly specific in Vivo tumor targeting by monovalent and divalent forms of 741F8 anti-c-*erb*B-2 single-chain Fv" *Cancer Research*, 53(17):4026-4034.
Adams et al. (1996) "Influence of avidity on the tumor retention of monospecific and bispecific anti-c-erbB-2 single-chain Fv dimers." *Proceedings of the American Association of Cancer Research*, No. 3217: p. 472.
Adams et al. (Feb. 1, 1998) "Increased Affinity Leads to Improved Selective Tumor Delivery of Single-Chain Fv Antibodies", *Cancer Research*, 58:485-490.
Adams et al. (Sep. 2005) "Monoclonal antibody therapy of cancer", *Nature Biotechnology*, 23(9):1147-1157.
Adams et al. (Mar. 1, 2006) "Avidity-Mediated Enhancement of In vivo Tumor Targeting by Single-Chain Fv Dimers", *Clinical Cancer Research*, 12(5):1599-1605.
Agrawal et al. (1991) "Pharmacokinetics, biodistribution, and stability of oligodeoxynucleotide phosphorothioates in mice." Proceedings of the National Academy of Sciences, USA, vol. 88(17): pp. 7595-7599.
Baselga, Jose (2002) "Why the Epidermal Growth Factor Receptor? The Rationale for Cancer Therapy", *The Oncologist* 7(suppl 4):2-8 [Downloaded from www.TheOncologist.com on Nov. 21, 2008].
Beaumier et al. (1985) "Melanoma localization in nude mice with monoclonal Fab against p97", *The Journal of Nuclear Medicine*, 26:1172-1179.
Beckman et al. (Jan. 15, 2007) "Antibody Constructs in Cancer Therapy, Protein Engineering Strategies to Improve Exposure in Solid Tumors", *American Cancer Society*, 109(2):170-179.
Berger et al. (1988) "Correlation of c-*erbB*-2 gene amplification and protein expression in human breast carcinoma with nodal status and nuclear grading", *Cancer Research*, 48(5):1238-1243.

(56) References Cited

OTHER PUBLICATIONS

Boado and Pardridge (1994) "Complete Inactivation of Target mRNA by Biotinylated Antisense Oligodeoxynucleotide-Avidin Conjugates", *Bioconjugate Chem.*, 5:406-410.

Boado and Pardridge (1998) "Ten nucleotide cis element in the 3'-untranslated region of the GLUT1 glucose transporter mRNA increases gene expression via mRNA stabilization." *Molecular Brain Research*, 59:109-113.

Boado et al. (1998) "Drug Delivery of Antisense Molecules to the Brain for Treatment of Alzheimer's Disease and Cerebral AIDS" *Journal of Pharmaceutical Sciences*, 87(11):13081315.

Boado et al. (1999) "Selective expression of the large neutral amino acid transporter at the blood-brain barrier" *Proceedings of the National Academy of Sciences*, USA, 96(21):1207912084.

Boado et al. (2000) "Antisense-Mediated Down-Regulation of the Human Huntingtin Gene", *The Journal of Pharmacology and Experimental Therapeutics*, 295(1):239-243.

Brown et al. (1994) "Effect of Phosphorothioate Modification of Oligodeoxynucleotides on Specific Protein Binding", *The Journal of Biological Chemistry*, 269(43):26801-26805.

Cao, Ying and Lam, Laura (2003) "Bispecific antibody conjugates in therapeutics" *Advanced Drug Delivery Reviews*, 55(2):171-197.

Cao and Lam (2003) "Bispecific antibody conjugates in therapeutics", *Advanced Drug Delivery Reviews*, 55(2):171-197.

Chen et al. (1990) "Disposition and Metabolism of Oligodeoxynucleoside Methylphosphonate Following a Single iv Injection in Mice", *Drug Metabolism Disposition*, 8(5):815-818.

Chinnery et al. (1999) "Peptide nucleic acid delivery to human mitochondria", *Gene Therapy*, 6:1919-1928.

Colcher et al. (1990) "In Vivo Tumor Targeting of a Recombinant Single-Chain Antigen- Binding Protein," *Journal of the National Cancer Institute*, 82(14):1191-1197.

Coloma et al. (2000) "Transport Across the Primate Blood-Brain Barrier of a Genetically Engineered Chimeric Monoclonal Antibody to the Human Insulin Receptor." *Pharmaceutical Research*, 17(3):266-274.

Cossum et al. (1993) "Disposition of the $^{14}$C-labeled phosphorothioate oligonucleotide ISIS 2105 after intravenous administration to rats", *The Journal of Pharmacology Experimental Therapeutics*, 267(3):1181-1190.

Crooke (1993) "Progress toward oligonucleotide therapeutics: pharmacodynamic properties", *FASEB Journal*, 7(6):533-539.

Cruse and Lewis (2003) *Atlas of Immunology*, 2nd Edition Chapter Immunoglobulin, Synsthesis, Properties, Structure and Function, pp. 184-185.

de Smidt et al. (1991) "Association of antisense oligonucleotides with lipoproteins prolongs the plasma half-life and modifies the tissue distribution", *Nucleic Acids Research*, 19(17):4695-4700.

Demidov et al. (1994) "Stability of peptide nucleic acids in human serum and cellular extracts", *Biochemical Pharmacology*, 48:1310-1313.

Desplancq et al. (1994), "Multimerization Behaviour of Single Chain Fv Variants for the Tumour-binding Antibody B72.3," Protein Eng., Oxford Unv. Press, Surrey, GB, vol. 7, No. 8, Aug. 1, 1994; XP0004450771; ISSN: 0269-2139; pp. 1027-1033.

Gee et al. (1998) "Assessment of High-Affinity Hybridization, rNase H Cleavage, and Covalent Linkage in Translation Arrest by Antisense Oligonucleotides." *Antisense and Nucleic Acid Drug Develop*, 8:103-111.

Hanvey et al. (1992) "Antisense and Antigene Properties of Peptide Nucleic Acids", *Science*, 258:1481-1486.

Heffetz et al. (1989) "Antibodies directed against phosphothreonine residues as potent tools for studying protein phosphorylation", *European Journal of Biochemistry*, 182: 343-348.

Heiss (2003) "In vivo Efficacy of Trifunctional Bispecific Antibodies in Treatment of Symptomatic Malignant Ascities", *Proceedings of the American Society of Clinical Oncology*, 22:173 (abstract 693).

Hnatowich (1999) "Antisense and nuclear medicine", *The Journal of Nuclear Medicine*, 40(4):693-703.

Holliger et al. (1993) "Diabodies": Small bivalent and bispecific antibody fragements, *Proceedings of the National Academy of Sciences*, USA, 90(14):6444-6448.

Horak et al. (Dec. 2005) "Isolation of scFvs to In Vitro Produced Extracellular Domains of EGFR Family Members", *Cancer Biotherapy & Radiopharmaceuticals*, 20(6):603-614.

Hu et al. (1996) "Minibody: A Novel Engineered Anti-Carcinoembryonic Antigen Antibody Fragment (Single-Chain Fv-$C_H3$) Which Exhibits Rapid, High-Level Targeting of Xenografts", *Cancer Research*, 56:3055-3061.

Hurwitz et al. (Apr. 11, 1995) "Suppression and promotion of tumor growth by monoclonal antibodies to ErbB-2 differentially correlate with cellular uptake." *Proceedings of the National Academy of Sciences*, USA, 92(8):3353-3357.

Huwyler and Pardridge (1998) "Examination of Blood—rain Barrier Transferrin Receptor by Confocal Fluorescent Nicroscopy of Unfixed Isolated Rat Brain Capillaries" *Journal of Neurochemistry*, 70:883-886.

Hynes and Stern (1994) "The biology of *erbB-2/neu/HER-2* and its role in cancer", *Biochimica et Biophysica Acta*, 1198:165-184.

Kalies et al. (1994) "Binding of Ribosomes to the Rough Endoplasmic Reticulum Mediated by the Sec61p-Complex," *Journal of Cell Biology*, 126(4):925-934.

Kang et al. (1995) "Pharmacokinetics and organ clearance of a 3'-biotinylated, internally [$^{32}$P]-labeled phosphodiester oligodeoxynucleotide coupled to a neutral avidin/monoclonal antibody conjugate", *Drug Metabolism and Disposition*, 23(1):55-59.

Keler et al. (Sep. 15, 1997) "Bispecific Antibody-dependent Cellular Cytotoxicity of HER2/neu-overexpressing Tumor Cells by FcγReceptor Type I-expressing Effector Cells1", *Cancer Research*, 57:4008-4014.

Kobori et al. (1999) "Visualization of mRNA expression in CNS using $^{11}$C-labeled phosphorothioate oligodeoxynucleotide", *NeuroReport*, 10:2971-2974.

Krieg et al. (1993) "Modification of antisence phosphodiester oligodeoxynucleotides by a 5' cholesteryl moiety increases cellular association and improves efficacy", *Proceedings of the National Academy of Sciences*, USA, 90(3):1048-1052.

Kroesen et al. (1998) "Bispecific antibodies for treatment of cancer in experimental animal models and man" *Advanced Drug Delivery Reviews*, 31(1):105-129.

Kurihara and Pardridge (1999) "Imaging Brain Tumors by Targeting Peptide Radiopharmaceuticals through the Blood-Brain Barrier", *Cancer Research*, 54: 6159-6163.

Kurihara et al. (1999) "Epidermal Growth Factor Radiopharmaceuticals: $^{111}$In Chelation, Conjugation to a Blood-Brain Barrier Delivery Vector via a Biotin-Polyethlene Linker, Pharacokinetics, and in Vivo Imaging of Experimental Brain Tumors", *Bioconjugate Chem.*, 10:502-511.

Langley et al. (1998) Identification of Multiple Forms of 180-kDa Ribosome Receptor in Human Cells, *DNA and Cell Biology*, 17(5):449-460.

Lee et al. (2000) "Targeting Rat Anti-Mouse Transferrin Receptor Monoclonal Antibodies through Blood-Brain Barrier in Mouse", *The Journal of Pharmacology and Experimental Therapeutics*, 292(3):1048-1052.

Li et al. (1999) "Genetically engineered brain drug delivery vectors: cloning, expression and in vivo application of an anti-transferrin receptor single chain antibody-streptavidin fusion gene and protein", *Protein Engineering*, 12(9):787-796.

Lockhart and Winzeler (2000) "Genomics, gene expression and DNA arrays", Nature, 405:827-836.

Lohrisch and Piccart (2001) "An Overview of HER2", *Seminars in Oncology*, 28(6):(Suppl 18):3-11.

Mash et al. (1990) "Characterization and Distribution of Transferrin Receptors in the Rat Brain", *Journal of Neurochemistry*, 55:1972-1979.

Mayfield and Corey (1999) "Automated Synthesis of Peptide Nucleic Acids and Peptide Nucleic Acid—Peptide Conjugates," *Analytical Biochemistry*, 268:401-404.

McCall et al. (2001) "Increasing the Affinity for Tumor Antigen Enhances Bispecific Antibody Cytotoxicity", *J. Immunol.*, 166:6112-6117.

(56) References Cited

OTHER PUBLICATIONS

Milenic et al. (1991) "Construction, Binding Properties, Metabolism, and Tumor Targeting of a Single-Chain Fv Derived from the Pancarcinoma Monoclonal Antibody CC49", *Cancer Research*, 51:6363-6371.
Nielsen et al. (1994) "Peptide Nucleic Acid (PNA). A DNA Mimic with a Peptide Backbone." *Bioconjugate Chem.*, 5:3-7.
Normanly et al. (Sep. 1986) "Construction of two *Escherichia coli* amber suppressor genes: tRNA CUA-Phe and tRNA CUA-cys", *PNAS*, USA, 83:6548-6552.
O'Reilly et al. (1991) "The relationship between c-erbB-2 expression, S-phase fraction and prognosis in breast cancer", *British Journal of Cancer*, 63:444-446.
Pack and Pluckthun (1992) "Miniantibodies: use of amphipathic helixes to produce functional, flexibly linked dimeric FV fragments with high avidity in *Escherichia coli*." *Biochemistry*, 31(6):1579-1584.
Pack et al. (1993) "Improved Bivalent Miniantibodies, with Identical Avidity as Whole Antibodies, Produced by High Cell Density Fermentation of *Escherichia coli*", *Bio/Technology*, 11:1271-1277.
Pardridge (1997) "Drug Delivery to the Brain", *Journal of Cerebral Blood Flow and Metabollism*, 17:713-731.
Pardridge (Jan. 2001) "Drug targeting," *Drug Discovery Today*, 6(2):104-106.
Pardridge et al. (1995) "Human Insulin Receptors Monoclonal Antibody Undergoes High Affinity Binding to Human Brain Capillaries in Vitro and Rapid Transcytosis Through the Blood-Brain Barrier in vivo in the Primate", *Pharmaceutical Research*, 12(6):807-816.
Pardridge et al. (1995) "Vector-mediated delivery of a polyamide ("peptide") nucleic acid analogue through the blood-brain barrier in vivo", *Proceedings of the National Academy of Sciences*, USA, 92(12):5592-5596.
Paul, William E. (1993) Fundamental Immunology, 3rd Edition, Raven Press Ltd, New York, NY., pp. 292-295.
Penichet et al. (1999) "An Antibody-Avidin Fusion Protein Specific for the Transferrin Receptor Serves as a Delivery Vehicle for Effective Brain Targeting: Initial Applications in Anti-HIV Antisense Drug Delivery to the Brain", *The Journal of Immunology*, 163:4421-4426.
Pérez-Soler (2004) "HER1/EGFR Targeting: Refining the Strategy", *The Oncologist*, Montefiore Medical Center/Albert Einstein College of Medicine, Bronx, New York, USA, 9:58-67.
Press et al. (1993) "HER-2/*neu* expression in node-negative breast cancer: direct tissue quantitation by computerized image analysis and association of overexpression with increased risk of recurrent disease", *Cancer Research*, 53(20):4960-4970.
Pullarkat et al. (Apr. 1999) "A phase I study of a HER2/neu bispecific antibody with granulocyte-colony-stimulating factor in patients with metastatic breast cancer that overexpresses HER2/neu," *Cancer Immunol. Immunother*, 48:9-21.
Rebert et al. (1990) "Acute Interactive Pharmacologic Effects of Inhaled Toluene and Dichloromethane on Rat Brain Electrophysiology", *Pharmacology Biochemistry & Behavior*, 36:351-356.
Robinson et al. (2008) "Targeting ErbB2 and ErbB3 with a bispecific single-chain Fv enhances targeting selectivity and induces a therapeutic effect in vitro", *British Journal of Cancer*, 99:1415-1425 doi:10.1038/sj.bjc.6604700 (Published online Oct. 7, 2008).
Rockwell et al. (1997) "Cell-surface perturbations of the epidermal growth factor and vascular endothelial growth factor receptors by phosphorothioate oligodeoxynucleotides", *Proceedings of the National Academy of Sciences*, USA, 94(12):6523-6528.
Rudikoff et al. (1982) "Single amino acid substitution altering antigen-binding specificity," *Proc. Natl. Acad. Sci.* USA, 79:1979-1983, Mar. 1982.
Samii et al. (1994) "Blood-brain barrier transport of neuropeptides: analysis with a metabolically stable dermorphin analogue", *American Journal of Physiology*, 267:E124-E134.
Sathasivam et al. (1999) "Transgenic Models of Huntington's disease", *Philosophical Transactions of The Royal Society of London*, 354:963-969.
Savitz and Meyer (Aug. 9, 1990) "Identification of a ribosome receptor in the rough endoplasmic reticulum," *Nature*, 346:540-544.
Savitz and Meyer (Feb. 1993) "180-1(D Ribosome Receptor is Essential for Both Ribosome Binding and Protein Translocation," *Journal of Cell Biology*, 120(4):853-863.
Schier et al. (1995) "In vitro and in vivo characterization of a human anti-c-erbB-2 single- chain Fv isolated from a filamentous phage antibody library." *Immunotechnology*, 1:73-81.
Schier et al. (1996) "Isolation of High-affinity Monomeric Human Anti-c-erbB-2 Single chain Fv Using Affinity-driven Selection", *Journal of Molecular Biology*, 255(1):28-43.
Schier et al. (1996) "Isolation of Picomolar Affinity Anti-c-erbB-2 Single-Chain Fv by Molecular Evolution of the Complementarity Determining Regions in the Center of the Antibody Binding Site." *Journal of Molecular Biology*, 263(4):551-567.
Schmidt, M. et al. (1996) "A Bivalent Single-Chain Antibody-Toxin Specific for ErbB-2 and the EGF Receptor," International Journal of Cancer. John Wiley & Sons, Inc., US, Switzerland, Germany, vol. 65, No. 4, Feb. 8, 1996, XP000646380, ISSN: 00207136; pp. 538-546.
Seshadri et al. (1993) "Clinical Significance of HER-2/*neu* Oncogene Amplification in Primary Breast Cancer", *The South Australian Breast Cancer Study Group; Journal of Clinical Oncology*, 11(10):1936-1942.
Shahied et al. (Issue of Dec. 24, 2004) "Bispecific Minibodies Targeting HER2/*neu* and CD16 Exhibit Improved Tumor Lysis When Placed in a Divalent Tumor Antigen Binding Format", *The Journal of Biological Chemistry*, 279(52):53907-53914.
Shalaby et al. (Jan. 1992) "Development of Humanized Bispecific Antibodies Reactive with Cytotoxic Lymphocytes and Tumor Cells Overexpressing the *HER2* Protooncogene", *Journal of Experimental Medicine*, 175:217-225.
Shalaby et al. (1995) "Bispecific *HER2* X CD3 Antibodies Enhance T-Cell Cytotoxicity in Vitro and Localize to *HER2*-Overexpressing Xenographs in Nude Mice", *Clinical Immunology and Immunopathology*, 74(2):185-192.
Shechter et al. (1982) "Autoantibodies to Insulin Receptors Spontaneously Develop as Anti-Idiotypes in Mice Immunized with Insulin", *Science*, 216:542-545.
Shi and Pardridge (2000) "Noninvasive gene targeting to the brain", *Proceedings of the National Academy of Sciences*, USA, 97(13):7567-7572.
Shi et al. (2000) "Antisense imaging of gene expression in the brain in vivo", *Proceedings of the National Academy of Sciences*, USA, 97(26):14709-14714.
Skarlatos et al. (1995) "Transport of [$^{125}$I] transferrin through the rat blood-brain barrier", *Brain Research*, 683:164-171.
Slamon et al. (1989) "Studies of the HER-2/neu Proto-oncogene in Human Breast and Ovarian Cancer", *Science*, 244(4905):707-712.
Slamon et al. (1987) "Human Breast Cancer: Correlation of Relapse and Survival with Amplification of the HER-2/*neu* Oncogene", *Science*, 235:177-181.
Stancovski et al. (1991) "Mechanistic aspects of the opposing effects of monoclonal antibodies to the ERBB2 receptor on tumor growth," Proceedings of the National Academy of Sciences, USA, 88(19):8691-8695.
Stein and Cheng (1993) "Antisense Oligonucleotides as Therapeutic Agents—Is the Bullet Really Magical?" *Science*, 261:1004-1012.
Tavitian et al. (1998) "In vivo imaging of oligonucleotides with positron emission tomography" *Nature Medicine*, 4(4):467-471.
Tsukamoto et al. (1997) "Site-Directed Deletion of a 10-Nucleotide Domain of the 3'-Untranslated Region of the GLUT1 Glucose Transporter mRNA Eliminates Cytosolic Protein Binding in Human Brain Tumors and Induction of Reporter Gene Expression" *Journal of Neurochemistry*, 68:2587-2592.
Tyler et al. (1999) "Peptide nucleic acids targeted to the neurotensin receptor and administered i.p. cross the blood-brain barrier and specifically reduce gene expression", *Proceedings of the National Academy of Sciences*, USA, 96(12):7053-7058.
Ueda et al. (1993) "Rate of $^{59}$Fe Uptake into Brain and Cerebrospinal Fluid and the Influence Thereon of Antibodies Against the Transferrin Receptor." *Journal of Neurochemistry*, 60:106-113.
Wanker et al. (1995) Functional Characterization of the 180-kD Ribosome Receptor in Vivo, *Journal of Cell Biology*, 130(1):29-39.

(56) References Cited

OTHER PUBLICATIONS

Weiner et al. (Jan. 1, 1993) "A Human Tumor Xenograft Model of Therapy with a Bispecific Monoclonal Antibody Targeting c-erbB-2 and CD16I", *Cancer Research*, 53:94-100.

Whitesell et al. (1993) "Stability, clearance, and disposition of intraventricularly administered oligodeoxynucleotides: Implications for therapeutic application within the central nervous system", *Proceedings of the National Academy of Sciences*, USA, 90(10):4665-4669.

Wickstrom (1986) "Oligodeoxynucleotide stability in subcellular extracts and culture media", *Journal of Biochemical and Biophysical Methods*, 13:97-102.

Wild et al. (1999) "Tumor Therapy with Bispecific Antibody: The Targeting and Triggering Steps Can Be Separated Employing a CD2-Based Strategy", *The Journal of Immunology*, 163(4):2064-2072.

Wittung et al. (1994) "DNA-like double helix formed by peptide nucleic acid", *Nature*, 368:561-563.

Wojcik et al. (1996) "Chronic Intrathecal Infusion of Phosphorothioate or Phosphodiester Antisense Oligonucleotides against Cytokine Responsive Gene-2/IP-10 in Experimental Allergic Encephalomyelitis of Lewis Rat" *The Journal of Pharmacology and Experimental Therapeutics*, 278(1):404-410.

Wolff et al. (1993) "Monoclonal antibody homodimers: enhanced antitumor activity in nude mice", *Cancer Research*, 53(11):2560-2565.

Wu et al. (1996) "Pharmacokinetics and blood-brain barrier transport of [$^3$H]-biotinylated phosphorothioate oligodeoxynucleotide conjugated to a vector-mediated drug delivery system", *The Journal of Pharmacology and Experimental Therapeutics*, 276(1):206-211.

Warden and Sliwkowski (2001) "Untangling the ErbB Singalling Network." Nature, Reviews, *Molecular Cell Biology*, 2:127-137.

Zendegui et al. (1992) "In vivo stability and kinetics of absorption and disposition of 3' phosphopropyl amine oligonucleotides", *Nucleic Acids Research*, 20(2):307-314.

Zhang and Pardridge (2001) "Rapid transferrin efflux from brain to blood across the blood-brain Barrier", *Journal of Neurochemistry*, 76:1597-1600.

Zhao et al. (1999) "Brain Insulin Receptors and Spatial Memory", *The Journal of Biological Chemistry*, 274(49):34893-34902.

Zhou et al. (2000) "HER-2/*neu* Blocks Tumor Necrosis Factor-induced Apoptosis via the Akt/NF-$K$b Pathway", *The Journal of Biological Chemistry*, 275(11):8027-8031.

Zick et al. (1984) "The Role of Antireceptor Antibodies in Stimulating Phosphorylation of the Insulin Receptor", *The Journal of Biological Chemistry*, 259(7): 4396-4400.

\* cited by examiner

Heavy Chain:

| Clone | Framework 1 | CDR1 | Framework 2 | CDR2 |
|---|---|---|---|---|
| C6.5  | QVQLVQSGAEVKKPGESLKISCKGSGYSFT | SYWIA | WVRQMPGKGLEYMG | LIYPGDSDTKYSPSFQG |
| G98A  | QVQLVQSGAEVKKPGESLKISCKGSGYSFT | SYWIA | WVRQMPGKGLEYMG | LIYPGDSDTKYSPSFQG |
| ML3-9 | QVQLVQSGAEVKKPGESLKISCKGSGYSFT | SYWIA | WVRQMPGKGLEYMG | LIYPGDSDTKYSPSFQG |
| H3B1  | QVQLVQSGAEVKKPGESLKISCKGSGYSFT | SYWIA | WVRQMPGKGLEYMG | LIYPGDSDTKYSPSFQG |
| B1D2  | QVQLVQSGAEVKKPGESLKISCKGSGYSFT | SYWIA | WVRQMPGKGLEYMG | LIYPGDSDTKYSPSFQG |

| Framework 3 | CDR3 | Framework 4 |
|---|---|---|
| QVTISVDKSVSTAYLQWSSLKPSDSAVYFCAR | HDVGYCSSSNCAKWPEYFQH | WGQGTLVTVSS |
| QVTISVDKSVSTAYLQWSSLKPSDSAVYFCAR | HDVAYCSSSNCAKWPEYFQH | WGQGTLVTVSS |
| QVTISVDKSVSTAYLQWSSLKPSDSAVYFCAR | HDVGYCSSSNCAKWPEYFQH | WGQGTLVTVSS |
| QVTISVDKSVSTAYLQWSSLKPSDSAVYFCAR | HDVGYCTDRTCAKWPEYFQH | WGQGTLVTVSS |
| QVTISVDKSVSTAYLQWSSLKPSDSAVYFCAR | HDVGYCTDRTCAKWPEWLGV | WGQGTLVTVSS |

Light Chain:

| Clone | Framework 1 | CDR1 | Framework 2 | CDR2 |
|---|---|---|---|---|
| C6.5  | QSVLTQPPSVSAAPGQKVTISC | SGSSSNIGNNYVS | WYQQLPGTAPKLLIY | GHTNRPA |
| G98A  | QSVLTQPPSVSAAPGQKVTISC | SGSSSNIGNNYVS | WYQQLPGTAPKLLIY | GHTNRPA |
| ML3-9 | QSVLTQPPSVSAAPGQKVTISC | SGSSSNIGNNYVS | WYQQLPGTAPKLLIY | DHTNRPA |
| H3B1  | QSVLTQPPSVSAAPGQKVTISC | SGSSSNIGNNYVS | WYQQLPGTAPKLLIY | DHTNRPA |
| B1D2  | QSVLTQPPSVSAAPGQKVTISC | SGSSSNIGNNYVS | WYQQLPGTAPKLLIY | DHTNRPA |

| Framework 3 | CDR3 | Framework 4 |
|---|---|---|
| GVPDRFSGSKSGTSASLAISGFRSEDEADYYC | AAWDDSLSGWV | FGGGTKLTVLG |
| GVPDRFSGSKSGTSASLAISGFRSEDEADYYC | ASWDYTLSGWV | FGGGTKLTVLG |
| GVPDRFSGSKSGTSASLAISGFRSEDEADYYC | ASWDYTLSGWV | FGGGTKLTVLG |
| GVPDRFSGSKSGTSASLAISGFRSEDEADYYC | ASWDYTLSGWV | FGGGTKVTVLG |
| GVPDRFSGSKSGTSASLAISGFRSEDEADYYC | ASWDYTLSGWV | FGGGTKVTVLG |

*Fig. 13*

V_H Alignments

|  | FR1 | CDR1 | FR2 |
|---|---|---|---|
| A5 VH | QVQLVQSGGGLVKPGGSLRLSCAASGFSFN | TYDMN | WVRQAPGKGLEWVS |
| B12 VH | QVQLVQSGGGLVQPGRSLRLSCAASGFTFD | DYAMH | WVRQAPGKGLEWVS |
| B1D2 VH | QVQLVQSGAEVKKPGESLKISCKGSGYSFT | SYWIA | WVRQMPGKGLEYMG |
| ML3.9 VH | QVQLVQSGAEVKKPGESLKISCKGSGYSFT | SYWIA | WVRQMPGKGLEYMG |
| F4 VH | QVQLQESGGGLVKPGGSLRLSCAASGFTFS | SYAMS | WVRQAPGKGLEWVS |
| P5B6H2 VH | QVQLVESGGGLVQPGGSLRLSCAASGFTFR | SYAMS | WVRQAPGKGLEWVS |
| H3 VH | QVQLQESGGGLVKPGGSLRLSCAASGFTFS | SYWMS | WVRQAPGKGLEWVA |

|  | CDR2 | FR3 |
|---|---|---|
| A5 VH | SISSSSSYIYYADSVKG | RFTISRDNAKNSLYLQMNSLRAEDTAVYYCAR |
| B12 VH | GISWNSGSIGYADSVKG | RFTISRDNAKNSLYLQMNSLRPEDTAVYYCAR |
| B1D2 VH | LIYPGDSDTKYSPSFQG | QVTISVDKSVSTAYLQWSSLKPSDSAVYFCAR |
| ML3.9 VH | LIYPGDSDTKYSPSFQG | QVTISVDKSVSTAYLQWSSLKPSDSAVYFCAR |
| F4 VH | TISGSGGSTYYADSVKG | RFTISRDNSKNTLYLQMNSLRAEDTAVYYCAK |
| P5B6H2 VH | AISGRGDNTYYADSVKG | RFTISRDNSKNTLYLQMNSLRAEDTAVYYCAK |
| H3 VH | NINRDGSASYYVDSVKG | RFTISRDDAKNSLYLQMNSLRAEDTAVYYCAR |

|  | CDR3 | FR4 |
|---|---|---|
| A5 VH | DG---V-------ATTPFDY | WGQGTLVTVSS |
| B12 VH | DLGAKQ-------WLEGFDY | WGQGTLVTVSS |
| B1D2 VH | HDVGYCTDRTCAKWPEWLGV | WGQGTLVTVSS |
| ML3.9 VH | HDVGYCSSSNCAKWPEYFQH | WGQGTLVTVSS |
| F4 VH | GYSSSW-------SEVASGY | WGQGTLVTVSS |
| P5B6H2 VH | MTSN---------AVGFDY | WGQGTLVTVSS |
| H3 VH | DRGVG----------YFDL | WGRGTLVTVSS |

Fig. 14A

V_L Alignments

|      | FR1 | CDR1 |
|---|---|---|
| A5 VL | QSVLTQPPS-VSGAPGQRVTISC | TGSSSNIGAGYDVH |
| P5B6H2 VL | QSVLTQPPS-VSGAPGQRVTISC | TGRHSNIGLGYGVH |
| B1D2 VL | QSVLTQPPS-VSAAPGQKVTISC | SGSSSNIGNNY-VS |
| ML3.9 VL | QSVLTQPPS-VSAAPGQKVTISC | SGSSSNIGNNY-VS |
| B12 VL | SYELTQDPA-VSVALGQTVRITC | QG---DSLRSYYAS |
| F4 VL | AIVMTQSPSSLSASVGDRVTITC | RAS---QGIRNDLG |
| H3 VL | QSALTQPAS-VSGSPGQSITISC | TGTSSDVGGYNFVS |

|      | FR2 | CDR2 | FR3 |
|---|---|---|---|
| A5 VL | WYQQLPGTAPKLLIY | GNSNRPS | GVPDRFSGSKSGTSASLAITGLQAEDEADYYC |
| P5B6H2 VL | WYQQLPGTAPKLLIY | GNTNRPS | GVPDRFSGFKSGTSASLAITGLQAEDEADYYC |
| B1D2 VL | WYQQLPGTAPKLLIY | DHTNRPA | GVPDRFSGSKSGTSASLAISGFRSEDEADYYC |
| ML3.9 VL | WYQQLPGTAPKLLIY | DHTNRPA | GVPDRFSGSKSGTSASLAISGFRSEDEADYYC |
| B12 VL | WYQQKPGQAPVLVIY | GKNNRPS | GIPDRFSGSTSGNSASLTITGAQAEDEADYYC |
| F4 VL | WYQQKAGKAPKLLIY | AASSLQS | GVPSRFSGSGSGTDFTLTISSLQPDDFATYFC |
| H3 VL | WYQQHPGKAPKLMIY | DVSDRPS | GVSDRFSGSKSGNTASLIISGLQADDEADYYC |

|      | CDR3 | FR4 |
|---|---|---|
| A5 VL | QSYDSSLS-AL | FGGGTKLTVLG |
| P5B6H2 VL | QSYDRRTPGWV | FGGGTKLTVLG |
| B1D2 VL | ASWDYTLSGWV | FGGGTKLTVLG |
| ML3.9 VL | ASWDYTLSGWV | FGGGTKLTVLG |
| B12 VL | NSRDSSGNHWV | FGGGTKVTVLG |
| F4 VL | QQAHSFPP-T- | FGGGTKVEIKR |
| H3 VL | SSYGSSSTHVI | FGGGTKVTVLG |

Anti-EGFR

V_H Alignments

|  | FR1 | CDR1 | FR2 |
|---|---|---|---|
| C10 VH | EVQLVQSGAEVKKPGSSVKVSCKASGGTFS | SYAIS | WVRQAPGQGLEWMG |
| E12 VH | EVQLVQSGAEVKKPGSSVKVSCKASGGTFS | SYAIS | WVRQAPGQGLEWMG |

|  | CDR2 | FR3 |
|---|---|---|
| C10 VH | GIIPIFGTANYAQKFQG | RVTITADESTSTAYMELSSLRSEDTAVYYCAR |
| E12 VH | GIIPIFGTANYAQKFQG | RVTITADESTSTAYMELSSLRSEDTAVYYCAR |

|  | CDR3 | FR4 |
|---|---|---|
| C10 VH | EEGPYCSSTSCYGAFDI | WGQGTLVTVSS |
| E12 VH | EEGPYCSSTSCYGAFDI | WGQGTLVTVSS |

V_L Alignments

|  | FR1 | CDR1 |
|---|---|---|
| C10 VL | QSVLTQDPAVSVALGQTVKITC | QGDSLRSYFAS |
| E12 VL | QSVLTQDPAVSVALGQTVKITC | QGDSLRSYFAS |

|  | FR2 | CDR2 | FR3 |
|---|---|---|---|
| C10 VL | WYQQKPGQAPTLVMY | ARNDRPA | GVPDRFSGSKSGTSASLAISGLQSEDEADYYC |
| E12 VL | WYQQKPGQAPTLVMY | ARNDRPA | GVPDRFSGSKSGTSASLAISGLQSEDEADYYC |

|  | CDR3 | FR4 |
|---|---|---|
| C10 VL | AAWDDSLNGYL | FGAGTKLTVL |
| E12 VL | AAWDDSLNGYL | FGAGTKLTVL |

*Fig. 16*

Anti-Her2

V_H Alignments

|  |  | FR1 | CDR1 | FR2 |
|---|---|---|---|---|
| C6.5 | VH | QVQLVQSGAEVKKPGESLKISCKGSGYSFT | SYWIA | WVRQMPGKGLEYMG |
| G98A | VH | QVQLVQSGAEVKKPGESLKISCKGSGYSFT | SYWIA | WVRQMPGKGLEYMG |
| ML3-9 | VH | QVQLVQSGAEVKKPGESLKISCKGSGYSFT | SYWIA | WVRQMPGKGLEYMG |
| H3B1 | VH | QVQLVQSGAEVKKPGESLKISCKGSGYSFT | SYWIA | WVRQMPGKGLEYMG |
| B1D2 | VH | QVQLVQSGAEVKKPGESLKISCKGSGYSFT | SYWIA | WVRQMPGKGLEYMG |
| F5 | VH | QVQLVESGGGLVQPGGSLRLSCAASGFTFR | SYAMS | WVRQAPGKGLEWVS |
| F5B6H2 | VH | QVQLVESGGGLVQPGGSLRLSCAASGFTFR | SYAMS | WVRQAPGKGLEWVS |

|  |  | CDR2 | FR3 |
|---|---|---|---|
| C6.5 | VH | LIYPGDSDTKYSPSFQG | QVTISVDKSVSTAYLQWSSLKPSDSAVYFCAR |
| G98A | VH | LIYPGDSDTKYSPSFQG | QVTISVDKSVSTAYLQWSSLKPSDSAVYFCAR |
| ML3-9 | VH | LIYPGDSDTKYSPSFQG | QVTISVDKSVSTAYLQWSSLKPSDSAVYFCAR |
| H3B1 | VH | LIYPGDSDTKYSPSFQG | QVTISVDKSVSTAYLQWSSLKPSDSAVYFCAR |
| B1D2 | VH | LIYPGDSDTKYSPSFQG | QVTISVDKSVSTAYLQWSSLKPSDSAVYFCAR |
| F5 | VH | AISGRGDNTYYADSVKG | RFTISRDNSKNTLYLQMNSLRAEDTAVYYCAK |
| F5B6H2 | VH | AISGRGDNTYYADSVKG | RFTISRDNSKNTLYLQMNSLRAEDTAVYYCAK |

|  |  | CDR3 | FR4 |
|---|---|---|---|
| C6.5 | VH | HDVGYCSSSNCAKWPEYFQH | WGQGTLVTVSS |
| G98A | VH | HDVAYCSSSNCAKWPEYFQH | WGQGTLVTVSS |
| ML3-9 | VH | HDVGYCSSSNCAKWPEYFQH | WGQGTLVTVSS |
| H3B1 | VH | HDVGYCTDRTCAKWPEYFQH | WGQGTLVTVSS |
| B1D2 | VH | HDVGYCTDRTCAKWPEWLGV | WGQGTLVTVSS |
| F5 | VH | MTSNAFAFDY | WGQGTLVTVSS |
| F5B6H2 | VH | MTSNAVGFDY | WGQGTLVTVSS |

*Fig. 17A*

Anti-Her2

V_L Alignments

|  |  | FR1 | CDR1 |
|---|---|---|---|
| C6.5 | VL | QSVLTQPPSVSAAPGQKVTISC | SGSSSNIGNNYVS |
| G98A | VL | QSVLTQPPSVSAAPGQKVTISC | SGSSSNIGNNYVS |
| ML3-9 | VL | QSVLTQPPSVSAAPGQKVTISC | SGSSSNIGNNYVS |
| H3B1 | VL | QSVLTQPPSVSAAPGQKVTISC | SGSSSNIGNNYVS |
| B1D2 | VL | QSVLTQPPSVSAAPGQKVTISC | SGSSSNIGNNYVS |
| F5 | VL | QSVLTQPPSVSGAPGQRVTISC | TGSSSNIGAGYGVH |
| F5B6H2 | VL | QSVLTQPPSVSGAPGQRVTISC | TGRHSNIGLGYGVH |

|  |  | FR2 | CDR2 |
|---|---|---|---|
| C6.5 | VL | WYQQLPGTAPKLLIY | GHTNRPA |
| G98A | VL | WYQQLPGTAPKLLIY | GHTNRPA |
| ML3-9 | VL | WYQQLPGTAPKLLIY | DHTNRPA |
| H3B1 | VL | WYQQLPGTAPKLLIY | DHTNRPA |
| B1D2 | VL | WYQQLPGTAPKLLIY | DHTNRPA |
| F5 | VL | WYQQLPGTAPKLLIY | GNTNRPS |
| F5B6H2 | VL | WYQQLPGTAPKLLIY | GNTNRPS |

|  |  | FR3 |
|---|---|---|
| C6.5 | VL | GVPDRFSGSKSGTSASLAISGFRSEDEADYYC |
| G98A | VL | GVPDRFSGSKSGTSASLAISGFRSEDEADYYC |
| ML3-9 | VL | GVPDRFSGSKSGTSASLAISGFRSEDEADYYC |
| H3B1 | VL | GVPDRFSGSKSGTSASLAISGFRSEDEADYYC |
| B1D2 | VL | GVPDRFSGSKSGTSASLAISGFRSEDEADYYC |
| F5 | VL | GVPDRFSGFKSGTSASLAITGLQAEDEADYYC |
| F5B6H2 | VL | GVPDRFSGFKSGTSASLAITGLQAEDEADYYC |

|  |  | CDR3 | FR4 |
|---|---|---|---|
| C6.5 | VL | AAWDDSLSGWV | FGGGTKLTVL |
| G98A | VL | AAWDDSLSGWV | FGGGTKLTVL |
| ML3-9 | VL | ASWDYTLSGWV | FGGGTKLTVL |
| H3B1 | VL | ASWDYTLSGWV | FGGGTKLTVL |
| B1D2 | VL | ASWDYTLSGWV | FGGGTKLTVL |
| F5 | VL | QSYDSSLSGWV | FGGGTKLTVL |
| F5B6H2 | VL | QSYDRRTPGWV | FGGGTKLTVL |

*Fig. 17B*

Anti-Her3

V_H Alignments

```
              FR1                            CDR1      FR2
A5   VH   QVQLVQSGGGLVKPGGSLRLSCAASGFSFN    TYDMN    WVRQAPGKGLEWVS
B12  VH   QVQLVQSGGGLVQPGRSLRLSCAASGFTFD    DYAMH    WVRQAPGKGLEWVS
E12  VH   QVQLVESGGGVVQPGRSLRLSCAASGFTFS    DYYIH    WVRQAPGKGLEWMA
F4   VH   QVQLQESGGGLVKPGGSLRLSCAASGFTFS    SYAMS    WVRQAPGKGLEWVS
H3   VH   QVQLQESGGGLVKPGGSLRLSCAASGFTFS    SYWMS    WVRQAPGKGLEWVA

CDR2                      FR3
A5   VH   SISSSSSYIYYADSVKG        RFTISRDNAKNSLYLQMNSLRAEDTAVYYCAR
B12  VH   GISWNSGSIGYADSVKG        RFTISRDNAKNSLYLQMNSLRPEDTAVYYCAR
E12  VH   VISYDGNNKYYAASVKD        RFTISRDNSKNTVSLQMNSLRAEDTAVYYCAR
F4   VH   TISGSGGSTYYADSVKG        RFTISRDNSKNTLYLQMNSLRAEDTAVYYCAK
H3   VH   NINRDGSASYYVDSVKG        RFTISRDDAKNSLYLQMNSLRAEDTAVYYCAR

CDR3               FR4
A5   VH   DGVATTPFDY           WGQGTLVTVSS
B12  VH   DLGAKQWLEGFDY        WGQGTLVTVSS
E12  VH   DLYGDYALDY           WGQGTLVTVSS
F4   VH   GYSSSWSEVASGY        WGQGTLVTVSS
H3   VH   DRGVGYFDL            WGRGTLVTVSS
```

*Fig. 18A*

Anti-Her3

V<sub>L</sub> Alignments

|  |  | FR1 | CDR1 |
|---|---|---|---|
| A5 | VL | QSVLTQPPSVSGAPGQRVTISC | TGSSSNIGAGYDVH |
| B12 | VL | NFMLTQDPAVSVALGQTVRITC | QGDSLRSYYAS |
| E12 | VL | DIQMTQSPSTLSASLGDRVTITC | RASQSIGSWLA |
| F4 | VL | DIVMTQSPSSLSASVGDRVTITC | RASQGIRNDLG |
| H3 | VL | QSALTQPASVSGSPGQSITISC | TGTSSDVGGYNFVS |

|  |  | FR2 | CDR2 |
|---|---|---|---|
| A5 | VL | WYQQLPGTAPKLLIY | GNSNRPS |
| B12 | VL | WYQQKPGQAPVLVIY | GKNNRPS |
| E12 | VL | WYQQKPGKAPKLLIY | KASTLES |
| F4 | VL | WYQQKAGKAPKLLIY | AASSLQS |
| H3 | VL | WYQQHPGKAPKLMIY | DVSDRPS |

|  |  | FR3 |
|---|---|---|
| A5 | VL | GVPDRFSGSKSGTSASLAITGLQAEDEADYYC |
| B12 | VL | GIPDRFSGSTSGNSASLTITGAQAEDEADYYC |
| E12 | VL | GVPSRFTGSGSGTEFTLTISGLQPEDFATYYC |
| F4 | VL | GVPSRFSGSGSGTDFTLTISSLQPDDFATYFC |
| H3 | VL | GVSDRFSGSKSGNTASLIISGLQADDEADYYC |

|  |  | CDR3 | FR4 |
|---|---|---|---|
| A5 | VL | QSYDSSLSAL | FGGGTKLTVL |
| B12 | VL | NSRDSSGNHWV | FGGGTKVTVL |
| E12 | VL | QKLSSYPLT | FGGGTKVEIKR |
| F4 | VL | QQAHSFPPT | FGGGTKVEIKR |
| H3 | VL | SSYGSSSTHVI | FGGGTKVTVL |

*Fig. 18B*

Anti-Her4

V_H Alignments

|  |  | FR1 | CDR1 |
|---|---|---|---|
| B6 | VH | QVQLVESGGGVVQPGRSLRLSCAASGFTFS | SYGMH |

|  |  | CDR2 | FR2 |
|---|---|---|---|
| B6 | VH | VISYDGSNKYYADSVKG | WVRQAPGKGLEWVA |

|  |  | FR3 |
|---|---|---|
| B6 | VH | RFTISRDNSKNTLYLQMNSLRAEDTAVYYCAK |

|  |  | CDR3 | FR4 |
|---|---|---|---|
| B6 | VH | YPLN | WGQGTLVTVSS |

V_L Alignments

|  |  | FR1 | CDR1 |
|---|---|---|---|
| B6 | VL | QSALTQPASVSGSPGQSITISC | TGTSSDVGGYNYVS |

|  |  | FR2 | CDR2 |
|---|---|---|---|
| B6 | VL | WYQQHPGKAPKLMIY | EVSNRPS |

|  |  | FR3 |
|---|---|---|
| B6 | VL | GVSNRFSGSKSGNTASLTISGLQAEDEADYYC |

|  |  | CDR3 | FR4 |
|---|---|---|---|
| B6 | VL | NSYTSSSTWV | FGGGTKLTVL |

*Fig. 19*

SEQUENCE LISTING

<160> NUMBER OF SEQ ID NOS: 288

<210> SEQ ID NO 1
<211> LENGTH: 6
<212> TYPE: PRT
<213> ORGANISM: Artificial
<220> FEATURE:
<223> OTHER INFORMATION: Peptide linker.

<400> SEQUENCE: 1

His His His His His His
1               5

<210> SEQ ID NO 2
<211> LENGTH: 129
<212> TYPE: PRT

```
<213> ORGANISM: Artificial
<220> FEATURE:
<223> OTHER INFORMATION: Single chain antibody or single chain antibody
      domain

<400> SEQUENCE: 2

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ala Trp Val Arg Gln Met Pro Gly Lys Gly Leu Glu Tyr Met
        35                  40                  45

Gly Leu Ile Tyr Pro Gly Asp Ser Asp Thr Lys Tyr Ser Pro Ser Phe
    50                  55                  60

Gln Gly Gln Val Thr Ile Ser Val Asp Lys Ser Val Ser Thr Ala Tyr
65                  70                  75                  80

Leu Gln Trp Ser Ser Leu Lys Pro Ser Asp Ser Ala Val Tyr Phe Cys
                85                  90                  95

Ala Arg His Asp Val Gly Tyr Cys Ser Ser Ser Asn Cys Ala Lys Trp
            100                 105                 110

Pro Glu Tyr Phe Gln His Trp Gly Gln Gly Thr Leu Val Thr Val Ser
            115                 120                 125

Ser

<210> SEQ ID NO 3
<211> LENGTH: 129
<212> TYPE: PRT
<213> ORGANISM: Artificial
<220> FEATURE:
<223> OTHER INFORMATION: Single chain antibody or single chain antibody
      domain.

<400> SEQUENCE: 3

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ala Trp Val Arg Gln Met Pro Gly Lys Gly Leu Glu Tyr Met
        35                  40                  45

Gly Leu Ile Tyr Pro Gly Asp Ser Asp Thr Lys Tyr Ser Pro Ser Phe
    50                  55                  60

Gln Gly Gln Val Thr Ile Ser Val Asp Lys Ser Val Ser Thr Ala Tyr
65                  70                  75                  80

Leu Gln Trp Ser Ser Leu Lys Pro Ser Asp Ser Ala Val Tyr Phe Cys
                85                  90                  95

Ala Arg His Asp Val Ala Tyr Cys Ser Ser Ser Asn Cys Ala Lys Trp
            100                 105                 110

Pro Glu Tyr Phe Gln His Trp Gly Gln Gly Thr Leu Val Thr Val Ser
            115                 120                 125

Ser

<210> SEQ ID NO 4
<211> LENGTH: 129
<212> TYPE: PRT
<213> ORGANISM: Artificial
<220> FEATURE:
<223> OTHER INFORMATION: Single chain antibody or single chain antibody
      domain.

<400> SEQUENCE: 4
```

```
Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ala Trp Val Arg Gln Met Pro Gly Lys Gly Leu Glu Tyr Met
        35                  40                  45

Gly Leu Ile Tyr Pro Gly Asp Ser Asp Thr Lys Tyr Ser Pro Ser Phe
    50                  55                  60

Gln Gly Gln Val Thr Ile Ser Val Asp Lys Ser Val Ser Thr Ala Tyr
65                  70                  75                  80

Leu Gln Trp Ser Ser Leu Lys Pro Ser Asp Ser Ala Val Tyr Phe Cys
            85                  90                  95

Ala Arg His Asp Val Gly Tyr Cys Ser Ser Asn Cys Ala Lys Trp
            100                 105                 110

Pro Glu Tyr Phe Gln His Trp Gly Gln Gly Thr Leu Val Thr Val Ser
        115                 120                 125

Ser

<210> SEQ ID NO 5
<211> LENGTH: 129
<212> TYPE: PRT
<213> ORGANISM: Artificial
<220> FEATURE:
<223> OTHER INFORMATION: Single chain antibody or single chain antibody
      domain.

<400> SEQUENCE: 5

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ala Trp Val Arg Gln Met Pro Gly Lys Gly Leu Glu Tyr Met
        35                  40                  45

Gly Leu Ile Tyr Pro Gly Asp Ser Asp Thr Lys Tyr Ser Pro Ser Phe
    50                  55                  60

Gln Gly Gln Val Thr Ile Ser Val Asp Lys Ser Val Ser Thr Ala Tyr
65                  70                  75                  80

Leu Gln Trp Ser Ser Leu Lys Pro Ser Asp Ser Ala Val Tyr Phe Cys
            85                  90                  95

Ala Arg His Asp Val Gly Tyr Cys Thr Asp Arg Thr Cys Ala Lys Trp
            100                 105                 110

Pro Glu Tyr Phe Gln His Trp Gly Gln Gly Thr Leu Val Thr Val Ser
        115                 120                 125

Ser

<210> SEQ ID NO 6
<211> LENGTH: 129
<212> TYPE: PRT
<213> ORGANISM: Artificial
<220> FEATURE:
<223> OTHER INFORMATION: Single chain antibody or single chain antibody
      domain.

<400> SEQUENCE: 6

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30
```

```
Trp Ile Ala Trp Val Arg Gln Met Pro Gly Lys Gly Leu Glu Tyr Met
            35                  40                  45

Gly Leu Ile Tyr Pro Gly Asp Ser Asp Thr Lys Tyr Ser Pro Ser Phe
 50                  55                  60

Gln Gly Gln Val Thr Ile Ser Val Asp Lys Ser Val Ser Thr Ala Tyr
 65                  70                  75                  80

Leu Gln Trp Ser Ser Leu Lys Pro Ser Asp Ser Ala Val Tyr Phe Cys
                 85                  90                  95

Ala Arg His Asp Val Gly Tyr Cys Thr Asp Arg Thr Cys Ala Lys Trp
               100                 105                 110

Pro Glu Trp Leu Gly Val Trp Gly Gln Gly Thr Leu Val Thr Val Ser
             115                 120                 125

Ser
```

<210> SEQ ID NO 7
<211> LENGTH: 110
<212> TYPE: PRT
<213> ORGANISM: Artificial
<220> FEATURE:
<223> OTHER INFORMATION: Single chain antibody or single chain antibody
      domain.

<400> SEQUENCE: 7

```
Gln Ser Val Leu Thr Gln Pro Pro Ser Val Ser Ala Ala Pro Gly Gln
 1               5                  10                  15

Lys Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
            35                  40                  45

Ile Tyr Gly His Thr Asn Arg Pro Ala Gly Val Pro Asp Arg Phe Ser
 50                  55                  60

Gly Ser Lys Ser Gly Thr Ser Ala Ser Leu Ala Ile Ser Gly Phe Arg
 65                  70                  75                  80

Ser Glu Asp Glu Ala Asp Tyr Tyr Cys Ala Ala Trp Asp Asp Ser Leu
                 85                  90                  95

Ser Gly Trp Val Phe Gly Gly Gly Thr Lys Leu Thr Val Leu
               100                 105                 110
```

<210> SEQ ID NO 8
<211> LENGTH: 110
<212> TYPE: PRT
<213> ORGANISM: Artificial
<220> FEATURE:
<223> OTHER INFORMATION: Single chain antibody or single chain antibody
      domain.

<400> SEQUENCE: 8

```
Gln Ser Val Leu Thr Gln Pro Pro Ser Val Ser Ala Ala Pro Gly Gln
 1               5                  10                  15

Lys Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
            35                  40                  45

Ile Tyr Gly His Thr Asn Arg Pro Ala Gly Val Pro Asp Arg Phe Ser
 50                  55                  60

Gly Ser Lys Ser Gly Thr Ser Ala Ser Leu Ala Ile Ser Gly Phe Arg
 65                  70                  75                  80

Ser Glu Asp Glu Ala Asp Tyr Tyr Cys Ala Ala Trp Asp Asp Ser Leu
```

```
                        85                  90                  95

Ser Gly Trp Val Phe Gly Gly Gly Thr Lys Leu Thr Val Leu
                100                 105                 110

<210> SEQ ID NO 9
<211> LENGTH: 110
<212> TYPE: PRT
<213> ORGANISM: Artificial
<220> FEATURE:
<223> OTHER INFORMATION: Single chain antibody or single chain antibody
      domain.

<400> SEQUENCE: 9

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp His Thr Asn Arg Pro Ala Gly Val Pro Asp Arg Phe Ser
        50                  55                  60

Gly Ser Lys Ser Gly Thr Ser Ala Ser Leu Ala Ile Ser Gly Phe Arg
65                  70                  75                  80

Ser Glu Asp Glu Ala Asp Tyr Tyr Cys Ala Ser Trp Asp Tyr Thr Leu
                85                  90                  95

Ser Gly Trp Val Phe Gly Gly Gly Thr Lys Leu Thr Val Leu
                100                 105                 110

<210> SEQ ID NO 10
<211> LENGTH: 110
<212> TYPE: PRT
<213> ORGANISM: Artificial
<220> FEATURE:
<223> OTHER INFORMATION: Single chain antibody or single chain antibody
      domain.

<400> SEQUENCE: 10

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp His Thr Asn Arg Pro Ala Gly Val Pro Asp Arg Phe Ser
        50                  55                  60

Gly Ser Lys Ser Gly Thr Ser Ala Ser Leu Ala Ile Ser Gly Phe Arg
65                  70                  75                  80

Ser Glu Asp Glu Ala Asp Tyr Tyr Cys Ala Ser Trp Asp Tyr Thr Leu
                85                  90                  95

Ser Gly Trp Val Phe Gly Gly Gly Thr Lys Leu Thr Val Leu
                100                 105                 110

<210> SEQ ID NO 11
<211> LENGTH: 110
<212> TYPE: PRT
<213> ORGANISM: Artificial
<220> FEATURE:
<223> OTHER INFORMATION: Single chain antibody or single chain antibody
      domain.

<400> SEQUENCE: 11
```

```
Gln Ser Val Leu Thr Gln Pro Pro Ser Val Ala Ala Pro Gly Gln
1               5                   10                  15

Lys Val Thr Ile Ser Cys Ser Gly Ser Ser Asn Ile Gly Asn Asn
                20                  25                  30

Tyr Val Ser Trp Tyr Gln Gln Leu Pro Gly Thr Ala Pro Lys Leu Leu
                35                  40                  45

Ile Tyr Asp His Thr Asn Arg Pro Ala Gly Val Pro Asp Arg Phe Ser
50                  55                  60

Gly Ser Lys Ser Gly Thr Ser Ala Ser Leu Ala Ile Ser Gly Phe Arg
65                  70                  75                  80

Ser Glu Asp Glu Ala Asp Tyr Tyr Cys Ala Ser Trp Asp Tyr Thr Leu
                85                  90                  95

Ser Gly Trp Val Phe Gly Gly Gly Thr Lys Leu Thr Val Leu
            100                 105                 110

<210> SEQ ID NO 12
<211> LENGTH: 119
<212> TYPE: PRT
<213> ORGANISM: Artificial
<220> FEATURE:
<223> OTHER INFORMATION: Single chain antibody or single chain antibody
      domain.

<400> SEQUENCE: 12

Gln Val Gln Leu Val Gln Ser Gly Gly Gly Leu Val Lys Pro Gly Gly
1               5                   10                  15

Ser Leu Arg Leu Ser Cys Ala Ala Ser Gly Phe Ser Phe Asn Thr Tyr
                20                  25                  30

Asp Met Asn Trp Val Arg Gln Ala Pro Gly Lys Gly Leu Glu Trp Val
            35                  40                  45

Ser Ser Ile Ser Ser Ser Ser Tyr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Val Ala Thr Thr Pro Phe Asp Tyr Trp Gln Gly
            100                 105                 110

Thr Leu Val Thr Val Ser Ser
        115

<210> SEQ ID NO 13
<211> LENGTH: 122
<212> TYPE: PRT
<213> ORGANISM: Artificial
<220> FEATURE:
<223> OTHER INFORMATION: Single chain antibody or single chain antibody
      domain.

<400> SEQUENCE: 13

Gln Val Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Ser Trp Asn Ser Gly Ser Ile Gly Tyr Ala Asp Ser Val
50                  55                  60

Lys Gly Arg Phe Thr Ile Ser Arg Asp Asn Ala Lys Asn Ser Leu Tyr
```

```
                65                  70                  75                  80
Leu Gln Met Asn Ser Leu Arg Pro Glu Asp Thr Ala Val Tyr Tyr Cys
                        85                  90                  95

Ala Arg Asp Leu Gly Ala Lys Gln Trp Leu Glu Gly Phe Asp Tyr Trp
                100                 105                 110

Gly Gln Gly Thr Leu Val Thr Val Ser Ser
                115                 120
```

<210> SEQ ID NO 14
<211> LENGTH: 129
<212> TYPE: PRT
<213> ORGANISM: Artificial
<220> FEATURE:
<223> OTHER INFORMATION: Single chain antibody or single chain antibody
      domain.

<400> SEQUENCE: 14

```
Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Ala Trp Val Arg Gln Met Pro Gly Lys Gly Leu Glu Tyr Met
            35                  40                  45

Gly Leu Ile Tyr Pro Gly Asp Ser Asp Thr Lys Tyr Ser Pro Ser Phe
        50                  55                  60

Gln Gly Gln Val Thr Ile Ser Val Asp Lys Ser Val Ser Thr Ala Tyr
65                  70                  75                  80

Leu Gln Trp Ser Ser Leu Lys Pro Ser Asp Ser Ala Val Tyr Phe Cys
                    85                  90                  95

Ala Arg His Asp Val Gly Tyr Cys Thr Asp Arg Thr Cys Ala Lys Trp
                100                 105                 110

Pro Glu Trp Leu Gly Val Trp Gly Gln Gly Thr Leu Val Thr Val Ser
            115                 120                 125

Ser
```

<210> SEQ ID NO 15
<211> LENGTH: 129
<212> TYPE: PRT
<213> ORGANISM: Artificial
<220> FEATURE:
<223> OTHER INFORMATION: Single chain antibody or single chain antibody
      domain.

<400> SEQUENCE: 15

```
Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Ala Trp Val Arg Gln Met Pro Gly Lys Gly Leu Glu Tyr Met
            35                  40                  45

Gly Leu Ile Tyr Pro Gly Asp Ser Asp Thr Lys Tyr Ser Pro Ser Phe
        50                  55                  60

Gln Gly Gln Val Thr Ile Ser Val Asp Lys Ser Val Ser Thr Ala Tyr
65                  70                  75                  80

Leu Gln Trp Ser Ser Leu Lys Pro Ser Asp Ser Ala Val Tyr Phe Cys
                    85                  90                  95

Ala Arg His Asp Val Gly Tyr Cys Ser Ser Ser Asn Cys Ala Lys Trp
                100                 105                 110
```

-continued

```
Pro Glu Tyr Phe Gln His Trp Gly Gln Gly Thr Leu Val Thr Val Ser
            115                 120                 125
Ser

<210> SEQ ID NO 16
<211> LENGTH: 122
<212> TYPE: PRT
<213> ORGANISM: Artificial
<220> FEATURE:
<223> OTHER INFORMATION: Single chain antibody or single chain antibody
      domain.

<400> SEQUENCE: 16

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Tyr Ser Ser Ser Trp Ser Glu Val Ala Ser Gly Tyr Trp
            100                 105                 110

Gly Gln Gly Thr Leu Val Thr Val Ser Ser
        115                 120

<210> SEQ ID NO 17
<211> LENGTH: 119
<212> TYPE: PRT
<213> ORGANISM: Artificial
<220> FEATURE:
<223> OTHER INFORMATION: Single chain antibody or single chain antibody
      domain.

<400> SEQUENCE: 17

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Ala Met Ser Trp Val Arg Gln Ala Pro Gly Lys Gly Leu Glu Trp Val
        35                  40                  45

Ser Ala Ile Ser Gly Arg Gly Asp Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Ser Asn Ala Val Gly Phe Asp Tyr Trp Gly Gln Gly
            100                 105                 110

Thr Leu Val Thr Val Ser Ser
        115

<210> SEQ ID NO 18
<211> LENGTH: 118
<212> TYPE: PRT
<213> ORGANISM: Artificial
```

```
<220> FEATURE:
<223> OTHER INFORMATION: Single chain antibody or single chain antibody
      domain.

<400> SEQUENCE: 18

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Arg Asp Gly Ser Ala Ser Tyr Tyr Val Asp Ser Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Val Gly Tyr Phe Asp Leu Trp Gly Arg Gly Thr
            100                 105                 110

Leu Val Thr Val Ser Ser
            115

<210> SEQ ID NO 19
<211> LENGTH: 111
<212> TYPE: PRT
<213> ORGANISM: Artificial
<220> FEATURE:
<223> OTHER INFORMATION: Single chain antibody or single chain antibody
      domain.

<400> SEQUENCE: 19

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Ala Leu Phe Gly Gly Gly Thr Lys Leu Thr Val Leu Gly
            100                 105                 110

<210> SEQ ID NO 20
<211> LENGTH: 108
<212> TYPE: PRT
<213> ORGANISM: Artificial
<220> FEATURE:
<223> OTHER INFORMATION: Single chain antibody or single chain antibody
      domain.

<400> SEQUENCE: 20

Asn Phe Met Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
```

```
                    35                  40                  45
Gly Lys Asn Asn Arg Pro Ser Gly Ile Pro Asp Arg Phe Ser Gly Ser
 50                  55                  60

Thr Ser Gly Asn Ser Ala Ser Leu Thr Ile Thr Gly Ala Gln Ala Glu
 65                  70                  75                  80

Asp Glu Ala Asp Tyr Tyr Cys Asn Ser Arg Asp Ser Ser Gly Asn His
                 85                  90                  95

Trp Val Phe Gly Gly Thr Lys Val Thr Val Leu
                100                 105

<210> SEQ ID NO 21
<211> LENGTH: 110
<212> TYPE: PRT
<213> ORGANISM: Artificial
<220> FEATURE:
<223> OTHER INFORMATION: Single chain antibody or single chain antibody
      domain.

<400> SEQUENCE: 21

Gln Ser Val Leu Thr Gln Pro Pro Ser Val Ser Ala Ala Pro Gly Gln
 1               5                  10                  15

Lys Val Thr Ile Ser Cys Ser Gly Ser Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp His Thr Asn Arg Pro Ala Gly Val Pro Asp Arg Phe Ser
 50                  55                  60

Gly Ser Lys Ser Gly Thr Ser Ala Ser Leu Ala Ile Ser Gly Phe Arg
 65                  70                  75                  80

Ser Glu Asp Glu Ala Asp Tyr Tyr Cys Ala Ser Trp Asp Tyr Thr Leu
                 85                  90                  95

Ser Gly Trp Val Phe Gly Gly Gly Thr Lys Leu Thr Val Leu
                100                 105                 110

<210> SEQ ID NO 22
<211> LENGTH: 110
<212> TYPE: PRT
<213> ORGANISM: Artificial
<220> FEATURE:
<223> OTHER INFORMATION: Single chain antibody or single chain antibody
      domain.

<400> SEQUENCE: 22

Gln Ser Val Leu Thr Gln Pro Pro Ser Val Ser Ala Ala Pro Gly Gln
 1               5                  10                  15

Lys Val Thr Ile Ser Cys Ser Gly Ser Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp His Thr Asn Arg Pro Ala Gly Val Pro Asp Arg Phe Ser
 50                  55                  60

Gly Ser Lys Ser Gly Thr Ser Ala Ser Leu Ala Ile Ser Gly Phe Arg
 65                  70                  75                  80

Ser Glu Asp Glu Ala Asp Tyr Tyr Cys Ala Ser Trp Asp Tyr Thr Leu
                 85                  90                  95

Ser Gly Trp Val Phe Gly Gly Gly Thr Lys Leu Thr Val Leu
                100                 105                 110

<210> SEQ ID NO 23
```

```
<211> LENGTH: 108
<212> TYPE: PRT
<213> ORGANISM: Artificial
<220> FEATURE:
<223> OTHER INFORMATION: Single chain antibody or single chain antibody
      domain.

<400> SEQUENCE: 23

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
                20                  25                  30

Leu Gly Trp Tyr Gln Gln Lys Ala Gly Lys Ala Pro Lys Leu Leu Ile
            35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Asp Asp Phe Ala Thr Tyr Phe Cys Gln Gln Ala His Ser Phe Pro Pro
                85                  90                  95

Thr Phe Gly Gly Gly Thr Lys Val Glu Ile Lys Arg
            100                 105

<210> SEQ ID NO 24
<211> LENGTH: 112
<212> TYPE: PRT
<213> ORGANISM: Artificial
<220> FEATURE:
<223> OTHER INFORMATION: Single chain antibody or single chain antibody
      domain.

<400> SEQUENCE: 24

Gln Ser Val Leu Thr Gln Pro Pro Ser Val Ser Gly Ala Pro Gly Gln
1               5                   10                  15

Arg Val Thr Ile Ser Cys Thr Gly Arg His Ser Asn Ile Gly Leu Gly
                20                  25                  30

Tyr Gly Val His Trp Tyr Gln Gln Leu Pro Gly Thr Ala Pro Lys Leu
            35                  40                  45

Leu Ile Tyr Gly Asn Thr Asn Arg Pro Ser Gly Val Pro Asp Arg Phe
50                  55                  60

Ser Gly Phe Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Arg Arg
                85                  90                  95

Thr Pro Gly Trp Val Phe Gly Gly Gly Thr Lys Leu Thr Val Leu Gly
            100                 105                 110

<210> SEQ ID NO 25
<211> LENGTH: 111
<212> TYPE: PRT
<213> ORGANISM: Artificial
<220> FEATURE:
<223> OTHER INFORMATION: Single chain antibody or single chain antibody
      domain.

<400> SEQUENCE: 25

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Phe Val Ser Trp Tyr Gln Gln His Pro Gly Lys Ala Pro Lys Leu
```

```
                    35                  40                  45
Met Ile Tyr Asp Val Ser Asp Arg Pro Ser Gly Val Ser Asp Arg Phe
            50                  55                  60

Ser Gly Ser Lys Ser Gly Asn Thr Ala Ser Leu Ile Ile Ser Gly Leu
65                  70                  75                  80

Gln Ala Asp Asp Glu Ala Asp Tyr Tyr Cys Ser Ser Tyr Gly Ser Ser
                85                  90                  95

Ser Thr His Val Ile Phe Gly Gly Gly Thr Lys Val Thr Val Leu
            100                 105                 110

<210> SEQ ID NO 26
<211> LENGTH: 1604
<212> TYPE: DNA
<213> ORGANISM: Artificial
<220> FEATURE:
<223> OTHER INFORMATION: Single chain antibody or single chain antibody
      domain.

<400> SEQUENCE: 26
gccatggccc aggtgcagct ggtgcagtct gggggaggcc tggtcaagcc tggggggtcc      60
ctgagactat cctgtgcagc ctctggattc agcttcaaca cctatgacat gaactgggtc     120
cgccaggctc cagggaaggg gctggagtgg gtctcatcca ttagtagtag tagtagttac     180
atatactacg cagactcagt gaagggccga ttcaccatct ccagagacaa cgccaagaac     240
tcactgtatc tgcaaatgaa cagcctgaga gccgaggaca cggctgtgta ttactgtgcg     300
agagatgggg tggctacgac cccctttgac tactggggcc agggcaccct ggtcaccgtc     360
tcctcaggtg gaggcggttc aggcggaggt ggctctggcg gtggcggatc gcagtctgtg     420
ttgacgcagc caccctcagt gtctggggcc cagggcagag ggtcaccat ctcctgcact     480 gggagcagct ccaacatcgg ggcaggttat gatgtacact ggtaccagca gcttccagga     540
acagccccca aactcctcat ctatggtaac agcaatcgtc cctcaggggt ccctgaccga     600
ttctctggct ccaagtctgg cacctcagcc tccctggcca tcactgggct ccaggctgag     660
gatgaggctg attattactg ccagtcctat gacagcagcc tgagtgccct attcggcgga     720
gggaccaagc tgaccgtcct agggaattca ggtgctggta cttcaggttc aggtgcttca     780
ggtgaaggtt caggttcaaa gcttcaggtg cagctggtgc agtctggggc agaggtgaaa     840
aagcccgggg agtctctgaa gatctcctgt aagggttctg gatacagctt taccagctac     900
tggatcgcct gggtgcgcca gatgcccggg aaaggcctgg agtacatggg gctcatctat     960
cctggtgact ctgacaccaa atacagcccg tccttccaag ccaggtcac catctcagtc    1020 gacaagtccg tcagcactgc ctacttgcaa tggagcagtc tgaagccctc ggacagcgcc    1080
gtgtattttt gtgcgagaca tgacgtggga tattgcagta gttccaactg cgcaaagtgg    1140
cctgaatact ccagcattg gggccagggc accctggtca ccgtctcctc aggtggaggc    1200
ggttcaggcg gaggtggctc tggcggtggc ggatcgcagt ctgtgttgac gcagccgccc    1260
tcagtgtctg cggccccagg acagaaggtc accatctcct gctctggaag cagctccaac    1320
attgggaata attatgtatc ctggtaccag cagctcccag aacagccccc caaactcctc    1380
atctatgatc acaccaatcg gcccgcaggg gtccctgacc gattctctgg ctccaagtct    1440
ggcacctcag cctccctggc catcagtggg ttccggtccg aggatgaggc tgattattac    1500
tgtgcctcct gggactacac cctctcgggc tgggtgttcg gcggaggaac caagctgacc    1560
gtcctaggtc tcgagcacca ccaccaccac cactgagcgg ccgc                     1604
```

```
<210> SEQ ID NO 27
<211> LENGTH: 531
<212> TYPE: PRT
<213> ORGANISM: Artificial
<220> FEATURE:
<223> OTHER INFORMATION: Single chain antibody or single chain antibody
      domain.

<400> SEQUENCE: 27

Ala Met Ala Gln Val Gln Leu Val Gln Ser Gly Gly Gly Leu Val Lys
1               5                   10                  15

Pro Gly Gly Ser Leu Arg Leu Ser Cys Ala Ala Ser Gly Phe Ser Phe
            20                  25                  30

Asn Thr Tyr Asp Met Asn Trp Val Arg Gln Ala Pro Gly Lys Gly Leu
        35                  40                  45

Glu Trp Val Ser Ser Ile Ser Ser Ser Ser Tyr Ile Tyr Tyr Ala
    50                  55                  60

Asp Ser Val Lys Gly Arg Phe Thr Ile Ser Arg Asp Asn Ala Lys Asn
65                  70                  75                  80

Ser Leu Tyr Leu Gln Met Asn Ser Leu Arg Ala Glu Asp Thr Ala Val
                85                  90                  95

Tyr Tyr Cys Ala Arg Asp Gly Val Ala Thr Thr Pro Phe Asp Tyr Trp
            100                 105                 110

Gly Gln Gly Thr Leu Val Thr Val Ser Ser Gly Gly Gly Gly Ser Gly
        115                 120                 125

Gly Gly Ser Gly Gly Gly Ser Gln Ser Val Leu Thr Gln Pro
    130                 135                 140

Pro Ser Val Ser Gly Ala Pro Gly Gln Arg Val Thr Ile Ser Cys Thr
145                 150                 155                 160

Gly Ser Ser Ser Asn Ile Gly Ala Gly Tyr Asp Val His Trp Tyr Gln
                165                 170                 175

Gln Leu Pro Gly Thr Ala Pro Lys Leu Leu Ile Tyr Gly Asn Ser Asn
            180                 185                 190

Arg Pro Ser Gly Val Pro Asp Arg Phe Ser Gly Ser Lys Ser Gly Thr
        195                 200                 205

Ser Ala Ser Leu Ala Ile Thr Gly Leu Gln Ala Glu Asp Glu Ala Asp
    210                 215                 220

Tyr Tyr Cys Gln Ser Tyr Asp Ser Ser Leu Ser Ala Leu Phe Gly Gly
225                 230                 235                 240

Gly Thr Lys Leu Thr Val Leu Gly Asn Ser Gly Ala Gly Thr Ser Gly
                245                 250                 255

Ser Gly Ala Ser Gly Glu Gly Ser Gly Ser Lys Leu Gln Val Gln Leu
            260                 265                 270

Val Gln Ser Gly Ala Glu Val Lys Lys Pro Gly Glu Ser Leu Lys Ile
        275                 280                 285

Ser Cys Lys Gly Ser Gly Tyr Ser Phe Thr Ser Tyr Trp Ile Ala Trp
    290                 295                 300

Val Arg Gln Met Pro Gly Lys Gly Leu Glu Tyr Met Gly Leu Ile Tyr
305                 310                 315                 320

Pro Gly Asp Ser Asp Thr Lys Tyr Ser Pro Ser Phe Gln Gly Gln Val
                325                 330                 335

Thr Ile Ser Val Asp Lys Ser Val Ser Thr Ala Tyr Leu Gln Trp Ser
            340                 345                 350

Ser Leu Lys Pro Ser Asp Ser Ala Val Tyr Phe Cys Ala Arg His Asp
        355                 360                 365

Val Gly Tyr Cys Ser Ser Ser Asn Cys Ala Lys Trp Pro Glu Tyr Phe
```

```
                  370                 375                 380
Gln His Trp Gly Gln Gly Thr Leu Val Thr Val Ser Ser Gly Gly
385                 390                 395                 400

Gly Ser Gly Gly Gly Ser Gly Gly Gly Ser Gln Ser Val Leu
                405                 410                 415

Thr Gln Pro Pro Ser Val Ser Ala Ala Pro Gly Gln Lys Val Thr Ile
                420                 425                 430

Ser Cys Ser Gly Ser Ser Asn Ile Gly Asn Asn Tyr Val Ser Trp
                435                 440                 445

Tyr Gln Gln Leu Pro Gly Thr Ala Pro Lys Leu Leu Ile Tyr Asp His
                450                 455                 460

Thr Asn Arg Pro Ala Gly Val Pro Asp Arg Phe Ser Gly Ser Lys Ser
465                 470                 475                 480

Gly Thr Ser Ala Ser Leu Ala Ile Ser Gly Phe Arg Ser Glu Asp Glu
                485                 490                 495

Ala Asp Tyr Tyr Cys Ala Ser Trp Asp Tyr Thr Leu Ser Gly Trp Val
                500                 505                 510

Phe Gly Gly Gly Thr Lys Leu Thr Val Leu Gly Leu Glu His His His
        515                 520                 525

His His His
        530

<210> SEQ ID NO 28
<211> LENGTH: 1604
<212> TYPE: DNA
<213> ORGANISM: Artificial
<220> FEATURE:
<223> OTHER INFORMATION: Single chain antibody or single chain antibody
      domain.

<400> SEQUENCE: 28
gccatggccc aggtgcagct ggtgcagtct ggggggaggc tggtcaagcc tggggggtcc      60
ctgagactat cctgtgcagc ctctggattc agcttcaaca cctatgacat gaactgggtc    120
cgccaggctc cagggaaggg gctggagtgg gtctcatcca ttagtagtag tagtagttac    180
atatactacg cagactcagt gaagggccga ttcaccatct ccagagacaa cgccaagaac    240
tcactgtatc tgcaaatgaa cagcctgaga gccgaggaca cggctgtgta ttactgtgcg    300
agagatgggg tggctacgac ccctttgac tactggggcc agggcaccct ggtcaccgtc     360
tcctcaggtg gaggcggttc aggcggaggt ggctctggcg gtggcggatc gcagtctgtg    420
ttgacgcagc caccctcagt gtctggggcc ccagggcaga gggtcaccat ctcctgcact    480
gggagcagct ccaacatcgg gcaggttat gatgtacact ggtaccagca gcttccagga    540
acagccccca aactcctcat ctatggtaac agcaatcgtc cctcagggt ccctgaccga    600 ttctctggct ccaagtctgg cacctcagcc tccctggcca tcactgggct ccaggctgag    660
gatgaggctg attattactg ccagtcctat gacagcagcc tgagtgccct attcggcgga    720
gggaccaagc tgaccgtcct agggaattca ggtgctggta cttcaggttc aggtgcttca    780
ggtgaaggtt caggttcaaa gcttcaggtg cagctggtgc agtctggggc agaggtgaaa    840
aagcccgggg agtctctgaa gatcctcctgt aagggttctg gatacagctt taccagctac    900
tggatcgcct gggtgcgcca gatgcccggg aaaggcctgg agtacatggg gctcatctat    960
cctggtgact ctgacaccaa atacagcccg tccttccaag ccaggtcac catctcagtc    1020 gacaagtccg tcagcactgc ctacttgcaa tggagcagtc tgaagccctc ggacagcgcc   1080
gtgtattttt gtgcgagaca tgacgtggga tattgcagta gttccaactg cgcaaagtgg   1140
```

-continued

```
cctgaatact tccagcattg gggccagggc accctggtca ccgtctcctc aggtggaggc    1200
ggttcaggcg gaggtggctc tggcggtggc ggatcgcagt ctgtgttgac gcagccgccc    1260
tcagtgtctg cggccccagg acagaaggtc accatctcct gctctggaag cagctccaac    1320
attgggaata attatgtatc ctggtaccag cagctcccag gaacagcccc caaactcctc    1380
atctatgatc acaccaatcg gcccgcaggg gtccctgacc gattctctgg ctccaagtct    1440
ggcacctcag cctccctggc catcagtggg ttccggtccg aggatgaggc tgattattac    1500
tgtgcctcct gggactacac cctctcgggc tgggtgttcg gcggaggaac caagctgacc    1560
gtcctaggtc tcgagcacca ccaccaccac cactgagcgg ccgc                    1604
```

<210> SEQ ID NO 29
<211> LENGTH: 519
<212> TYPE: PRT
<213> ORGANISM: Artificial
<220> FEATURE:
<223> OTHER INFORMATION: Single chain antibody or single chain antibody
      domain.

<400> SEQUENCE: 29

```
Pro Trp Pro Arg Cys Ser Trp Cys Ser Leu Gly Glu Ala Trp Ser Ser
1               5                   10                  15

Leu Gly Gly Pro Asp Tyr Pro Val Gln Pro Leu Asp Ser Ala Ser Thr
            20                  25                  30

Pro Met Thr Thr Gly Ser Ala Ala Leu Gln Gly Arg Gly Trp Ser Gly
        35                  40                  45

Ser His Pro Leu Val Val Val Val Thr Tyr Thr Thr Gln Thr Gln
    50                  55                  60

Arg Ala Asp Ser Pro Ser Pro Glu Thr Thr Pro Arg Thr His Cys Ile
65                  70                  75                  80

Cys Lys Thr Ala Glu Pro Arg Thr Arg Leu Cys Ile Thr Val Arg Glu
                85                  90                  95

Met Gly Trp Leu Arg Pro Leu Thr Thr Gly Ala Ala Ala Pro Trp
            100                 105                 110

Ser Pro Ser Pro Gln Val Glu Ala Val Gln Ala Glu Val Ala Leu Ala
        115                 120                 125

Val Ala Asp Arg Ser Leu Cys Arg Ser His Pro Gln Cys Leu Gly Pro
    130                 135                 140

Gln Gly Arg Gly Ser Pro Ser Pro Ala Leu Gly Ala Ala Pro Thr Ser
145                 150                 155                 160

Gly Gln Val Met Met Tyr Thr Gly Thr Ser Ser Phe Gln Glu Gln Pro
                165                 170                 175

Pro Asn Ser Ser Ser Met Val Thr Ala Ile Val Pro Gln Gly Ser Leu
            180                 185                 190

Thr Asp Ser Leu Ala Pro Ser Leu Ala Pro Gln Pro Trp Pro Ser
        195                 200                 205

Leu Gly Ser Arg Leu Arg Met Arg Leu Ile Ile Thr Ala Ser Pro Met
    210                 215                 220

Thr Ala Ala Val Pro Tyr Ser Ala Glu Gly Pro Ser Pro Ser Gly Ile
225                 230                 235                 240

Gln Val Leu Val Leu Gln Val Gln Val Leu Gly Val Lys Val Gln Val
                245                 250                 255

Gln Ser Phe Arg Cys Ser Trp Cys Ser Leu Gly Gln Arg Lys Ser Pro
            260                 265                 270

Gly Ser Leu Arg Ser Pro Val Arg Val Leu Asp Thr Ala Leu Pro Ala
```

```
                275                 280                 285
Thr Gly Ser Pro Gly Cys Ala Arg Cys Pro Gly Lys Ala Trp Ser Thr
        290                 295                 300
Trp Gly Ser Ser Ile Leu Val Thr Leu Thr Pro Asn Thr Ala Arg Pro
305                 310                 315                 320
Ser Lys Ala Arg Ser Pro Ser Gln Ser Thr Ser Pro Ser Ala Leu Pro
                325                 330                 335
Thr Cys Asn Gly Ala Val Ser Pro Arg Thr Ala Pro Cys Ile Phe Val
            340                 345                 350
Arg Asp Met Thr Trp Asp Ile Ala Val Val Pro Thr Ala Gln Ser Gly
                355                 360                 365
Leu Asn Thr Ser Ser Ile Gly Ala Ala Pro Trp Ser Pro Ser Pro
        370                 375                 380
Gln Val Glu Ala Val Gln Ala Glu Val Ala Leu Ala Val Ala Asp Arg
385                 390                 395                 400
Ser Leu Cys Arg Ser Arg Pro Gln Cys Leu Arg Pro Gln Asp Arg Arg
                405                 410                 415
Ser Pro Ser Pro Ala Leu Glu Ala Ala Pro Thr Leu Gly Ile Ile Met
            420                 425                 430
Tyr Pro Gly Thr Ser Ser Ser Gln Glu Gln Pro Pro Asn Ser Ser Ser
                435                 440                 445
Met Ile Thr Pro Ile Gly Pro Gly Gly Ser Leu Thr Asp Ser Leu Ala
        450                 455                 460
Pro Ser Leu Ala Pro Gln Pro Pro Trp Pro Ser Val Gly Ser Gly Pro
465                 470                 475                 480
Arg Met Arg Leu Ile Ile Thr Val Pro Pro Gly Thr Thr Pro Ser Arg
                485                 490                 495
Ala Gly Cys Ser Ala Glu Glu Pro Ser Pro Ser Val Ser Ser Thr Thr
                500                 505                 510
Thr Thr Thr Thr Glu Ala Pro
            515

<210> SEQ ID NO 30
<211> LENGTH: 1604
<212> TYPE: DNA
<213> ORGANISM: Artificial
<220> FEATURE:
<223> OTHER INFORMATION: Single chain antibody or single chain antibody
      domain.

<400> SEQUENCE: 30
gccatggccc aggtgcagct ggtgcagtct gggggaggcc tggtcaagcc tgggggtcc     60 ctgagactat cctgtgcagc ctctggattc agcttcaaca cctatgacat gaactgggtc    120
cgccaggctc cagggaaggg gctggagtgg gtctcatcca ttagtagtag tagtagttac    180
atatactacg cagactcagt gaagggccga ttcaccatct ccagagacaa cgccaagaac    240
tcactgtatc tgcaaatgaa cagcctgaga gccgaggaca cggctgtgta ttactgtgcg    300
agagatgggg tggctacgac ccccttgac tactggggcc agggcaccct ggtcaccgtc    360
tcctcaggtg gaggcggttc aggcggaggt ggctctggcg gtggcggatc gcagtctgtg    420
ttgacgcagc caccctcagt gtctggggcc cagggcaga gggtcaccat ctcctgcact    480
gggagcagct ccaacatcgg ggcaggttat gatgtacact ggtaccagca gcttccagga    540
acagccccca aactcctcat ctatggtaac agcaatcgtc cctcagggt ccctgaccga    600 ttctctggct ccaagtctgg cacctcagcc tccctggcca tcactgggct ccaggctgag    660
```

```
gatgaggctg attattactg ccagtcctat gacagcagcc tgagtgccct attcggcgga    720
gggaccaagc tgaccgtcct agggaattca ggtgctggta cttcaggttc aggtgcttca    780
ggtgaaggtt caggttcaaa gcttcaggtg cagctggtgc agtctggggc agaggtgaaa    840
aagcccgggg agtctctgaa gatcctctgt aagggttctg gatacagctt taccagctac    900
tggatcgcct gggtgcgcca gatgcccggg aaaggcctgg agtacatggg gctcatctat    960
cctggtgact ctgacaccaa atacagcccg tccttccaag gccaggtcac catctcagtc   1020
gacaagtccg tcagcactgc ctacttgcaa tggagcagtc tgaagccctc ggacagcgcc   1080 gtgtatttt gtgcgagaca tgacgtggga tattgcagta gttccaactg cgcaaagtgg    1140
cctgaatact ccagcattg ggccagggc accctggtca ccgtctcctc aggtggaggc     1200
ggttcaggcg gaggtggctc tggcggtggc ggatcgcagt ctgtgttgac gcagccgccc   1260
tcagtgtctg cggccccagg acagaaggtc accatctcct gctctggaag cagctccaac   1320
attgggaata attatgtatc ctggtaccag cagctcccag gaacagcccc caaactcctc   1380
atctatgatc acaccaatcg gcccgcaggg gtccctgacc gattctctgg ctccaagtct   1440
ggcacctcag cctccctggc catcagtggg ttccggtccg aggatgaggc tgattattac   1500
tgtgcctcct gggactacac cctctcgggc tgggtgttcg gcggaggaac caagctgacc   1560
gtcctaggtc tcgagcacca ccaccaccac cactgagcgg ccgc                    1604
```

<210> SEQ ID NO 31
<211> LENGTH: 509
<212> TYPE: PRT
<213> ORGANISM: Artificial
<220> FEATURE:
<223> OTHER INFORMATION: Single chain antibody or single chain antibody
      domain.

<400> SEQUENCE: 31

```
Arg His Gly Pro Gly Ala Ala Gly Ala Val Trp Gly Arg Pro Gly Gln
1               5                   10                  15

Ala Trp Gly Val Pro Glu Thr Ile Leu Cys Ser Leu Trp Ile Gln Leu
            20                  25                  30

Gln His Leu His Glu Leu Gly Pro Pro Gly Ser Arg Glu Gly Ala Gly
        35                  40                  45

Val Gly Leu Ile His Leu His Ile Leu Arg Arg Leu Ser Glu Gly Pro
    50                  55                  60

Ile His His Leu Gln Arg Gln Arg Gln Glu Leu Thr Val Ser Ala Asn
65                  70                  75                  80

Glu Gln Pro Glu Ser Arg Gly His Gly Cys Val Leu Leu Cys Glu Arg
                85                  90                  95

Trp Gly Gly Tyr Asp Pro Leu Leu Gly Pro Gly His Pro Gly His
            100                 105                 110

Arg Leu Leu Arg Trp Arg Arg Phe Arg Arg Arg Trp Leu Trp Arg Trp
        115                 120                 125

Arg Ile Ala Val Cys Val Asp Ala Ala Thr Leu Ser Val Trp Gly Pro
    130                 135                 140

Arg Ala Glu Gly His His Leu Leu His Trp Glu Gln Leu Gln His Arg
145                 150                 155                 160

Gly Arg Leu Cys Thr Leu Val Pro Ala Ala Ser Arg Asn Ser Pro Gln
                165                 170                 175

Thr Pro His Leu Trp Gln Gln Ser Ser Leu Arg Gly Pro Pro Ile Leu
            180                 185                 190

Trp Leu Gln Val Trp His Leu Ser Leu Pro Gly His His Trp Ala Pro
```

```
            195                 200                 205
Gly Gly Gly Leu Leu Leu Pro Val Leu Gln Gln Pro Glu Cys Pro Ile
210                 215                 220

Arg Arg Arg Asp Gln Ala Asp Arg Pro Arg Glu Phe Arg Cys Trp Tyr
225                 230                 235                 240

Phe Arg Phe Arg Cys Phe Arg Arg Phe Arg Phe Lys Ala Ser Gly Ala
                245                 250                 255

Ala Gly Ala Val Trp Gly Arg Gly Glu Lys Ala Ala Gly Val Ser Glu
            260                 265                 270

Asp Leu Leu Gly Phe Trp Ile Gln Leu Tyr Gln Leu Leu Asp Arg Leu
        275                 280                 285

Gly Ala Pro Asp Ala Arg Glu Arg Pro Gly Val His Gly Ala His Leu
290                 295                 300

Ser Trp Leu His Gln Ile Gln Pro Val Leu Pro Arg Pro Gly His His
305                 310                 315                 320

Leu Ser Arg Gln Val Arg Gln His Cys Leu Leu Ala Met Glu Gln Ser
                325                 330                 335

Glu Ala Leu Gly Gln Arg Val Phe Leu Cys Glu Thr Arg Gly Ile
            340                 345                 350

Leu Gln Phe Gln Leu Arg Lys Val Ala Ile Leu Pro Ala Leu Gly Pro
        355                 360                 365

Gly His Pro Gly His Arg Leu Leu Arg Trp Arg Phe Arg Arg
370                 375                 380

Trp Leu Trp Arg Trp Arg Ile Ala Val Cys Val Asp Ala Ala Ala Leu
385                 390                 395                 400

Ser Val Cys Gly Pro Arg Thr Glu Gly His His Leu Leu Trp Lys
                405                 410                 415

Gln Leu Gln His Trp Glu Leu Cys Ile Leu Val Pro Ala Ala Pro Arg
            420                 425                 430

Asn Ser Pro Gln Thr Pro His Leu Ser His Gln Ser Ala Arg Arg Gly
        435                 440                 445

Pro Pro Ile Leu Trp Leu Gln Val Trp His Leu Ser Leu Pro Gly His
450                 455                 460

Gln Trp Val Pro Val Arg Gly Gly Leu Leu Leu Cys Leu Leu Gly Leu
465                 470                 475                 480

His Pro Leu Gly Leu Gly Val Arg Arg Arg Asn Gln Ala Asp Arg Pro
                485                 490                 495

Arg Ser Ala Ala Pro Pro Pro Pro Leu Ser Gly Arg
            500                 505

<210> SEQ ID NO 32
<211> LENGTH: 126
<212> TYPE: PRT
<213> ORGANISM: Artificial
<220> FEATURE:
<223> OTHER INFORMATION: Single chain antibody or single chain antibody
      domain.

<400> SEQUENCE: 32

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
```

```
                    50                  55                  60
Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Glu Gly Pro Tyr Cys Ser Ser Thr Ser Cys Tyr Gly Ala
            100                 105                 110

Phe Asp Ile Trp Gly Gln Gly Thr Leu Val Thr Val Ser Ser
        115                 120                 125

<210> SEQ ID NO 33
<211> LENGTH: 126
<212> TYPE: PRT
<213> ORGANISM: Artificial
<220> FEATURE:
<223> OTHER INFORMATION: Single chain antibody or single chain antibody
      domain.

<400> SEQUENCE: 33

Glu Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
             20                  25                  30

Ala Ile Ser Trp Val Arg Gln Ala Pro Gly Gln Gly Leu Glu Trp Met
         35                  40                  45

Gly Gly Ile Ile Pro Ile Phe Gly Thr Ala Asn Tyr Ala Gln Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Glu Gly Pro Tyr Cys Ser Ser Thr Ser Cys Tyr Gly Ala
            100                 105                 110

Phe Asp Ile Trp Gly Gln Gly Thr Leu Val Thr Val Ser Ser
        115                 120                 125

<210> SEQ ID NO 34
<211> LENGTH: 108
<212> TYPE: PRT
<213> ORGANISM: Artificial
<220> FEATURE:
<223> OTHER INFORMATION: Single chain antibody or single chain antibody
      domain.

<400> SEQUENCE: 34

Gln Ser Val Leu Thr Gln Asp Pro Ala Val Ser Val Ala Leu Gly Gln
 1               5                  10                  15

Thr Val Lys Ile Thr Cys Gln Gly Asp Ser Leu Arg Ser Tyr Phe Ala
             20                  25                  30

Ser Trp Tyr Gln Gln Lys Pro Gly Gln Ala Pro Thr Leu Val Met Tyr
         35                  40                  45

Ala Arg Asn Asp Arg Pro Ala Gly Val Pro Asp Arg Phe Ser Gly Ser
     50                  55                  60

Lys Ser Gly Thr Ser Ala Ser Leu Ala Ile Ser Gly Leu Gln Ser Glu
 65                  70                  75                  80

Asp Glu Ala Asp Tyr Tyr Cys Ala Ala Trp Asp Asp Ser Leu Asn Gly
                 85                  90                  95

Tyr Leu Phe Gly Ala Gly Thr Lys Leu Thr Val Leu
            100                 105
```

<210> SEQ ID NO 35
<211> LENGTH: 108
<212> TYPE: PRT
<213> ORGANISM: Artificial
<220> FEATURE:
<223> OTHER INFORMATION: Single chain antibody or single chain antibody
     domain.

<400> SEQUENCE: 35

Gln Ser Val Leu Thr Gln Asp Pro Ala Val Ser Val Ala Leu Gly Gln
1               5                   10                  15

Thr Val Lys Ile Thr Cys Gln Gly Asp Ser Leu Arg Ser Tyr Phe Ala
            20                  25                  30

Ser Trp Tyr Gln Gln Lys Pro Gly Gln Ala Pro Thr Leu Val Met Tyr
        35                  40                  45

Ala Arg Asn Asp Arg Pro Ala Gly Val Pro Asp Arg Phe Ser Gly Ser
    50                  55                  60

Lys Ser Gly Thr Ser Ala Ser Leu Ala Ile Ser Gly Leu Gln Ser Glu
65                  70                  75                  80

Asp Glu Ala Asp Tyr Tyr Cys Ala Ala Trp Asp Ser Leu Asn Gly
                85                  90                  95

Tyr Leu Phe Gly Ala Gly Thr Lys Leu Thr Val Leu
                100                 105

<210> SEQ ID NO 36
<211> LENGTH: 129
<212> TYPE: PRT
<213> ORGANISM: Artificial
<220> FEATURE:
<223> OTHER INFORMATION: Single chain antibody or single chain antibody
     domain.

<400> SEQUENCE: 36

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ala Trp Val Arg Gln Met Pro Gly Lys Gly Leu Glu Tyr Met
        35                  40                  45

Gly Leu Ile Tyr Pro Gly Asp Ser Asp Thr Lys Tyr Ser Pro Ser Phe
    50                  55                  60

Gln Gly Gln Val Thr Ile Ser Val Asp Lys Ser Val Ser Thr Ala Tyr
65                  70                  75                  80

Leu Gln Trp Ser Ser Leu Lys Pro Ser Asp Ser Ala Val Tyr Phe Cys
                85                  90                  95

Ala Arg His Asp Val Gly Tyr Cys Ser Ser Asn Cys Ala Lys Trp
                100                 105                 110

Pro Glu Tyr Phe Gln His Trp Gly Gln Gly Thr Leu Val Thr Val Ser
            115                 120                 125

Ser

<210> SEQ ID NO 37
<211> LENGTH: 129
<212> TYPE: PRT
<213> ORGANISM: Artificial
<220> FEATURE:
<223> OTHER INFORMATION: Single chain antibody or single chain antibody
     domain.

<400> SEQUENCE: 37

```
Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ala Trp Val Arg Gln Met Pro Gly Lys Gly Leu Glu Tyr Met
        35                  40                  45

Gly Leu Ile Tyr Pro Gly Asp Ser Asp Thr Lys Tyr Ser Pro Ser Phe
    50                  55                  60

Gln Gly Gln Val Thr Ile Ser Val Asp Lys Ser Val Ser Thr Ala Tyr
65                  70                  75                  80

Leu Gln Trp Ser Ser Leu Lys Pro Ser Asp Ser Ala Val Tyr Phe Cys
                85                  90                  95

Ala Arg His Asp Val Ala Tyr Cys Ser Ser Ser Asn Cys Ala Lys Trp
            100                 105                 110

Pro Glu Tyr Phe Gln His Trp Gly Gln Gly Thr Leu Val Thr Val Ser
        115                 120                 125

Ser

<210> SEQ ID NO 38
<211> LENGTH: 129
<212> TYPE: PRT
<213> ORGANISM: Artificial
<220> FEATURE:
<223> OTHER INFORMATION: Single chain antibody or single chain antibody
      domain.

<400> SEQUENCE: 38

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ala Trp Val Arg Gln Met Pro Gly Lys Gly Leu Glu Tyr Met
        35                  40                  45

Gly Leu Ile Tyr Pro Gly Asp Ser Asp Thr Lys Tyr Ser Pro Ser Phe
    50                  55                  60

Gln Gly Gln Val Thr Ile Ser Val Asp Lys Ser Val Ser Thr Ala Tyr
65                  70                  75                  80

Leu Gln Trp Ser Ser Leu Lys Pro Ser Asp Ser Ala Val Tyr Phe Cys
                85                  90                  95

Ala Arg His Asp Val Gly Tyr Cys Ser Ser Ser Asn Cys Ala Lys Trp
            100                 105                 110

Pro Glu Tyr Phe Gln His Trp Gly Gln Gly Thr Leu Val Thr Val Ser
        115                 120                 125

Ser

<210> SEQ ID NO 39
<211> LENGTH: 129
<212> TYPE: PRT
<213> ORGANISM: Artificial
<220> FEATURE:
<223> OTHER INFORMATION: Single chain antibody or single chain antibody
      domain.

<400> SEQUENCE: 39

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30
```

```
Trp Ile Ala Trp Val Arg Gln Met Pro Gly Lys Gly Leu Glu Tyr Met
            35                  40                  45

Gly Leu Ile Tyr Pro Gly Asp Ser Asp Thr Lys Tyr Ser Pro Ser Phe
 50                  55                  60

Gln Gly Gln Val Thr Ile Ser Val Asp Lys Ser Val Ser Thr Ala Tyr
 65                  70                  75                  80

Leu Gln Trp Ser Ser Leu Lys Pro Ser Asp Ser Ala Val Tyr Phe Cys
                 85                  90                  95

Ala Arg His Asp Val Gly Tyr Cys Thr Asp Arg Thr Cys Ala Lys Trp
                100                 105                 110

Pro Glu Tyr Phe Gln His Trp Gly Gln Gly Thr Leu Val Thr Val Ser
            115                 120                 125

Ser
```

<210> SEQ ID NO 40
<211> LENGTH: 129
<212> TYPE: PRT
<213> ORGANISM: Artificial
<220> FEATURE:
<223> OTHER INFORMATION: Single chain antibody or single chain antibody
      domain.

<400> SEQUENCE: 40

```
Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Ser Tyr
                20                  25                  30

Trp Ile Ala Trp Val Arg Gln Met Pro Gly Lys Gly Leu Glu Tyr Met
            35                  40                  45

Gly Leu Ile Tyr Pro Gly Asp Ser Asp Thr Lys Tyr Ser Pro Ser Phe
 50                  55                  60

Gln Gly Gln Val Thr Ile Ser Val Asp Lys Ser Val Ser Thr Ala Tyr
 65                  70                  75                  80

Leu Gln Trp Ser Ser Leu Lys Pro Ser Asp Ser Ala Val Tyr Phe Cys
                 85                  90                  95

Ala Arg His Asp Val Gly Tyr Cys Thr Asp Arg Thr Cys Ala Lys Trp
                100                 105                 110

Pro Glu Trp Leu Gly Val Trp Gly Gln Gly Thr Leu Val Thr Val Ser
            115                 120                 125

Ser
```

<210> SEQ ID NO 41
<211> LENGTH: 119
<212> TYPE: PRT
<213> ORGANISM: Artificial
<220> FEATURE:
<223> OTHER INFORMATION: Single chain antibody or single chain antibody
      domain.

<400> SEQUENCE: 41

```
Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Arg Ser Tyr
                20                  25                  30

Ala Met Ser Trp Val Arg Gln Ala Pro Gly Lys Gly Leu Glu Trp Val
            35                  40                  45

Ser Ala Ile Ser Gly Arg Gly Asp Asn Thr Tyr Tyr Ala Asp Ser Val
 50                  55                  60
```

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Met Thr Ser Asn Ala Phe Ala Phe Asp Tyr Trp Gly Gln Gly
            100                 105                 110

Thr Leu Val Thr Val Ser Ser
        115

<210> SEQ ID NO 42
<211> LENGTH: 119
<212> TYPE: PRT
<213> ORGANISM: Artificial
<220> FEATURE:
<223> OTHER INFORMATION: Single chain antibody or single chain antibody
      domain.

<400> SEQUENCE: 42

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Ala Met Ser Trp Val Arg Gln Ala Pro Gly Lys Gly Leu Glu Trp Val
        35                  40                  45

Ser Ala Ile Ser Gly Arg Gly Asp Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Met Thr Ser Asn Ala Val Gly Phe Asp Tyr Trp Gly Gln Gly
            100                 105                 110

Thr Leu Val Thr Val Ser Ser
        115

<210> SEQ ID NO 43
<211> LENGTH: 110
<212> TYPE: PRT
<213> ORGANISM: Artificial
<220> FEATURE:
<223> OTHER INFORMATION: Single chain antibody or single chain antibody
      domain.

<400> SEQUENCE: 43

Gln Ser Val Leu Thr Gln Pro Pro Ser Val Ser Ala Ala Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Gly His Thr Asn Arg Pro Ala Gly Val Pro Asp Arg Phe Ser
    50                  55                  60

Gly Ser Lys Ser Gly Thr Ser Ala Ser Leu Ala Ile Ser Gly Phe Arg
65                  70                  75                  80

Ser Glu Asp Glu Ala Asp Tyr Tyr Cys Ala Ala Trp Asp Asp Ser Leu
                85                  90                  95

Ser Gly Trp Val Phe Gly Gly Gly Thr Lys Leu Thr Val Leu
            100                 105                 110

```
<210> SEQ ID NO 44
<211> LENGTH: 110
<212> TYPE: PRT
<213> ORGANISM: Artificial
<220> FEATURE:
<223> OTHER INFORMATION: Single chain antibody or single chain antibody
      domain.

<400> SEQUENCE: 44

Gln Ser Val Leu Thr Gln Pro Pro Ser Val Ser Ala Ala Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
            35                  40                  45

Ile Tyr Gly His Thr Asn Arg Pro Ala Gly Val Pro Asp Arg Phe Ser
        50                  55                  60

Gly Ser Lys Ser Gly Thr Ser Ala Ser Leu Ala Ile Ser Gly Phe Arg
65                  70                  75                  80

Ser Glu Asp Glu Ala Asp Tyr Tyr Cys Ala Ala Trp Asp Asp Ser Leu
                85                  90                  95

Ser Gly Trp Val Phe Gly Gly Gly Thr Lys Leu Thr Val Leu
            100                 105                 110

<210> SEQ ID NO 45
<211> LENGTH: 110
<212> TYPE: PRT
<213> ORGANISM: Artificial
<220> FEATURE:
<223> OTHER INFORMATION: Single chain antibody or single chain antibody
      domain.

<400> SEQUENCE: 45

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
            35                  40                  45

Ile Tyr Asp His Thr Asn Arg Pro Ala Gly Val Pro Asp Arg Phe Ser
        50                  55                  60

Gly Ser Lys Ser Gly Thr Ser Ala Ser Leu Ala Ile Ser Gly Phe Arg
65                  70                  75                  80

Ser Glu Asp Glu Ala Asp Tyr Tyr Cys Ala Ser Trp Asp Tyr Thr Leu
                85                  90                  95

Ser Gly Trp Val Phe Gly Gly Gly Thr Lys Leu Thr Val Leu
            100                 105                 110

<210> SEQ ID NO 46
<211> LENGTH: 110
<212> TYPE: PRT
<213> ORGANISM: Artificial
<220> FEATURE:
<223> OTHER INFORMATION: Single chain antibody or single chain antibody
      domain.

<400> SEQUENCE: 46

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30
```

Tyr Val Ser Trp Tyr Gln Gln Leu Pro Gly Thr Ala Pro Lys Leu Leu
            35                  40                  45

Ile Tyr Asp His Thr Asn Arg Pro Ala Gly Val Pro Asp Arg Phe Ser
 50                  55                  60

Gly Ser Lys Ser Gly Thr Ser Ala Ser Leu Ala Ile Ser Gly Phe Arg
 65                  70                  75                  80

Ser Glu Asp Glu Ala Asp Tyr Tyr Cys Ala Ser Trp Asp Tyr Thr Leu
                 85                  90                  95

Ser Gly Trp Val Phe Gly Gly Gly Thr Lys Leu Thr Val Leu
             100                 105                 110

<210> SEQ ID NO 47
<211> LENGTH: 110
<212> TYPE: PRT
<213> ORGANISM: Artificial
<220> FEATURE:
<223> OTHER INFORMATION: Single chain antibody or single chain antibody
      domain.

<400> SEQUENCE: 47

Gln Ser Val Leu Thr Gln Pro Pro Ser Val Ser Ala Ala Pro Gly Gln
 1               5                  10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
            35                  40                  45

Ile Tyr Asp His Thr Asn Arg Pro Ala Gly Val Pro Asp Arg Phe Ser
 50                  55                  60

Gly Ser Lys Ser Gly Thr Ser Ala Ser Leu Ala Ile Ser Gly Phe Arg
 65                  70                  75                  80

Ser Glu Asp Glu Ala Asp Tyr Tyr Cys Ala Ser Trp Asp Tyr Thr Leu
                 85                  90                  95

Ser Gly Trp Val Phe Gly Gly Gly Thr Lys Leu Thr Val Leu
             100                 105                 110

<210> SEQ ID NO 48
<211> LENGTH: 111
<212> TYPE: PRT
<213> ORGANISM: Artificial
<220> FEATURE:
<223> OTHER INFORMATION: Single chain antibody or single chain antibody
      domain.

<400> SEQUENCE: 48

Gln Ser Val Leu Thr Gln Pro Pro Ser Val Ser Gly Ala Pro Gly Gln
 1               5                  10                  15

Arg Val Thr Ile Ser Cys Thr Gly Ser Ser Ser Asn Ile Gly Ala Gly
            20                  25                  30

Tyr Gly Val His Trp Tyr Gln Gln Leu Pro Gly Thr Ala Pro Lys Leu
            35                  40                  45

Leu Ile Tyr Gly Asn Thr Asn Arg Pro Ser Gly Val Pro Asp Arg Phe
 50                  55                  60

Ser Gly Phe Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Ser
                 85                  90                  95

Leu Ser Gly Trp Val Phe Gly Gly Gly Thr Lys Leu Thr Val Leu
             100                 105                 110

-continued

```
<210> SEQ ID NO 49
<211> LENGTH: 112
<212> TYPE: PRT
<213> ORGANISM: Artificial
<220> FEATURE:
<223> OTHER INFORMATION: Single chain antibody or single chain antibody
      domain.

<400> SEQUENCE: 49

Gln Ser Val Leu Thr Gln Pro Pro Ser Val Ser Gly Ala Pro Gly Gln
1               5                   10                  15

Arg Val Thr Ile Ser Cys Thr Gly Arg His Ser Asn Ile Gly Leu Gly
            20                  25                  30

Tyr Gly Val His Trp Tyr Gln Gln Leu Pro Gly Thr Ala Pro Lys Leu
        35                  40                  45

Leu Ile Tyr Gly Asn Thr Asn Arg Pro Ser Gly Val Pro Asp Arg Phe
    50                  55                  60

Ser Gly Phe Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Arg Arg
                85                  90                  95

Thr Pro Gly Trp Val Phe Gly Gly Gly Thr Lys Leu Thr Val Leu Gly
            100                 105                 110

<210> SEQ ID NO 50
<211> LENGTH: 119
<212> TYPE: PRT
<213> ORGANISM: Artificial
<220> FEATURE:
<223> OTHER INFORMATION: Single chain antibody or single chain antibody
      domain.

<400> SEQUENCE: 50

Gln Val Gln Leu Val Gln Ser Gly Gly Gly Leu Val Lys Pro Gly Gly
1               5                   10                  15

Ser Leu Arg Leu Ser Cys Ala Ala Ser Gly Phe Ser Phe Asn Thr Tyr
            20                  25                  30

Asp Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Val Ala Thr Thr Pro Phe Asp Tyr Trp Gly Gln Gly
            100                 105                 110

Thr Leu Val Thr Val Ser Ser
        115

<210> SEQ ID NO 51
<211> LENGTH: 122
<212> TYPE: PRT
<213> ORGANISM: Artificial
<220> FEATURE:
<223> OTHER INFORMATION: Single chain antibody or single chain antibody
      domain.

<400> SEQUENCE: 51

Gln Val Gln Leu Val Gln Ser Gly Gly Gly Leu Val Gln Pro Gly Arg
1               5                   10                  15
```

```
Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Pro Glu Asp Thr Ala Val Tyr Tyr Cys
                85                  90                  95

Ala Arg Asp Leu Gly Ala Lys Gln Trp Leu Glu Gly Phe Asp Tyr Trp
            100                 105                 110

Gly Gln Gly Thr Leu Val Thr Val Ser Ser
            115                 120

<210> SEQ ID NO 52
<211> LENGTH: 119
<212> TYPE: PRT
<213> ORGANISM: Artificial
<220> FEATURE:
<223> OTHER INFORMATION: Single chain antibody or single chain antibody
      domain.

<400> SEQUENCE: 52

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Asp Tyr
            20                  25                  30

Tyr Ile His Trp Val Arg Gln Ala Pro Gly Lys Gly Leu Glu Trp Met
        35                  40                  45

Ala Val Ile Ser Tyr Asp Gly Asn Asn Lys Tyr Tyr Ala Ala Ser Val
 50                  55                  60

Lys Asp Arg Phe Thr Ile Ser Arg Asp Asn Ser Lys Asn Thr Val Ser
 65                  70                  75                  80

Leu Gln Met Asn Ser Leu Arg Ala Glu Asp Thr Ala Val Tyr Tyr Cys
                85                  90                  95

Ala Arg Asp Leu Tyr Gly Asp Tyr Ala Leu Asp Tyr Trp Gly Gln Gly
            100                 105                 110

Thr Leu Val Thr Val Ser Ser
            115

<210> SEQ ID NO 53
<211> LENGTH: 122
<212> TYPE: PRT
<213> ORGANISM: Artificial
<220> FEATURE:
<223> OTHER INFORMATION: Single chain antibody or single chain antibody
      domain.

<400> SEQUENCE: 53

Gln Val Gln Leu Gln Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Gly Ser Gly Gly Ser Thr Tyr Tyr Ala Asp Ser Val
 50                  55                  60
```

-continued

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Lys Gly Tyr Ser Ser Ser Trp Ser Glu Val Ala Ser Gly Tyr Trp
            100                 105                 110

Gly Gln Gly Thr Leu Val Thr Val Ser Ser
        115                 120

<210> SEQ ID NO 54
<211> LENGTH: 118
<212> TYPE: PRT
<213> ORGANISM: Artificial
<220> FEATURE:
<223> OTHER INFORMATION: Single chain antibody or single chain antibody
      domain.

<400> SEQUENCE: 54

Gln Val Gln Leu Gln Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Arg Asp Gly Ser Ala Ser Tyr Tyr Val Asp Ser Val
 50                  55                  60

Lys Gly Arg Phe Thr Ile Ser Arg Asp Asp Ala Lys Asn Ser Leu Tyr
 65                  70                  75                  80

Leu Gln Met Asn Ser Leu Arg Ala Glu Asp Thr Ala Val Tyr Tyr Cys
             85                  90                  95

Ala Arg Asp Arg Gly Val Gly Tyr Phe Asp Leu Trp Gly Arg Gly Thr
            100                 105                 110

Leu Val Thr Val Ser Ser
        115

<210> SEQ ID NO 55
<211> LENGTH: 111
<212> TYPE: PRT
<213> ORGANISM: Artificial
<220> FEATURE:
<223> OTHER INFORMATION: Single chain antibody or single chain antibody
      domain.

<400> SEQUENCE: 55

Gln Ser Val Leu Thr Gln Pro Pro Ser Val Ser Gly Ala Pro Gly Gln
 1               5                  10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
 50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Ser
             85                  90                  95

Leu Ser Ala Leu Phe Gly Gly Gly Thr Lys Leu Thr Val Leu Gly
            100                 105                 110

```
<210> SEQ ID NO 56
<211> LENGTH: 108
<212> TYPE: PRT
<213> ORGANISM: Artificial
<220> FEATURE:
<223> OTHER INFORMATION: Single chain antibody or single chain antibody
      domain.

<400> SEQUENCE: 56

Asn Phe Met Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Thr Ser Gly Asn Ser Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Trp Val Phe Gly Gly Gly Thr Lys Val Thr Val Leu
            100                 105

<210> SEQ ID NO 57
<211> LENGTH: 108
<212> TYPE: PRT
<213> ORGANISM: Artificial
<220> FEATURE:
<223> OTHER INFORMATION: Single chain antibody or single chain antibody
      domain.

<400> SEQUENCE: 57

Gln Ser Val Leu Thr Gln Asp Pro Ala Val Ser Val Ala Leu Gly Gln
1               5                   10                  15

Thr Val Lys Ile Thr Cys Gln Gly Asp Ser Leu Arg Ser Tyr Phe Ala
            20                  25                  30

Ser Trp Tyr Gln Gln Lys Pro Gly Gln Ala Pro Thr Leu Val Met Tyr
        35                  40                  45

Ala Arg Asn Asp Arg Pro Ala Gly Val Pro Asp Arg Phe Ser Gly Ser
    50                  55                  60

Lys Ser Gly Thr Ser Ala Ser Leu Ala Ile Ser Gly Leu Gln Ser Glu
65                  70                  75                  80

Asp Glu Ala Asp Tyr Tyr Cys Ala Ala Trp Asp Ser Leu Asn Gly
                85                  90                  95

Tyr Leu Phe Gly Ala Gly Thr Lys Leu Thr Val Leu
            100                 105

<210> SEQ ID NO 58
<211> LENGTH: 108
<212> TYPE: PRT
<213> ORGANISM: Artificial
<220> FEATURE:
<223> OTHER INFORMATION: Single chain antibody or single chain antibody
      domain.

<400> SEQUENCE: 58

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30
```

```
Leu Gly Trp Tyr Gln Gln Lys Ala Gly Lys Ala Pro Lys Leu Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Asp Asp Phe Ala Thr Tyr Phe Cys Gln Gln Ala His Ser Phe Pro Pro
                 85                  90                  95

Thr Phe Gly Gly Gly Thr Lys Val Glu Ile Lys Arg
                100                 105
```

<210> SEQ ID NO 59
<211> LENGTH: 111
<212> TYPE: PRT
<213> ORGANISM: Artificial
<220> FEATURE:
<223> OTHER INFORMATION: Single chain antibody or single chain antibody
      domain.

<400> SEQUENCE: 59

```
Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
                 20                  25                  30

Asn Phe Val Ser Trp Tyr Gln Gln His Pro Gly Lys Ala Pro Lys Leu
             35                  40                  45

Met Ile Tyr Asp Val Ser Asp Arg Pro Ser Gly Val Ser Asp Arg Phe
 50                  55                  60

Ser Gly Ser Lys Ser Gly Asn Thr Ala Ser Leu Ile Ile Ser Gly Leu
 65                  70                  75                  80

Gln Ala Asp Asp Glu Ala Asp Tyr Tyr Cys Ser Ser Tyr Gly Ser Ser
                 85                  90                  95

Ser Thr His Val Ile Phe Gly Gly Gly Thr Lys Val Thr Val Leu
                100                 105                 110
```

<210> SEQ ID NO 60
<211> LENGTH: 113
<212> TYPE: PRT
<213> ORGANISM: Artificial
<220> FEATURE:
<223> OTHER INFORMATION: Single chain antibody or single chain antibody
      domain.

<400> SEQUENCE: 60

```
Gln Val Gln Leu Val Glu Ser Gly Gly Val Val Gln Pro Gly Arg
 1               5                  10                  15

Ser Leu Arg Leu Ser Cys Ala Ala Ser Gly Phe Thr Phe Ser Ser Tyr
                 20                  25                  30

Gly Met His Val Ile Ser Tyr Asp Gly Ser Asn Lys Tyr Tyr Ala Asp
             35                  40                  45

Ser Val Lys Gly Trp Val Arg Gln Ala Pro Gly Lys Gly Leu Glu Trp
 50                  55                  60

Val Ala Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Tyr Pro Leu Asn Trp Gly Gln Gly Thr Leu Val Thr Val Ser
                100                 105                 110

Ser
```

```
<210> SEQ ID NO 61
<211> LENGTH: 110
<212> TYPE: PRT
<213> ORGANISM: Artificial
<220> FEATURE:
<223> OTHER INFORMATION: Single chain antibody or single chain antibody
      domain.

<400> SEQUENCE: 61

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Asn Ser Tyr Thr Ser Ser
                85                  90                  95

Ser Thr Trp Val Phe Gly Gly Gly Thr Lys Leu Thr Val Leu
            100                 105                 110

<210> SEQ ID NO 62
<211> LENGTH: 30
<212> TYPE: PRT
<213> ORGANISM: Artifical

<400> SEQUENCE: 62

Gln Val Gln Leu Val Gln Ser Gly Gly Gly Leu Val Lys Pro Gly Gly
1               5                   10                  15

Ser Leu Arg Leu Ser Cys Ala Ala Ser Gly Phe Ser Phe Asn
            20                  25                  30

<210> SEQ ID NO 63
<211> LENGTH: 5
<212> TYPE: PRT
<213> ORGANISM: Artifical

<400> SEQUENCE: 63

Thr Tyr Asp Met Asn
1               5

<210> SEQ ID NO 64
<211> LENGTH: 14
<212> TYPE: PRT
<213> ORGANISM: Artifical

<400> SEQUENCE: 64

Trp Val Arg Gln Ala Pro Gly Lys Gly Leu Glu Trp Val Ser
1               5                   10

<210> SEQ ID NO 65
<211> LENGTH: 17
<212> TYPE: PRT
<213> ORGANISM: Artifical

<400> SEQUENCE: 65

Ser Ile Ser Ser Ser Ser Ser Tyr Ile Tyr Tyr Ala Asp Ser Val Lys
1               5                   10                  15
```

Gly

<210> SEQ ID NO 66
<211> LENGTH: 32
<212> TYPE: PRT
<213> ORGANISM: Artifical

<400> SEQUENCE: 66

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 67
<211> LENGTH: 10
<212> TYPE: PRT
<213> ORGANISM: Artifical

<400> SEQUENCE: 67

Asp Gly Val Ala Thr Thr Pro Phe Asp Tyr
1               5                   10

<210> SEQ ID NO 68
<211> LENGTH: 11
<212> TYPE: PRT
<213> ORGANISM: Artifical

<400> SEQUENCE: 68

Trp Gly Gln Gly Thr Leu Val Thr Val Ser Ser
1               5                   10

<210> SEQ ID NO 69
<211> LENGTH: 30
<212> TYPE: PRT
<213> ORGANISM: Artifical

<400> SEQUENCE: 69

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg
            20                  25                  30

<210> SEQ ID NO 70
<211> LENGTH: 5
<212> TYPE: PRT
<213> ORGANISM: Artifical

<400> SEQUENCE: 70

Ser Tyr Ala Met Ser
1               5

<210> SEQ ID NO 71
<211> LENGTH: 14
<212> TYPE: PRT
<213> ORGANISM: Artifical

<400> SEQUENCE: 71

Trp Val Arg Gln Ala Pro Gly Lys Gly Leu Glu Trp Val Ser
1               5                   10

<210> SEQ ID NO 72
<211> LENGTH: 17
<212> TYPE: PRT
<213> ORGANISM: Artifical

```
<400> SEQUENCE: 72

Ala Ile Ser Gly Arg Gly Asp Asn Thr Tyr Tyr Ala Asp Ser Val Lys
1               5                   10                  15

Gly

<210> SEQ ID NO 73
<211> LENGTH: 32
<212> TYPE: PRT
<213> ORGANISM: Artifical

<400> SEQUENCE: 73

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Lys
            20                  25                  30

<210> SEQ ID NO 74
<211> LENGTH: 10
<212> TYPE: PRT
<213> ORGANISM: Artifical

<400> SEQUENCE: 74

Met Thr Ser Asn Ala Val Gly Phe Asp Tyr
1               5                   10

<210> SEQ ID NO 75
<211> LENGTH: 11
<212> TYPE: PRT
<213> ORGANISM: Artifical

<400> SEQUENCE: 75

Trp Gly Gln Gly Thr Leu Val Thr Val Ser Ser
1               5                   10

<210> SEQ ID NO 76
<211> LENGTH: 30
<212> TYPE: PRT
<213> ORGANISM: Artifical

<400> SEQUENCE: 76

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr
            20                  25                  30

<210> SEQ ID NO 77
<211> LENGTH: 5
<212> TYPE: PRT
<213> ORGANISM: Artifical

<400> SEQUENCE: 77

Ser Tyr Trp Ile Ala
1               5

<210> SEQ ID NO 78
<211> LENGTH: 14
<212> TYPE: PRT
<213> ORGANISM: Artifical

<400> SEQUENCE: 78

Trp Val Arg Gln Met Pro Gly Lys Gly Leu Glu Tyr Met Gly
1               5                   10
```

```
<210> SEQ ID NO 79
<211> LENGTH: 17
<212> TYPE: PRT
<213> ORGANISM: Artifical

<400> SEQUENCE: 79

Leu Ile Tyr Pro Gly Asp Ser Asp Thr Lys Tyr Ser Pro Ser Phe Gln
1               5                   10                  15

Gly

<210> SEQ ID NO 80
<211> LENGTH: 32
<212> TYPE: PRT
<213> ORGANISM: Artifical

<400> SEQUENCE: 80

Gln Val Thr Ile Ser Val Asp Lys Ser Val Ser Thr Ala Tyr Leu Gln
1               5                   10                  15

Trp Ser Ser Leu Lys Pro Ser Asp Ser Ala Val Tyr Phe Cys Ala Arg
            20                  25                  30

<210> SEQ ID NO 81
<211> LENGTH: 20
<212> TYPE: PRT
<213> ORGANISM: Artifical

<400> SEQUENCE: 81

His Asp Val Gly Tyr Cys Thr Asp Arg Thr Cys Ala Lys Trp Pro Glu
1               5                   10                  15

Trp Leu Gly Val
            20

<210> SEQ ID NO 82
<211> LENGTH: 11
<212> TYPE: PRT
<213> ORGANISM: Artifical

<400> SEQUENCE: 82

Trp Gly Gln Gly Thr Leu Val Thr Val Ser Ser
1               5                   10

<210> SEQ ID NO 83
<211> LENGTH: 30
<212> TYPE: PRT
<213> ORGANISM: Artifical

<400> SEQUENCE: 83

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr
            20                  25                  30

<210> SEQ ID NO 84
<211> LENGTH: 5
<212> TYPE: PRT
<213> ORGANISM: Artifical

<400> SEQUENCE: 84

Ser Tyr Trp Ile Ala
1               5

<210> SEQ ID NO 85
<211> LENGTH: 14
<212> TYPE: PRT
```

<213> ORGANISM: Artifical

<400> SEQUENCE: 85

Trp Val Arg Gln Met Pro Gly Lys Gly Leu Glu Tyr Met Gly
1               5                   10

<210> SEQ ID NO 86
<211> LENGTH: 17
<212> TYPE: PRT
<213> ORGANISM: Artifical

<400> SEQUENCE: 86

Leu Ile Tyr Pro Gly Asp Ser Asp Thr Lys Tyr Ser Pro Ser Phe Gln
1               5                   10                  15
Gly

<210> SEQ ID NO 87
<211> LENGTH: 32
<212> TYPE: PRT
<213> ORGANISM: Artifical

<400> SEQUENCE: 87

Gln Val Thr Ile Ser Val Asp Lys Ser Val Ser Thr Ala Tyr Leu Gln
1               5                   10                  15
Trp Ser Ser Leu Lys Pro Ser Asp Ser Ala Val Tyr Phe Cys Ala Arg
                20                  25                  30

<210> SEQ ID NO 88
<211> LENGTH: 20
<212> TYPE: PRT
<213> ORGANISM: Artifical

<400> SEQUENCE: 88

His Asp Val Gly Tyr Cys Ser Ser Ser Asn Cys Ala Lys Trp Pro Glu
1               5                   10                  15
Tyr Phe Gln His
                20

<210> SEQ ID NO 89
<211> LENGTH: 11
<212> TYPE: PRT
<213> ORGANISM: Artifical

<400> SEQUENCE: 89

Trp Gly Gln Gly Thr Leu Val Thr Val Ser Ser
1               5                   10

<210> SEQ ID NO 90
<211> LENGTH: 30
<212> TYPE: PRT
<213> ORGANISM: Artifical

<400> SEQUENCE: 90

Gln Val Gln Leu Val Gln Ser Gly Gly Gly Leu Val Gln Pro Gly Arg
1               5                   10                  15
Ser Leu Arg Leu Ser Cys Ala Ala Ser Gly Phe Thr Phe Asp
                20                  25                  30

<210> SEQ ID NO 91
<211> LENGTH: 5
<212> TYPE: PRT
<213> ORGANISM: Artifical

<400> SEQUENCE: 91

```
Asp Tyr Ala Met His
1               5
```

<210> SEQ ID NO 92
<211> LENGTH: 14
<212> TYPE: PRT
<213> ORGANISM: Artifical

<400> SEQUENCE: 92

```
Trp Val Arg Gln Ala Pro Gly Lys Gly Leu Glu Trp Val Ser
1               5                   10
```

<210> SEQ ID NO 93
<211> LENGTH: 17
<212> TYPE: PRT
<213> ORGANISM: Artifical

<400> SEQUENCE: 93

```
Gly Ile Ser Trp Asn Ser Gly Ser Ile Gly Tyr Ala Asp Ser Val Lys
1               5                   10                  15

Gly
```

<210> SEQ ID NO 94
<211> LENGTH: 32
<212> TYPE: PRT
<213> ORGANISM: Artifical

<400> SEQUENCE: 94

```
Arg Phe Thr Ile Ser Arg Asp Asn Ala Lys Asn Ser Leu Tyr Leu Gln
1               5                   10                  15

Met Asn Ser Leu Arg Pro Glu Asp Thr Ala Val Tyr Tyr Cys Ala Arg
            20                  25                  30
```

<210> SEQ ID NO 95
<211> LENGTH: 13
<212> TYPE: PRT
<213> ORGANISM: Artifical

<400> SEQUENCE: 95

```
Asp Leu Gly Ala Lys Gln Trp Leu Glu Gly Phe Asp Tyr
1               5                   10
```

<210> SEQ ID NO 96
<211> LENGTH: 11
<212> TYPE: PRT
<213> ORGANISM: Artifical

<400> SEQUENCE: 96

```
Trp Gly Gln Gly Thr Leu Val Thr Val Ser Ser
1               5                   10
```

<210> SEQ ID NO 97
<211> LENGTH: 30
<212> TYPE: PRT
<213> ORGANISM: Artifical

<400> SEQUENCE: 97

```
Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser
            20                  25                  30
```

<210> SEQ ID NO 98

```
<211> LENGTH: 5
<212> TYPE: PRT
<213> ORGANISM: Artifical

<400> SEQUENCE: 98

Ser Tyr Ala Met Ser
1               5

<210> SEQ ID NO 99
<211> LENGTH: 14
<212> TYPE: PRT
<213> ORGANISM: Artifical

<400> SEQUENCE: 99

Trp Val Arg Gln Ala Pro Gly Lys Gly Leu Glu Trp Val Ser
1               5                   10

<210> SEQ ID NO 100
<211> LENGTH: 17
<212> TYPE: PRT
<213> ORGANISM: Artifical

<400> SEQUENCE: 100

Thr Ile Ser Gly Ser Gly Gly Ser Thr Tyr Tyr Ala Asp Ser Val Lys
1               5                   10                  15

Gly

<210> SEQ ID NO 101
<211> LENGTH: 32
<212> TYPE: PRT
<213> ORGANISM: Artifical

<400> SEQUENCE: 101

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Lys
            20                  25                  30

<210> SEQ ID NO 102
<211> LENGTH: 13
<212> TYPE: PRT
<213> ORGANISM: Artifical

<400> SEQUENCE: 102

Gly Tyr Ser Ser Ser Trp Ser Glu Val Ala Ser Gly Tyr
1               5                   10

<210> SEQ ID NO 103
<211> LENGTH: 11
<212> TYPE: PRT
<213> ORGANISM: Artifical

<400> SEQUENCE: 103

Trp Gly Gln Gly Thr Leu Val Thr Val Ser Ser
1               5                   10

<210> SEQ ID NO 104
<211> LENGTH: 30
<212> TYPE: PRT
<213> ORGANISM: Artifical

<400> SEQUENCE: 104

Gln Val Gln Leu Gln Glu Ser Gly Gly Gly Leu Val Lys Pro Gly Gly
1               5                   10                  15
```

Ser Leu Arg Leu Ser Cys Ala Ala Ser Gly Phe Thr Phe Ser
            20                  25                  30

<210> SEQ ID NO 105
<211> LENGTH: 5
<212> TYPE: PRT
<213> ORGANISM: Artifical

<400> SEQUENCE: 105

Ser Tyr Trp Met Ser
1               5

<210> SEQ ID NO 106
<211> LENGTH: 14
<212> TYPE: PRT
<213> ORGANISM: Artifical

<400> SEQUENCE: 106

Trp Val Arg Gln Ala Pro Gly Lys Gly Leu Glu Trp Val Ala
1               5                   10

<210> SEQ ID NO 107
<211> LENGTH: 17
<212> TYPE: PRT
<213> ORGANISM: Artifical

<400> SEQUENCE: 107

Asn Ile Asn Arg Asp Gly Ser Ala Ser Tyr Tyr Val Asp Ser Val Lys
1               5                   10                  15

Gly

<210> SEQ ID NO 108
<211> LENGTH: 32
<212> TYPE: PRT
<213> ORGANISM: Artifical

<400> SEQUENCE: 108

Arg Phe Thr Ile Ser Arg Asp Asp Ala Lys Asn Ser Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 109
<211> LENGTH: 9
<212> TYPE: PRT
<213> ORGANISM: Artifical

<400> SEQUENCE: 109

Asp Arg Gly Val Gly Tyr Phe Asp Leu
1               5

<210> SEQ ID NO 110
<211> LENGTH: 11
<212> TYPE: PRT
<213> ORGANISM: Artifical

<400> SEQUENCE: 110

Trp Gly Arg Gly Thr Leu Val Thr Val Ser Ser
1               5                   10

<210> SEQ ID NO 111
<211> LENGTH: 30
<212> TYPE: PRT
<213> ORGANISM: Artifical

<400> SEQUENCE: 111

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr
            20                  25                  30

<210> SEQ ID NO 112
<211> LENGTH: 5
<212> TYPE: PRT
<213> ORGANISM: Artifical

<400> SEQUENCE: 112

Ser Tyr Trp Ile Ala
1               5

<210> SEQ ID NO 113
<211> LENGTH: 14
<212> TYPE: PRT
<213> ORGANISM: Artifical

<400> SEQUENCE: 113

Trp Val Arg Gln Met Pro Gly Lys Gly Leu Glu Tyr Met Gly
1               5                   10

<210> SEQ ID NO 114
<211> LENGTH: 17
<212> TYPE: PRT
<213> ORGANISM: Artifical

<400> SEQUENCE: 114

Leu Ile Tyr Pro Gly Asp Ser Asp Thr Lys Tyr Ser Pro Ser Phe Gln
1               5                   10                  15

Gly

<210> SEQ ID NO 115
<211> LENGTH: 32
<212> TYPE: PRT
<213> ORGANISM: Artifical

<400> SEQUENCE: 115

Gln Val Thr Ile Ser Val Asp Lys Ser Val Ser Thr Ala Tyr Leu Gln
1               5                   10                  15

Trp Ser Ser Leu Lys Pro Ser Asp Ser Ala Val Tyr Phe Cys Ala Arg
            20                  25                  30

<210> SEQ ID NO 116
<211> LENGTH: 20
<212> TYPE: PRT
<213> ORGANISM: Artifical

<400> SEQUENCE: 116

His Asp Val Gly Tyr Cys Ser Ser Ser Asn Cys Ala Lys Trp Pro Glu
1               5                   10                  15

Tyr Phe Gln His
            20

<210> SEQ ID NO 117
<211> LENGTH: 11
<212> TYPE: PRT
<213> ORGANISM: Artifical

<400> SEQUENCE: 117

Trp Gly Gln Gly Thr Leu Val Thr Val Ser Ser

-continued

<210> SEQ ID NO 118
<211> LENGTH: 30
<212> TYPE: PRT
<213> ORGANISM: Artifical

<400> SEQUENCE: 118

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr
            20                  25                  30

<210> SEQ ID NO 119
<211> LENGTH: 5
<212> TYPE: PRT
<213> ORGANISM: Artifical

<400> SEQUENCE: 119

Ser Tyr Trp Ile Ala
1               5

<210> SEQ ID NO 120
<211> LENGTH: 14
<212> TYPE: PRT
<213> ORGANISM: Artifical

<400> SEQUENCE: 120

Trp Val Arg Gln Met Pro Gly Lys Gly Leu Glu Tyr Met Gly
1               5                   10

<210> SEQ ID NO 121
<211> LENGTH: 17
<212> TYPE: PRT
<213> ORGANISM: Artifical

<400> SEQUENCE: 121

Leu Ile Tyr Pro Gly Asp Ser Asp Thr Lys Tyr Ser Pro Ser Phe Gln
1               5                   10                  15

Gly

<210> SEQ ID NO 122
<211> LENGTH: 32
<212> TYPE: PRT
<213> ORGANISM: Artifical

<400> SEQUENCE: 122

Gln Val Thr Ile Ser Val Asp Lys Ser Val Ser Thr Ala Tyr Leu Gln
1               5                   10                  15

Trp Ser Ser Leu Lys Pro Ser Asp Ser Ala Val Tyr Phe Cys Ala Arg
            20                  25                  30

<210> SEQ ID NO 123
<211> LENGTH: 20
<212> TYPE: PRT
<213> ORGANISM: Artifical

<400> SEQUENCE: 123

His Asp Val Gly Tyr Cys Thr Asp Arg Thr Cys Ala Lys Trp Pro Glu
1               5                   10                  15

Tyr Phe Gln His
            20

```
<210> SEQ ID NO 124
<211> LENGTH: 11
<212> TYPE: PRT
<213> ORGANISM: Artifical

<400> SEQUENCE: 124

Trp Gly Gln Gly Thr Leu Val Thr Val Ser Ser
1               5                   10

<210> SEQ ID NO 125
<211> LENGTH: 30
<212> TYPE: PRT
<213> ORGANISM: Artifical

<400> SEQUENCE: 125

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser
            20                  25                  30

<210> SEQ ID NO 126
<211> LENGTH: 5
<212> TYPE: PRT
<213> ORGANISM: Artifical

<400> SEQUENCE: 126

Ser Tyr Ala Ile Ser
1               5

<210> SEQ ID NO 127
<211> LENGTH: 14
<212> TYPE: PRT
<213> ORGANISM: Artifical

<400> SEQUENCE: 127

Trp Val Arg Gln Ala Pro Gly Gln Gly Leu Glu Trp Met Gly
1               5                   10

<210> SEQ ID NO 128
<211> LENGTH: 17
<212> TYPE: PRT
<213> ORGANISM: Artifical

<400> SEQUENCE: 128

Gly Ile Ile Pro Ile Phe Gly Thr Ala Asn Tyr Ala Gln Lys Phe Gln
1               5                   10                  15

Gly

<210> SEQ ID NO 129
<211> LENGTH: 32
<212> TYPE: PRT
<213> ORGANISM: Artifical

<400> SEQUENCE: 129

Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 130
<211> LENGTH: 17
<212> TYPE: PRT
<213> ORGANISM: Artifical

<400> SEQUENCE: 130
```

```
Glu Glu Gly Pro Tyr Cys Ser Ser Thr Ser Cys Tyr Gly Ala Phe Asp
1               5                   10                  15
Ile
```

<210> SEQ ID NO 131
<211> LENGTH: 11
<212> TYPE: PRT
<213> ORGANISM: Artifical

<400> SEQUENCE: 131

```
Trp Gly Gln Gly Thr Leu Val Thr Val Ser Ser
1               5                   10
```

<210> SEQ ID NO 132
<211> LENGTH: 30
<212> TYPE: PRT
<213> ORGANISM: Artifical

<400> SEQUENCE: 132

```
Glu Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser
            20                  25                  30
```

<210> SEQ ID NO 133
<211> LENGTH: 5
<212> TYPE: PRT
<213> ORGANISM: Artifical

<400> SEQUENCE: 133

```
Ser Tyr Ala Ile Ser
1               5
```

<210> SEQ ID NO 134
<211> LENGTH: 14
<212> TYPE: PRT
<213> ORGANISM: Artifical

<400> SEQUENCE: 134

```
Trp Val Arg Gln Ala Pro Gly Gln Gly Leu Glu Trp Met Gly
1               5                   10
```

<210> SEQ ID NO 135
<211> LENGTH: 17
<212> TYPE: PRT
<213> ORGANISM: Artifical

<400> SEQUENCE: 135

```
Gly Ile Ile Pro Ile Phe Gly Thr Ala Asn Tyr Ala Gln Lys Phe Gln
1               5                   10                  15
Gly
```

<210> SEQ ID NO 136
<211> LENGTH: 32
<212> TYPE: PRT
<213> ORGANISM: Artifical

<400> SEQUENCE: 136

```
Arg Val Thr Ile Thr Ala Asp Glu Ser Thr Ser Thr Ala Tyr Met Glu
1               5                   10                  15
Leu Ser Ser Leu Arg Ser Glu Asp Thr Ala Val Tyr Tyr Cys Ala Arg
            20                  25                  30
```

```
<210> SEQ ID NO 137
<211> LENGTH: 17
<212> TYPE: PRT
<213> ORGANISM: Artifical

<400> SEQUENCE: 137

Glu Glu Gly Pro Tyr Cys Ser Ser Thr Ser Cys Tyr Gly Ala Phe Asp
1               5                   10                  15
Ile

<210> SEQ ID NO 138
<211> LENGTH: 11
<212> TYPE: PRT
<213> ORGANISM: Artifical

<400> SEQUENCE: 138

Trp Gly Gln Gly Thr Leu Val Thr Val Ser Ser
1               5                   10

<210> SEQ ID NO 139
<211> LENGTH: 30
<212> TYPE: PRT
<213> ORGANISM: Artifical

<400> SEQUENCE: 139

Gln Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Arg
            20                  25                  30

<210> SEQ ID NO 140
<211> LENGTH: 5
<212> TYPE: PRT
<213> ORGANISM: Artifical

<400> SEQUENCE: 140

Ser Tyr Ala Met Ser
1               5

<210> SEQ ID NO 141
<211> LENGTH: 14
<212> TYPE: PRT
<213> ORGANISM: Artifical

<400> SEQUENCE: 141

Trp Val Arg Gln Ala Pro Gly Lys Gly Leu Glu Trp Val Ser
1               5                   10

<210> SEQ ID NO 142
<211> LENGTH: 17
<212> TYPE: PRT
<213> ORGANISM: Artifical

<400> SEQUENCE: 142

Ala Ile Ser Gly Arg Gly Asp Asn Thr Tyr Tyr Ala Asp Ser Val Lys
1               5                   10                  15
Gly

<210> SEQ ID NO 143
<211> LENGTH: 32
<212> TYPE: PRT
<213> ORGANISM: Artifical

<400> SEQUENCE: 143
```

```
Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Lys
                20                  25                  30
```

<210> SEQ ID NO 144
<211> LENGTH: 10
<212> TYPE: PRT
<213> ORGANISM: Artifical

<400> SEQUENCE: 144

```
Met Thr Ser Asn Ala Phe Ala Phe Asp Tyr
1               5                   10
```

<210> SEQ ID NO 145
<211> LENGTH: 11
<212> TYPE: PRT
<213> ORGANISM: Artifical

<400> SEQUENCE: 145

```
Trp Gly Gln Gly Thr Leu Val Thr Val Ser Ser
1               5                   10
```

<210> SEQ ID NO 146
<211> LENGTH: 30
<212> TYPE: PRT
<213> ORGANISM: Artifical

<400> SEQUENCE: 146

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser
                20                  25                  30
```

<210> SEQ ID NO 147
<211> LENGTH: 5
<212> TYPE: PRT
<213> ORGANISM: Artifical

<400> SEQUENCE: 147

```
Asp Tyr Tyr Ile His
1               5
```

<210> SEQ ID NO 148
<211> LENGTH: 14
<212> TYPE: PRT
<213> ORGANISM: Artifical

<400> SEQUENCE: 148

```
Trp Val Arg Gln Ala Pro Gly Lys Gly Leu Glu Trp Met Ala
1               5                   10
```

<210> SEQ ID NO 149
<211> LENGTH: 17
<212> TYPE: PRT
<213> ORGANISM: Artifical

<400> SEQUENCE: 149

```
Val Ile Ser Tyr Asp Gly Asn Asn Lys Tyr Tyr Ala Ala Ser Val Lys
1               5                   10                  15

Asp
```

<210> SEQ ID NO 150

<211> LENGTH: 32
<212> TYPE: PRT
<213> ORGANISM: Artifical

<400> SEQUENCE: 150

Arg Phe Thr Ile Ser Arg Asp Asn Ser Lys Asn Thr Val Ser Leu Gln
1               5                   10                  15

Met Asn Ser Leu Arg Ala Glu Asp Thr Ala Val Tyr Tyr Cys Ala Arg
            20                  25                  30

<210> SEQ ID NO 151
<211> LENGTH: 10
<212> TYPE: PRT
<213> ORGANISM: Artifical

<400> SEQUENCE: 151

Asp Leu Tyr Gly Asp Tyr Ala Leu Asp Tyr
1               5                   10

<210> SEQ ID NO 152
<211> LENGTH: 11
<212> TYPE: PRT
<213> ORGANISM: Artifical

<400> SEQUENCE: 152

Trp Gly Gln Gly Thr Leu Val Thr Val Ser Ser
1               5                   10

<210> SEQ ID NO 153
<211> LENGTH: 30
<212> TYPE: PRT
<213> ORGANISM: Artifical

<400> SEQUENCE: 153

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser
            20                  25                  30

<210> SEQ ID NO 154
<211> LENGTH: 5
<212> TYPE: PRT
<213> ORGANISM: Artifical

<400> SEQUENCE: 154

Ser Tyr Gly Met His
1               5

<210> SEQ ID NO 155
<211> LENGTH: 14
<212> TYPE: PRT
<213> ORGANISM: Artifical

<400> SEQUENCE: 155

Trp Val Arg Gln Ala Pro Gly Lys Gly Leu Glu Trp Val Ala
1               5                   10

<210> SEQ ID NO 156
<211> LENGTH: 17
<212> TYPE: PRT
<213> ORGANISM: Artifical

<400> SEQUENCE: 156

Val Ile Ser Tyr Asp Gly Ser Asn Lys Tyr Tyr Ala Asp Ser Val Lys
1               5                   10                  15

Gly

<210> SEQ ID NO 157
<211> LENGTH: 32
<212> TYPE: PRT
<213> ORGANISM: Artifical

<400> SEQUENCE: 157

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Lys
            20                  25                  30

<210> SEQ ID NO 158
<211> LENGTH: 4
<212> TYPE: PRT
<213> ORGANISM: Artifical

<400> SEQUENCE: 158

Tyr Pro Leu Asn
1

<210> SEQ ID NO 159
<211> LENGTH: 11
<212> TYPE: PRT
<213> ORGANISM: Artifical

<400> SEQUENCE: 159

Trp Gly Gln Gly Thr Leu Val Thr Val Ser Ser
1               5                   10

<210> SEQ ID NO 160
<211> LENGTH: 30
<212> TYPE: PRT
<213> ORGANISM: Artifical

<400> SEQUENCE: 160

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr
            20                  25                  30

<210> SEQ ID NO 161
<211> LENGTH: 5
<212> TYPE: PRT
<213> ORGANISM: Artifical

<400> SEQUENCE: 161

Ser Tyr Trp Ile Ala
1               5

<210> SEQ ID NO 162
<211> LENGTH: 14
<212> TYPE: PRT
<213> ORGANISM: Artifical

<400> SEQUENCE: 162

Trp Val Arg Gln Met Pro Gly Lys Gly Leu Glu Tyr Met Gly
1               5                   10

<210> SEQ ID NO 163
<211> LENGTH: 17
<212> TYPE: PRT
<213> ORGANISM: Artifical

```
<400> SEQUENCE: 163

Leu Ile Tyr Pro Gly Asp Ser Asp Thr Lys Tyr Ser Pro Ser Phe Gln
1               5                   10                  15

Gly

<210> SEQ ID NO 164
<211> LENGTH: 32
<212> TYPE: PRT
<213> ORGANISM: Artifical

<400> SEQUENCE: 164

Gln Val Thr Ile Ser Val Asp Lys Ser Val Ser Thr Ala Tyr Leu Gln
1               5                   10                  15

Trp Ser Ser Leu Lys Pro Ser Asp Ser Ala Val Tyr Phe Cys Ala Arg
            20                  25                  30

<210> SEQ ID NO 165
<211> LENGTH: 20
<212> TYPE: PRT
<213> ORGANISM: Artifical

<400> SEQUENCE: 165

His Asp Val Ala Tyr Cys Ser Ser Ser Asn Cys Ala Lys Trp Pro Glu
1               5                   10                  15

Tyr Phe Gln His
            20

<210> SEQ ID NO 166
<211> LENGTH: 11
<212> TYPE: PRT
<213> ORGANISM: Artifical

<400> SEQUENCE: 166

Trp Gly Gln Gly Thr Leu Val Thr Val Ser Ser
1               5                   10

<210> SEQ ID NO 167
<211> LENGTH: 22
<212> TYPE: PRT
<213> ORGANISM: Artifical

<400> SEQUENCE: 167

Gln Ser Val Leu Thr Gln Pro Pro Ser Val Ser Gly Ala Pro Gly Gln
1               5                   10                  15

Arg Val Thr Ile Ser Cys
            20

<210> SEQ ID NO 168
<211> LENGTH: 14
<212> TYPE: PRT
<213> ORGANISM: Artifical

<400> SEQUENCE: 168

Thr Gly Ser Ser Ser Asn Ile Gly Ala Gly Tyr Asp Val His
1               5                   10

<210> SEQ ID NO 169
<211> LENGTH: 15
<212> TYPE: PRT
<213> ORGANISM: Artifical

<400> SEQUENCE: 169
```

```
Trp Tyr Gln Gln Leu Pro Gly Thr Ala Pro Lys Leu Leu Ile Tyr
1               5                   10                  15
```

<210> SEQ ID NO 170
<211> LENGTH: 7
<212> TYPE: PRT
<213> ORGANISM: Artifical

<400> SEQUENCE: 170

```
Gly Asn Ser Asn Arg Pro Ser
1               5
```

<210> SEQ ID NO 171
<211> LENGTH: 32
<212> TYPE: PRT
<213> ORGANISM: Artifical

<400> SEQUENCE: 171

```
Gly Val Pro Asp Arg Phe Ser Gly Ser Lys Ser Gly Thr Ser Ala Ser
1               5                   10                  15

Leu Ala Ile Thr Gly Leu Gln Ala Glu Asp Glu Ala Asp Tyr Tyr Cys
                20                  25                  30
```

<210> SEQ ID NO 172
<211> LENGTH: 10
<212> TYPE: PRT
<213> ORGANISM: Artifical

<400> SEQUENCE: 172

```
Gln Ser Tyr Asp Ser Ser Leu Ser Ala Leu
1               5                   10
```

<210> SEQ ID NO 173
<211> LENGTH: 11
<212> TYPE: PRT
<213> ORGANISM: Artifical

<400> SEQUENCE: 173

```
Phe Gly Gly Gly Thr Lys Leu Thr Val Leu Gly
1               5                   10
```

<210> SEQ ID NO 174
<211> LENGTH: 22
<212> TYPE: PRT
<213> ORGANISM: Artifical

<400> SEQUENCE: 174

```
Gln Ser Val Leu Thr Gln Pro Pro Ser Val Ser Gly Ala Pro Gly Gln
1               5                   10                  15

Arg Val Thr Ile Ser Cys
                20
```

<210> SEQ ID NO 175
<211> LENGTH: 14
<212> TYPE: PRT
<213> ORGANISM: Artifical

<400> SEQUENCE: 175

```
Thr Gly Arg His Ser Asn Ile Gly Leu Gly Tyr Gly Val His
1               5                   10
```

<210> SEQ ID NO 176
<211> LENGTH: 15
<212> TYPE: PRT
<213> ORGANISM: Artifical

```
<400> SEQUENCE: 176

Trp Tyr Gln Gln Leu Pro Gly Thr Ala Pro Lys Leu Leu Ile Tyr
1               5                   10                  15

<210> SEQ ID NO 177
<211> LENGTH: 7
<212> TYPE: PRT
<213> ORGANISM: Artifical

<400> SEQUENCE: 177

Gly Asn Thr Asn Arg Pro Ser
1               5

<210> SEQ ID NO 178
<211> LENGTH: 32
<212> TYPE: PRT
<213> ORGANISM: Artifical

<400> SEQUENCE: 178

Gly Val Pro Asp Arg Phe Ser Gly Phe Lys Ser Gly Thr Ser Ala Ser
1               5                   10                  15

Leu Ala Ile Thr Gly Leu Gln Ala Glu Asp Glu Ala Asp Tyr Tyr Cys
            20                  25                  30

<210> SEQ ID NO 179
<211> LENGTH: 11
<212> TYPE: PRT
<213> ORGANISM: Artifical

<400> SEQUENCE: 179

Gln Ser Tyr Asp Arg Arg Thr Pro Gly Trp Val
1               5                   10

<210> SEQ ID NO 180
<211> LENGTH: 11
<212> TYPE: PRT
<213> ORGANISM: Artifical

<400> SEQUENCE: 180

Phe Gly Gly Gly Thr Lys Leu Thr Val Leu Gly
1               5                   10

<210> SEQ ID NO 181
<211> LENGTH: 22
<212> TYPE: PRT
<213> ORGANISM: Artifical

<400> SEQUENCE: 181

Gln Ser Val Leu Thr Gln Pro Pro Ser Val Ser Ala Ala Pro Gly Gln
1               5                   10                  15

Lys Val Thr Ile Ser Cys
            20

<210> SEQ ID NO 182
<211> LENGTH: 13
<212> TYPE: PRT
<213> ORGANISM: Artifical

<400> SEQUENCE: 182

Ser Gly Ser Ser Ser Asn Ile Gly Asn Asn Tyr Val Ser
1               5                   10

<210> SEQ ID NO 183
```

```
<211> LENGTH: 15
<212> TYPE: PRT
<213> ORGANISM: Artifical

<400> SEQUENCE: 183

Trp Tyr Gln Gln Leu Pro Gly Thr Ala Pro Lys Leu Leu Ile Tyr
1               5                   10                  15

<210> SEQ ID NO 184
<211> LENGTH: 7
<212> TYPE: PRT
<213> ORGANISM: Artifical

<400> SEQUENCE: 184

Asp His Thr Asn Arg Pro Ala
1               5

<210> SEQ ID NO 185
<211> LENGTH: 32
<212> TYPE: PRT
<213> ORGANISM: Artifical

<400> SEQUENCE: 185

Gly Val Pro Asp Arg Phe Ser Gly Ser Lys Ser Gly Thr Ser Ala Ser
1               5                   10                  15

Leu Ala Ile Ser Gly Phe Arg Ser Glu Asp Glu Ala Asp Tyr Tyr Cys
                20                  25                  30

<210> SEQ ID NO 186
<211> LENGTH: 11
<212> TYPE: PRT
<213> ORGANISM: Artifical

<400> SEQUENCE: 186

Ala Ser Trp Asp Tyr Thr Leu Ser Gly Trp Val
1               5                   10

<210> SEQ ID NO 187
<211> LENGTH: 10
<212> TYPE: PRT
<213> ORGANISM: Artifical

<400> SEQUENCE: 187

Phe Gly Gly Gly Thr Lys Leu Thr Val Leu
1               5                   10

<210> SEQ ID NO 188
<211> LENGTH: 22
<212> TYPE: PRT
<213> ORGANISM: Artifical

<400> SEQUENCE: 188

Gln Ser Val Leu Thr Gln Pro Pro Ser Val Ser Ala Ala Pro Gly Gln
1               5                   10                  15

Lys Val Thr Ile Ser Cys
                20

<210> SEQ ID NO 189
<211> LENGTH: 13
<212> TYPE: PRT
<213> ORGANISM: Artifical

<400> SEQUENCE: 189

Ser Gly Ser Ser Ser Asn Ile Gly Asn Asn Tyr Val Ser
1               5                   10
```

```
<210> SEQ ID NO 190
<211> LENGTH: 15
<212> TYPE: PRT
<213> ORGANISM: Artifical

<400> SEQUENCE: 190

Trp Tyr Gln Gln Leu Pro Gly Thr Ala Pro Lys Leu Leu Ile Tyr
1               5                   10                  15

<210> SEQ ID NO 191
<211> LENGTH: 7
<212> TYPE: PRT
<213> ORGANISM: Artifical

<400> SEQUENCE: 191

Asp His Thr Asn Arg Pro Ala
1               5

<210> SEQ ID NO 192
<211> LENGTH: 32
<212> TYPE: PRT
<213> ORGANISM: Artifical

<400> SEQUENCE: 192

Gly Val Pro Asp Arg Phe Ser Gly Ser Lys Ser Gly Thr Ser Ala Ser
1               5                   10                  15

Leu Ala Ile Ser Gly Phe Arg Ser Glu Asp Glu Ala Asp Tyr Tyr Cys
            20                  25                  30

<210> SEQ ID NO 193
<211> LENGTH: 11
<212> TYPE: PRT
<213> ORGANISM: Artifical

<400> SEQUENCE: 193

Ala Ser Trp Asp Tyr Thr Leu Ser Gly Trp Val
1               5                   10

<210> SEQ ID NO 194
<211> LENGTH: 10
<212> TYPE: PRT
<213> ORGANISM: Artifical

<400> SEQUENCE: 194

Phe Gly Gly Gly Thr Lys Leu Thr Val Leu
1               5                   10

<210> SEQ ID NO 195
<211> LENGTH: 22
<212> TYPE: PRT
<213> ORGANISM: Artifical

<400> SEQUENCE: 195

Asn Phe Met Leu Thr Gln Asp Pro Ala Val Ser Val Ala Leu Gly Gln
1               5                   10                  15

Thr Val Arg Ile Thr Cys
            20

<210> SEQ ID NO 196
<211> LENGTH: 11
<212> TYPE: PRT
<213> ORGANISM: Artifical

<400> SEQUENCE: 196
```

```
Gln Gly Asp Ser Leu Arg Ser Tyr Tyr Ala Ser
1               5                   10
```

```
<210> SEQ ID NO 197
<211> LENGTH: 15
<212> TYPE: PRT
<213> ORGANISM: Artifical

<400> SEQUENCE: 197

Trp Tyr Gln Gln Lys Pro Gly Gln Ala Pro Val Leu Val Ile Tyr
1               5                   10                  15
```

```
<210> SEQ ID NO 198
<211> LENGTH: 7
<212> TYPE: PRT
<213> ORGANISM: Artifical

<400> SEQUENCE: 198

Gly Lys Asn Asn Arg Pro Ser
1               5
```

```
<210> SEQ ID NO 199
<211> LENGTH: 32
<212> TYPE: PRT
<213> ORGANISM: Artifical

<400> SEQUENCE: 199

Gly Ile Pro Asp Arg Phe Ser Gly Ser Thr Ser Gly Asn Ser Ala Ser
1               5                   10                  15

Leu Thr Ile Thr Gly Ala Gln Ala Glu Asp Glu Ala Asp Tyr Tyr Cys
            20                  25                  30
```

```
<210> SEQ ID NO 200
<211> LENGTH: 11
<212> TYPE: PRT
<213> ORGANISM: Artifical

<400> SEQUENCE: 200

Asn Ser Arg Asp Ser Ser Gly Asn His Trp Val
1               5                   10
```

```
<210> SEQ ID NO 201
<211> LENGTH: 10
<212> TYPE: PRT
<213> ORGANISM: Artifical

<400> SEQUENCE: 201

Phe Gly Gly Gly Thr Lys Val Thr Val Leu
1               5                   10
```

```
<210> SEQ ID NO 202
<211> LENGTH: 23
<212> TYPE: PRT
<213> ORGANISM: Artifical

<400> SEQUENCE: 202

Asp Ile Val Met Thr Gln Ser Pro Ser Leu Ser Ala Ser Val Gly
1               5                   10                  15

Asp Arg Val Thr Ile Thr Cys
            20
```

```
<210> SEQ ID NO 203
<211> LENGTH: 11
<212> TYPE: PRT
```

```
<213> ORGANISM: Artifical

<400> SEQUENCE: 203

Arg Ala Ser Gln Gly Ile Arg Asn Asp Leu Gly
1               5                   10

<210> SEQ ID NO 204
<211> LENGTH: 15
<212> TYPE: PRT
<213> ORGANISM: Artifical

<400> SEQUENCE: 204

Trp Tyr Gln Gln Lys Ala Gly Lys Ala Pro Lys Leu Leu Ile Tyr
1               5                   10                  15

<210> SEQ ID NO 205
<211> LENGTH: 7
<212> TYPE: PRT
<213> ORGANISM: Artifical

<400> SEQUENCE: 205

Ala Ala Ser Ser Leu Gln Ser
1               5

<210> SEQ ID NO 206
<211> LENGTH: 32
<212> TYPE: PRT
<213> ORGANISM: Artifical

<400> SEQUENCE: 206

Gly Val Pro Ser Arg Phe Ser Gly Ser Gly Ser Gly Thr Asp Phe Thr
1               5                   10                  15

Leu Thr Ile Ser Ser Leu Gln Pro Asp Asp Phe Ala Thr Tyr Phe Cys
            20                  25                  30

<210> SEQ ID NO 207
<211> LENGTH: 9
<212> TYPE: PRT
<213> ORGANISM: Artifical

<400> SEQUENCE: 207

Gln Gln Ala His Ser Phe Pro Pro Thr
1               5

<210> SEQ ID NO 208
<211> LENGTH: 11
<212> TYPE: PRT
<213> ORGANISM: Artifical

<400> SEQUENCE: 208

Phe Gly Gly Gly Thr Lys Val Glu Ile Lys Arg
1               5                   10

<210> SEQ ID NO 209
<211> LENGTH: 22
<212> TYPE: PRT
<213> ORGANISM: Artifical

<400> SEQUENCE: 209

Gln Ser Ala Leu Thr Gln Pro Ala Ser Val Ser Gly Ser Pro Gly Gln
1               5                   10                  15

Ser Ile Thr Ile Ser Cys
            20
```

```
<210> SEQ ID NO 210
<211> LENGTH: 14
<212> TYPE: PRT
<213> ORGANISM: Artifical

<400> SEQUENCE: 210

Thr Gly Thr Ser Ser Asp Val Gly Gly Tyr Asn Phe Val Ser
1               5                   10

<210> SEQ ID NO 211
<211> LENGTH: 15
<212> TYPE: PRT
<213> ORGANISM: Artifical

<400> SEQUENCE: 211

Trp Tyr Gln Gln His Pro Gly Lys Ala Pro Lys Leu Met Ile Tyr
1               5                   10                  15

<210> SEQ ID NO 212
<211> LENGTH: 7
<212> TYPE: PRT
<213> ORGANISM: Artifical

<400> SEQUENCE: 212

Asp Val Ser Asp Arg Pro Ser
1               5

<210> SEQ ID NO 213
<211> LENGTH: 32
<212> TYPE: PRT
<213> ORGANISM: Artifical

<400> SEQUENCE: 213

Gly Val Ser Asp Arg Phe Ser Gly Ser Lys Ser Gly Asn Thr Ala Ser
1               5                   10                  15

Leu Ile Ile Ser Gly Leu Gln Ala Asp Asp Glu Ala Asp Tyr Tyr Cys
            20                  25                  30

<210> SEQ ID NO 214
<211> LENGTH: 11
<212> TYPE: PRT
<213> ORGANISM: Artifical

<400> SEQUENCE: 214

Ser Ser Tyr Gly Ser Ser Ser Thr His Val Ile
1               5                   10

<210> SEQ ID NO 215
<211> LENGTH: 10
<212> TYPE: PRT
<213> ORGANISM: Artifical

<400> SEQUENCE: 215

Phe Gly Gly Gly Thr Lys Val Thr Val Leu
1               5                   10

<210> SEQ ID NO 216
<211> LENGTH: 22
<212> TYPE: PRT
<213> ORGANISM: Artifical

<400> SEQUENCE: 216

Gln Ser Val Leu Thr Gln Pro Pro Ser Val Ser Ala Ala Pro Gly Gln
1               5                   10                  15

Lys Val Thr Ile Ser Cys
```

-continued

<210> SEQ ID NO 217
<211> LENGTH: 13
<212> TYPE: PRT
<213> ORGANISM: Artifical

<400> SEQUENCE: 217

Ser Gly Ser Ser Ser Asn Ile Gly Asn Asn Tyr Val Ser
1               5                   10

<210> SEQ ID NO 218
<211> LENGTH: 15
<212> TYPE: PRT
<213> ORGANISM: Artifical

<400> SEQUENCE: 218

Trp Tyr Gln Gln Leu Pro Gly Thr Ala Pro Lys Leu Leu Ile Tyr
1               5                   10                  15

<210> SEQ ID NO 219
<211> LENGTH: 7
<212> TYPE: PRT
<213> ORGANISM: Artifical

<400> SEQUENCE: 219

Gly His Thr Asn Arg Pro Ala
1               5

<210> SEQ ID NO 220
<211> LENGTH: 32
<212> TYPE: PRT
<213> ORGANISM: Artifical

<400> SEQUENCE: 220

Gly Val Pro Asp Arg Phe Ser Gly Ser Lys Ser Gly Thr Ser Ala Ser
1               5                   10                  15

Leu Ala Ile Ser Gly Phe Arg Ser Glu Asp Glu Ala Asp Tyr Tyr Cys
                20                  25                  30

<210> SEQ ID NO 221
<211> LENGTH: 11
<212> TYPE: PRT
<213> ORGANISM: Artifical

<400> SEQUENCE: 221

Ala Ala Trp Asp Asp Ser Leu Ser Gly Trp Val
1               5                   10

<210> SEQ ID NO 222
<211> LENGTH: 10
<212> TYPE: PRT
<213> ORGANISM: Artifical

<400> SEQUENCE: 222

Phe Gly Gly Gly Thr Lys Leu Thr Val Leu
1               5                   10

<210> SEQ ID NO 223
<211> LENGTH: 22
<212> TYPE: PRT
<213> ORGANISM: Artifical

<400> SEQUENCE: 223

Gln Ser Val Leu Thr Gln Pro Pro Ser Val Ser Ala Ala Pro Gly Gln

```
                1               5                  10                 15

Lys Val Thr Ile Ser Cys
                20

<210> SEQ ID NO 224
<211> LENGTH: 13
<212> TYPE: PRT
<213> ORGANISM: Artifical

<400> SEQUENCE: 224

Ser Gly Ser Ser Ser Asn Ile Gly Asn Asn Tyr Val Ser
1               5                   10

<210> SEQ ID NO 225
<211> LENGTH: 15
<212> TYPE: PRT
<213> ORGANISM: Artifical

<400> SEQUENCE: 225

Trp Tyr Gln Gln Leu Pro Gly Thr Ala Pro Lys Leu Leu Ile Tyr
1               5                   10                  15

<210> SEQ ID NO 226
<211> LENGTH: 7
<212> TYPE: PRT
<213> ORGANISM: Artifical

<400> SEQUENCE: 226

Asp His Thr Asn Arg Pro Ala
1               5

<210> SEQ ID NO 227
<211> LENGTH: 32
<212> TYPE: PRT
<213> ORGANISM: Artifical

<400> SEQUENCE: 227

Gly Val Pro Asp Arg Phe Ser Gly Ser Lys Ser Gly Thr Ser Ala Ser
1               5                   10                  15

Leu Ala Ile Ser Gly Phe Arg Ser Glu Asp Glu Ala Asp Tyr Tyr Cys
                20                  25                  30

<210> SEQ ID NO 228
<211> LENGTH: 11
<212> TYPE: PRT
<213> ORGANISM: Artifical

<400> SEQUENCE: 228

Ala Ser Trp Asp Tyr Thr Leu Ser Gly Trp Val
1               5                   10

<210> SEQ ID NO 229
<211> LENGTH: 10
<212> TYPE: PRT
<213> ORGANISM: Artifical

<400> SEQUENCE: 229

Phe Gly Gly Gly Thr Lys Leu Thr Val Leu
1               5                   10

<210> SEQ ID NO 230
<211> LENGTH: 22
<212> TYPE: PRT
<213> ORGANISM: Artifical
```

```
<400> SEQUENCE: 230

Gln Ser Val Leu Thr Gln Asp Pro Ala Val Ser Val Ala Leu Gly Gln
1               5                   10                  15

Thr Val Lys Ile Thr Cys
            20

<210> SEQ ID NO 231
<211> LENGTH: 11
<212> TYPE: PRT
<213> ORGANISM: Artifical

<400> SEQUENCE: 231

Gln Gly Asp Ser Leu Arg Ser Tyr Phe Ala Ser
1               5                   10

<210> SEQ ID NO 232
<211> LENGTH: 15
<212> TYPE: PRT
<213> ORGANISM: Artifical

<400> SEQUENCE: 232

Trp Tyr Gln Gln Lys Pro Gly Gln Ala Pro Thr Leu Val Met Tyr
1               5                   10                  15

<210> SEQ ID NO 233
<211> LENGTH: 7
<212> TYPE: PRT
<213> ORGANISM: Artifical

<400> SEQUENCE: 233

Ala Arg Asn Asp Arg Pro Ala
1               5

<210> SEQ ID NO 234
<211> LENGTH: 32
<212> TYPE: PRT
<213> ORGANISM: Artifical

<400> SEQUENCE: 234

Gly Val Pro Asp Arg Phe Ser Gly Ser Lys Ser Gly Thr Ser Ala Ser
1               5                   10                  15

Leu Ala Ile Ser Gly Leu Gln Ser Glu Asp Glu Ala Asp Tyr Tyr Cys
            20                  25                  30

<210> SEQ ID NO 235
<211> LENGTH: 11
<212> TYPE: PRT
<213> ORGANISM: Artifical

<400> SEQUENCE: 235

Ala Ala Trp Asp Asp Ser Leu Asn Gly Tyr Leu
1               5                   10

<210> SEQ ID NO 236
<211> LENGTH: 10
<212> TYPE: PRT
<213> ORGANISM: Artifical

<400> SEQUENCE: 236

Phe Gly Ala Gly Thr Lys Leu Thr Val Leu
1               5                   10

<210> SEQ ID NO 237
<211> LENGTH: 22
```

```
<212> TYPE: PRT
<213> ORGANISM: Artifical

<400> SEQUENCE: 237

Gln Ser Val Leu Thr Gln Asp Pro Ala Val Ser Val Ala Leu Gly Gln
1               5                   10                  15

Thr Val Lys Ile Thr Cys
            20

<210> SEQ ID NO 238
<211> LENGTH: 11
<212> TYPE: PRT
<213> ORGANISM: Artifical

<400> SEQUENCE: 238

Gln Gly Asp Ser Leu Arg Ser Tyr Phe Ala Ser
1               5                   10

<210> SEQ ID NO 239
<211> LENGTH: 15
<212> TYPE: PRT
<213> ORGANISM: Artifical

<400> SEQUENCE: 239

Trp Tyr Gln Gln Lys Pro Gly Gln Ala Pro Thr Leu Val Met Tyr
1               5                   10                  15

<210> SEQ ID NO 240
<211> LENGTH: 7
<212> TYPE: PRT
<213> ORGANISM: Artifical

<400> SEQUENCE: 240

Ala Arg Asn Asp Arg Pro Ala
1               5

<210> SEQ ID NO 241
<211> LENGTH: 32
<212> TYPE: PRT
<213> ORGANISM: Artifical

<400> SEQUENCE: 241

Gly Val Pro Asp Arg Phe Ser Gly Ser Lys Ser Gly Thr Ser Ala Ser
1               5                   10                  15

Leu Ala Ile Ser Gly Leu Gln Ser Glu Asp Glu Ala Asp Tyr Tyr Cys
            20                  25                  30

<210> SEQ ID NO 242
<211> LENGTH: 11
<212> TYPE: PRT
<213> ORGANISM: Artifical

<400> SEQUENCE: 242

Ala Ala Trp Asp Asp Ser Leu Asn Gly Tyr Leu
1               5                   10

<210> SEQ ID NO 243
<211> LENGTH: 10
<212> TYPE: PRT
<213> ORGANISM: Artifical

<400> SEQUENCE: 243

Phe Gly Ala Gly Thr Lys Leu Thr Val Leu
1               5                   10
```

```
<210> SEQ ID NO 244
<211> LENGTH: 22
<212> TYPE: PRT
<213> ORGANISM: Artifical

<400> SEQUENCE: 244

Gln Ser Val Leu Thr Gln Pro Pro Ser Val Ser Gly Ala Pro Gly Gln
1               5                   10                  15

Arg Val Thr Ile Ser Cys
            20

<210> SEQ ID NO 245
<211> LENGTH: 14
<212> TYPE: PRT
<213> ORGANISM: Artifical

<400> SEQUENCE: 245

Thr Gly Ser Ser Ser Asn Ile Gly Ala Gly Tyr Gly Val His
1               5                   10

<210> SEQ ID NO 246
<211> LENGTH: 15
<212> TYPE: PRT
<213> ORGANISM: Artifical

<400> SEQUENCE: 246

Trp Tyr Gln Gln Leu Pro Gly Thr Ala Pro Lys Leu Leu Ile Tyr
1               5                   10                  15

<210> SEQ ID NO 247
<211> LENGTH: 7
<212> TYPE: PRT
<213> ORGANISM: Artifical

<400> SEQUENCE: 247

Gly Asn Thr Asn Arg Pro Ser
1               5

<210> SEQ ID NO 248
<211> LENGTH: 32
<212> TYPE: PRT
<213> ORGANISM: Artifical

<400> SEQUENCE: 248

Gly Val Pro Asp Arg Phe Ser Gly Phe Lys Ser Gly Thr Ser Ala Ser
1               5                   10                  15

Leu Ala Ile Thr Gly Leu Gln Ala Glu Asp Glu Ala Asp Tyr Tyr Cys
            20                  25                  30

<210> SEQ ID NO 249
<211> LENGTH: 11
<212> TYPE: PRT
<213> ORGANISM: Artifical

<400> SEQUENCE: 249

Gln Ser Tyr Asp Ser Ser Leu Ser Gly Trp Val
1               5                   10

<210> SEQ ID NO 250
<211> LENGTH: 10
<212> TYPE: PRT
<213> ORGANISM: Artifical

<400> SEQUENCE: 250
```

```
Phe Gly Gly Gly Thr Lys Leu Thr Val Leu
1               5                  10

<210> SEQ ID NO 251
<211> LENGTH: 23
<212> TYPE: PRT
<213> ORGANISM: Artifical

<400> SEQUENCE: 251

Asp Ile Gln Met Thr Gln Ser Pro Ser Thr Leu Ser Ala Ser Leu Gly
1               5                   10                  15

Asp Arg Val Thr Ile Thr Cys
            20

<210> SEQ ID NO 252
<211> LENGTH: 11
<212> TYPE: PRT
<213> ORGANISM: Artifical

<400> SEQUENCE: 252

Arg Ala Ser Gln Ser Ile Gly Ser Trp Leu Ala
1               5                   10

<210> SEQ ID NO 253
<211> LENGTH: 15
<212> TYPE: PRT
<213> ORGANISM: Artifical

<400> SEQUENCE: 253

Trp Tyr Gln Gln Lys Pro Gly Lys Ala Pro Lys Leu Leu Ile Tyr
1               5                   10                  15

<210> SEQ ID NO 254
<211> LENGTH: 7
<212> TYPE: PRT
<213> ORGANISM: Artifical

<400> SEQUENCE: 254

Lys Ala Ser Thr Leu Glu Ser
1               5

<210> SEQ ID NO 255
<211> LENGTH: 32
<212> TYPE: PRT
<213> ORGANISM: Artifical

<400> SEQUENCE: 255

Gly Val Pro Ser Arg Phe Thr Gly Ser Gly Ser Gly Thr Glu Phe Thr
1               5                   10                  15

Leu Thr Ile Ser Gly Leu Gln Pro Glu Asp Phe Ala Thr Tyr Tyr Cys
            20                  25                  30

<210> SEQ ID NO 256
<211> LENGTH: 9
<212> TYPE: PRT
<213> ORGANISM: Artifical

<400> SEQUENCE: 256

Gln Lys Leu Ser Ser Tyr Pro Leu Thr
1               5

<210> SEQ ID NO 257
<211> LENGTH: 11
<212> TYPE: PRT
<213> ORGANISM: Artifical
```

```
<400> SEQUENCE: 257

Phe Gly Gly Gly Thr Lys Val Glu Ile Lys Arg
1               5                   10

<210> SEQ ID NO 258
<211> LENGTH: 22
<212> TYPE: PRT
<213> ORGANISM: Artifical

<400> SEQUENCE: 258

Gln Ser Ala Leu Thr Gln Pro Ala Ser Val Ser Gly Ser Pro Gly Gln
1               5                   10                  15

Ser Ile Thr Ile Ser Cys
            20

<210> SEQ ID NO 259
<211> LENGTH: 14
<212> TYPE: PRT
<213> ORGANISM: Artifical

<400> SEQUENCE: 259

Thr Gly Thr Ser Ser Asp Val Gly Gly Tyr Asn Tyr Val Ser
1               5                   10

<210> SEQ ID NO 260
<211> LENGTH: 15
<212> TYPE: PRT
<213> ORGANISM: Artifical

<400> SEQUENCE: 260

Trp Tyr Gln Gln His Pro Gly Lys Ala Pro Lys Leu Met Ile Tyr
1               5                   10                  15

<210> SEQ ID NO 261
<211> LENGTH: 7
<212> TYPE: PRT
<213> ORGANISM: Artifical

<400> SEQUENCE: 261

Glu Val Ser Asn Arg Pro Ser
1               5

<210> SEQ ID NO 262
<211> LENGTH: 32
<212> TYPE: PRT
<213> ORGANISM: Artifical

<400> SEQUENCE: 262

Gly Val Ser Asn Arg Phe Ser Gly Ser Lys Ser Gly Asn Thr Ala Ser
1               5                   10                  15

Leu Thr Ile Ser Gly Leu Gln Ala Glu Asp Glu Ala Asp Tyr Tyr Cys
            20                  25                  30

<210> SEQ ID NO 263
<211> LENGTH: 10
<212> TYPE: PRT
<213> ORGANISM: Artifical

<400> SEQUENCE: 263

Asn Ser Tyr Thr Ser Ser Ser Thr Trp Val
1               5                   10

<210> SEQ ID NO 264
```

```
<211> LENGTH: 10
<212> TYPE: PRT
<213> ORGANISM: Artifical

<400> SEQUENCE: 264

Phe Gly Gly Gly Thr Lys Leu Thr Val Leu
1               5                   10

<210> SEQ ID NO 265
<211> LENGTH: 22
<212> TYPE: PRT
<213> ORGANISM: Artifical

<400> SEQUENCE: 265

Gln Ser Val Leu Thr Gln Pro Pro Ser Val Ser Ala Ala Pro Gly Gln
1               5                   10                  15

Lys Val Thr Ile Ser Cys
            20

<210> SEQ ID NO 266
<211> LENGTH: 13
<212> TYPE: PRT
<213> ORGANISM: Artifical

<400> SEQUENCE: 266

Ser Gly Ser Ser Ser Asn Ile Gly Asn Asn Tyr Val Ser
1               5                   10

<210> SEQ ID NO 267
<211> LENGTH: 15
<212> TYPE: PRT
<213> ORGANISM: Artifical

<400> SEQUENCE: 267

Trp Tyr Gln Gln Leu Pro Gly Thr Ala Pro Lys Leu Leu Ile Tyr
1               5                   10                  15

<210> SEQ ID NO 268
<211> LENGTH: 7
<212> TYPE: PRT
<213> ORGANISM: Artifical

<400> SEQUENCE: 268

Gly His Thr Asn Arg Pro Ala
1               5

<210> SEQ ID NO 269
<211> LENGTH: 32
<212> TYPE: PRT
<213> ORGANISM: Artifical

<400> SEQUENCE: 269

Gly Val Pro Asp Arg Phe Ser Gly Ser Lys Ser Gly Thr Ser Ala Ser
1               5                   10                  15

Leu Ala Ile Ser Gly Phe Arg Ser Glu Asp Glu Ala Asp Tyr Tyr Cys
            20                  25                  30

<210> SEQ ID NO 270
<211> LENGTH: 11
<212> TYPE: PRT
<213> ORGANISM: Artifical

<400> SEQUENCE: 270

Ala Ala Trp Asp Asp Ser Leu Ser Gly Trp Val
1               5                   10
```

```
<210> SEQ ID NO 271
<211> LENGTH: 10
<212> TYPE: PRT
<213> ORGANISM: Artifical

<400> SEQUENCE: 271

Phe Gly Gly Gly Thr Lys Leu Thr Val Leu
1               5                   10

<210> SEQ ID NO 272
<211> LENGTH: 20
<212> TYPE: PRT
<213> ORGANISM: Artificial
<220> FEATURE:
<223> OTHER INFORMATION: Peptide linker.

<400> SEQUENCE: 272

Asn Ser Gly Ala Gly Thr Ser Gly Ser Gly Ala Ser Gly Glu Gly Ser
1               5                   10                  15

Gly Ser Lys Leu
            20

<210> SEQ ID NO 273
<211> LENGTH: 5
<212> TYPE: PRT
<213> ORGANISM: Artificial
<220> FEATURE:
<223> OTHER INFORMATION: Peptide linker.

<400> SEQUENCE: 273

Gly Gly Gly Gly Ser
1               5

<210> SEQ ID NO 274
<211> LENGTH: 5
<212> TYPE: PRT
<213> ORGANISM: Artificial
<220> FEATURE:
<223> OTHER INFORMATION: Signal sequence.

<400> SEQUENCE: 274

Arg Glu Asp Leu Lys
1               5

<210> SEQ ID NO 275
<211> LENGTH: 4
<212> TYPE: PRT
<213> ORGANISM: Artificial
<220> FEATURE:
<223> OTHER INFORMATION: Signal sequence.

<400> SEQUENCE: 275

Arg Glu Asp Leu
1

<210> SEQ ID NO 276
<211> LENGTH: 4
<212> TYPE: PRT
<213> ORGANISM: Artificial
<220> FEATURE:
<223> OTHER INFORMATION: Signal sequence.

<400> SEQUENCE: 276

Arg Asp Glu Leu
1
```

```
<210> SEQ ID NO 277
<211> LENGTH: 4
<212> TYPE: PRT
<213> ORGANISM: Artificial
<220> FEATURE:
<223> OTHER INFORMATION: Signal sequence.

<400> SEQUENCE: 277

Lys Asp Glu Leu
1

<210> SEQ ID NO 278
<211> LENGTH: 55
<212> TYPE: DNA
<213> ORGANISM: Artificial
<220> FEATURE:
<223> OTHER INFORMATION: PCR primer.

<400> SEQUENCE: 278
aattcaggtg ctggtacttc aggttcaggt gcttcaggtg aaggttcagg ttcaa          55

<210> SEQ ID NO 279
<211> LENGTH: 55
<212> TYPE: DNA
<213> ORGANISM: Artificial
<220> FEATURE:
<223> OTHER INFORMATION: PCR primer.

<400> SEQUENCE: 279
agctttgaac ctgaaccttc acctgaagca cctgaacctg aagtaccagc acctg          55

<210> SEQ ID NO 280
<211> LENGTH: 60
<212> TYPE: DNA
<213> ORGANISM: Artificial
<220> FEATURE:
<223> OTHER INFORMATION: Nucleic acid encoding peptide linker.

<400> SEQUENCE: 280
aattcaggtg ctggtacttc aggttcaggt gcttcaggtg aaggttcagg ttcaaagcta     60

<210> SEQ ID NO 281
<211> LENGTH: 20
<212> TYPE: PRT
<213> ORGANISM: Artificial
<220> FEATURE:
<223> OTHER INFORMATION: Peptide linker.

<400> SEQUENCE: 281

Asn Ser Gly Ala Gly Thr Ser Gly Ser Gly Ala Ser Gly Glu Gly Ser
1               5                   10                  15

Gly Ser Lys Leu
            20

<210> SEQ ID NO 282
<211> LENGTH: 29
<212> TYPE: DNA
<213> ORGANISM: Artificial
<220> FEATURE:
<223> OTHER INFORMATION: PCR primer.

<400> SEQUENCE: 282
cgaccatggc ccaggtgcag ctggtgcag                                       29

<210> SEQ ID NO 283
<211> LENGTH: 27
```

```
<212> TYPE: DNA
<213> ORGANISM: Artificial
<220> FEATURE:
<223> OTHER INFORMATION: PCR primer.

<400> SEQUENCE: 283
cgaattcacc taggacggtc agcttgg                                          27

<210> SEQ ID NO 284
<211> LENGTH: 32
<212> TYPE: DNA
<213> ORGANISM: Artificial
<220> FEATURE:
<223> OTHER INFORMATION: PCR primer.

<400> SEQUENCE: 284
gggaagcttc aggtgcagct ggtgcagtct gg                                    32

<210> SEQ ID NO 285
<211> LENGTH: 33
<212> TYPE: DNA
<213> ORGANISM: Artificial
<220> FEATURE:
<223> OTHER INFORMATION: PCR primer.

<400> SEQUENCE: 285
gggctcgaga cctaggacgg tcagcttggt tcc                                   33

<210> SEQ ID NO 286
<211> LENGTH: 6
<212> TYPE: PRT
<213> ORGANISM: Artificial
<220> FEATURE:
<223> OTHER INFORMATION: His tag.

<400> SEQUENCE: 286

His His His His His His
1               5

<210> SEQ ID NO 287
<211> LENGTH: 29
<212> TYPE: DNA
<213> ORGANISM: Artificial
<220> FEATURE:
<223> OTHER INFORMATION: PCR primer.

<400> SEQUENCE: 287
cgaccatggc ccaggtgcag ctggtgcag                                        29

<210> SEQ ID NO 288
<211> LENGTH: 34
<212> TYPE: DNA
<213> ORGANISM: Artificial
<220> FEATURE:
<223> OTHER INFORMATION: PCR primer.

<400> SEQUENCE: 288
gatataatgc ggccgctcag tggtggtggt ggtg                                  34
```

ANTI-EGFR FAMILY ANTIBODIES, BISPECIFIC ANTI-EGFR FAMILY ANTIBODIES AND METHODS OF USE THEREOF

CROSS-REFERENCE TO RELATED APPLICATIONS

This application is a 371 National Phase of PCT/US2007/024287, filed on Nov. 20, 2007, which claims benefit of and priority to U.S. Ser. No. 60/860,750, filed on Nov. 21, 2006, and U.S. Ser. No. 60/867,015, filed on Nov. 22, 2006, all of which are incorporated herein by reference in their entirety for all purposes.

STATEMENT AS TO RIGHTS TO INVENTIONS MADE UNDER FEDERALLY SPONSORED RESEARCH AND DEVELOPMENT

This work was supported in part by a Grant from the United States Army Medical Research and Material Command Breast Cancer Research Program, Grant No: DAMD 17-01-1-0520, and The United States National Cancer Institute, Institutional Pilot Grant No: NCI CA06927. The government of the United States of America may have certain rights in this invention.

FIELD OF THE INVENTION

The present invention relates to the fields of immunology and oncology, and more specifically, to monospecific or bispecific antibody molecules (e.g., bs scFv) that can be used to advantage in the detection and/or treatment of various cancers that overexpress the Epidermal Growth Factor Receptor (EGFR) family of proteins. Certain illustrative bispecific scFv antibody molecules of the invention have binding specificities for either two distinct epitopes of a single member of the EGFR family or alternatively specificity for two distinct members of the EGFR family.

BACKGROUND OF THE INVENTION

The Epidermal Growth Factor Receptor (EGFR) signaling pathway plays an important role in the development and spread of cancer throughout the body. EGFR is expressed in a wide range of solid tumors, including colon cancers, head and neck cancers, pancreatic cancers, ovarian cancers, and breast cancers.

HER2/neu is a cell surface receptor protein with tyrosine kinase activity. The complete protein consists of three parts: an intracellular cytoplasmic domain, a short hydrophobic transmembrane segment and an extracellular domain (ECD) that is responsible for ligand binding. This receptor protein is expressed on the cell membrane of a variety of epithelial cell types and, through binding of specific growth factors, regulates various aspects of cell growth division.

Her2/neu, the gene that encodes for the HER2/neu protein, is a member of a group of genes known as proto-oncogenes. Proto-oncogenes encode important proteins, such as growth factors, growth factor receptors, and apoptotic proteins that are involved in normal cell growth and differentiation. When proto-oncogenes are altered by point mutation, translocation or gene amplification, they produce growth signals that may lead to aberrant cellular transformation and the development of cancer.

While Her2/neu can be expressed at low levels in many normal cells, it is typically overexpressed in a variety of cancers. Overexpression of Her2/neu is caused in most cases by an increase in copy number of the gene (gene amplification) and/or by an increase in expression level of the Her2/neu genes in the cell. Overexpression of this growth factor receptor plays a key role in tumor progression by causing a higher rate of cell growth and oncogenic transformation. Gene amplification of the Her2/neu gene has been observed in a variety of cancer types, including, breast, ovarian, endometrial, gastric, pancreatic, prostate and salivary gland (Hynes and Stern (1994) *Biochim Biophys Acta.*, 1198: 165-184). In breast cancer patients, HER2/neu has also been shown to be of clinical importance as it is associated with poor prognosis, tumor recurrence and shortened survival in breast cancer patients (Seshadri et al. (1993) *J. Clin. Oncol.*, 11: 1936-1942; Berger et al. (1988) *Cancer Res.*, 48: 1238-1243; O'Reilly et al. (1991) *Br. J. Cancer*, 63: 444-446).

Currently, a great deal of attention has focused on the development of novel immunotherapy strategies for the treatment of cancer. One such strategy is antibody-based cancer therapy. A major goal of antibody-based cancer therapy is to specifically deliver toxic payloads such as radioisotopes, toxins or drugs to tumors. The size range of antibody binding site-based molecules includes: IgM (1000 kDa), IgG (150 kDa), F(ab')$_2$ (100 kDa), Fab (50 kDa), (scFv)$_2$ (55 kDa) and scFv (25 kDa). In immunodeficient mice, larger molecules such as IgG and F(ab)$_2$ fragments are retained at high levels in human tumor xenografts with a low degree of specificity (Adams et al. (1992) *Antibody, Immunoconj. Radiopharm.*, 5: 81-95; Milenic et al. (1991) *J. Cancer Res.* 51: 6363-6371), while smaller molecules such as scFv, (scFv)$_2$ and Fab are retained in tumors at comparatively lower levels with greatly improved specificity (Milenic et al. (1991) *J. Cancer Res.* 51: 6363-6371; Adams et al. (1993) *Cancer Res.* 53: 4026-4034; Beaumier et al. (1985) *J. Nucl. Med.* 26: 1172-1179; Colcher et al. (1990) *J. Natl. Cancer Inst.* 82: 1191-1197).

The most prominent determinant of the above targeting properties is the size of the antibody-based molecule relative to the renal threshold for first pass clearance. Another important feature of antibody-based molecules is valence, as significantly greater tumor retention has been associated with multivalent binding to target antigen (Milenic et al. (1991) *J. Cancer Res.* 51: 6363-6371; Adams et al. (1993) *Cancer Res.* 53: 4026-4034; Adams et al. (1996) *Proc. Amer. Assoc. Cancer Res.* 37: 472; Wolf et al. (1993) *Cancer Res.* 53: 2560-2565).

Herceptin, a new form of immunotherapy targeting breast cancer, was recently developed to target cancer cells that overexpress Her2/neu. This treatment has been shown in clinical trials to provide effective treatment for patients with HER2/neu positive metastatic breast cancer. However, this drug treatment is costly and is associated with significant morbidity and mortality.

Several other types of therapy have been shown to be more or less effective in breast cancer patients whose tumors express elevated levels of Her2/neu. These include, anthracycline therapy which is thought to be more effective in patients with amplified Her2/neu expression, and hormonal therapy which is less effective in patients whose level of Her2/neu expression is high.

Attention has also focused upon the generation of bivalent single chain Fv-based antibody molecules with molecular weights in the range of the renal threshold for first pass clearance. These include 50 kDa diabodies (Holliger et al. (1993) *Proc. Natl. Acad. Sci. USA*, 90: 6444-6448), 55 kDa (scFv)$_2$ (Adams et al. (1993) *Cancer Res.* 53: 4026-4034), 60-65 kDa amphipathic helix-based scFv dimers (Pack et al. (1993) *Bio/Technology* 11: 1271-1277; Pack (1992) *Bio-*

*chemistry* 31: 1579-1584), and 80 kDa (scFv-$C_H3$)$_2$ LD minibodies and Flex minibodies (Hu et al. (1996) *Cancer Res.* 56: 3055-3061). While each of these proteins is capable of binding two antigen molecules, they differ in the orientation, flexibility and the span of their binding sites. It is believed that these new and innovative immunotherapies will help improve outcomes in breast and other cancers that too frequently recur or progress despite aggressive multi-modality therapy.

SUMMARY OF THE INVENTION

This invention pertains to the identification of novel antibodies that bind to members of the Epidermal Growth Factor Receptor (EGFR-family/ErbB-family) of proteins and that can be used to advantage in the detection and/or treatment of various cancers that overexpress the Epidermal Growth Factor Receptor (EGFR-family/ErbB-family) of proteins. In various embodiments the antibodies themselves can be contacted to such neoplastic cells whereby they inhibit growth and/or proliferation of such cells. Alternatively, the antibodies can be attached to an effector (e.g., detectable label, a cytotoxin, an epitope tag, a second antibody, etc.) whereby the effector can act to inhibit growth and/or proliferation of the target cells or can be used to detect and/or visualize the cells. In certain embodiments the effector is a second antibody thereby forming a bispecific antibody.

Accordingly, in one embodiment this invention provides a bispecific antibody comprising an first antibody and a second antibody joined (directly or through a linker) to each other where the first antibody and the second antibody bind specifically to different epitopes and the first antibody has binding specificity for (specifically binds) at least one epitope on a member of the EbrB/EGFR protein family, (e.g., EGFR, HER2/neu, HER3, HER4), and the second antibody has binding specificity for (specifically binds) a second epitope on a member of the EbrB/EGFR protein family which is different from the first epitope. In certain embodiments the second antibody binds an epitope on a protein selected from the group consisting of EGFR, HER2/neu, HER3 and HER4. In certain embodiments, the antibodies are joined by a linker, more preferably by a peptide linker, and most preferably by a peptide linker that lacks a proteolytic cleavage site (e.g., a linker having the amino acid sequence of SEQ ID NO:273).

In certain embodiments, the first and/or the second antibody specifically binds an epitope specifically bound by an antibody selected from the group consisting of C6.5, C6ML3-9, C6 MH3-B1, C6-B1D2, F5, HER3.A5, HER3.F4, HER3.H1, HER3.H3, HER3.E12, HER3.B12, EGFR.E12, EGFR.C10, EGFR.1C10, EGFR.B11, EGFR.E8, HER4.B4, HER4.G4, HER4.F4, HER4.A8, HER4.B6, HER4.D4, HER4.D7, HER4.D11, HER4.D12, HER4.E3, HER4.E7, HER4.F8, F5B6H2, and HER4.C7.

In certain embodiments a composition is provided comprising an isolated antibody that binds to an EbrB/EGFR family member, where the antibody comprises a heavy chain variable domain (VH) comprising the three VH CDRs of the A5 antibody and/or a light chain variable domain (VL) comprising the three VL CDRs of the A5 antibody. In certain embodiments the antibody comprises a heavy chain variable domain (VH) of the A5 antibody and/or a light chain variable domain (VL) of the A5 antibody. In certain embodiments the antibody comprises a heavy chain variable domain (VH) comprising the three VH CDRs of the A5 antibody and a light chain variable domain (VL) comprising the three VL CDRs of the A5 antibody. In certain embodiments the antibody comprises a heavy chain variable domain (VH) of the A5 antibody and a light chain variable domain (VL) of the A5 antibody.

In certain embodiments a composition is provided comprising an isolated antibody that binds to an EbrB/EGFR family member, where the antibody comprises a heavy chain variable domain (VH) comprising the three VH CDRs of the F5B6H2 antibody and/or a light chain variable domain (VL) comprising the three VL CDRs of the F5B6H2 antibody. In certain embodiments the antibody comprises a heavy chain variable domain (VH) of the F5B6H2 antibody and/or a light chain variable domain (VL) of the F5B6H2 antibody. In certain embodiments the antibody comprises a heavy chain variable domain (VH) comprising the three VH CDRs of the F5B6H2 antibody and a light chain variable domain (VL) comprising the three VL CDRs of the F5B6H2 antibody. In certain embodiments the antibody comprises a heavy chain variable domain (VH) of the F5B6H2 antibody and a light chain variable domain (VL) of the F5B6H2 antibody. In various embodiments the antibodies described herein can include an scFv, an IgG, a Fab, an (Fab')$_2$, and an (scFv')$_2$. In various embodiments any of the antibodies described herein can be coupled to an effector (e.g., a cytotoxin, a label, a a second antibody). In certain embodiments the effector comprises a second antibody, where the second antibody comprises a heavy chain variable domain (VH) comprising the three VH CDRs and/or a light chain variable domain (VL) comprising the three VL CDRs of an antibody selected from the group consisting of A5, F5B6H2, C6.5, C6-B1D2, C6 MH3-B1, C6ML3-9, EGFR.B11, EGFR.C10, EGFR.1C10, EGFR.E12, EGFR.E8, F5, HER3.B12, HER3.E12, HER3.F4, HER3.H1, HER3.H3, HER4.B6, HER4.E3, and G98A. In certain embodiments the second antibody comprises a heavy chain variable domain (VH) comprising the three VH CDRs and a light chain variable domain (VL) comprising the three VL CDRs of an antibody selected from the group consisting of A5, F5B6H2, C6.5, C6-B1D2, C6 MH3-B1, C6ML3-9, EGFR.B11, EGFR.C10, EGFR.1C10, EGFR.E12, EGFR.E8, F5, HER3.B12, HER3.E12, HER3.F4, HER3.H1, HER3.H3, HER4.B6, HER4.E3, and G98A. In certain embodiments the second antibody comprises a heavy chain variable domain (VH) and/or a light chain variable domain (VL) of an antibody selected from the group consisting of A5, F5B6H2, C6.5, C6-B1D2, C6 MH3-B1, C6ML3-9, EGFR.B11, EGFR.C10, EGFR.1C10, EGFR.E12, EGFR.E8, F5, HER3.B12, HER3.E12, HER3.F4, HER3.H1, HER3.H3, HER4.B6, HER4.E3, and G98A. In certain embodiments the second antibody comprises a heavy chain variable domain (VH) and a light chain variable domain (VL) of an antibody selected from the group consisting of A5, F5B6H2, C6.5, C6-B1D2, C6 MH3-B1, C6ML3-9, EGFR.B11, EGFR.C10, EGFR.1C10, EGFR.E12, EGFR.E8, F5, HER3.B12, HER3.E12, HER3.F4, HER3.H1, HER3.H3, HER4.B6, HER4.E3, and G98A. In various embodiments the second antibody is joined to the first antibody by a linker (e.g., a peptide linker). In various embodiments the linker is a peptide linker that lacks a proteolytic cleavage site. In various embodiments the composition further comprises a pharmaceutically acceptable excipient.

Also provided are methods of inhibiting the growth and/or proliferation of a cancer cell. The methods typically involve contacting the cancer cell with an antibody as described herein (e.g., an antibody comprising the VH and/or VL CDRs of A5 and/or F5B6H2). In certain embodiments the antibody is further attached to an effector (e.g., a cytotoxin, an antibody, etc.) as described herein. For example, in certain embodiments the second antibody comprises a heavy chain variable domain (VH) comprising the three VH CDRs and/or a light chain variable domain (VL) comprising the three VL CDRs of an antibody selected from the group consisting of A5; F5B6H2, C6.5, C6-B1D2, C6 MH3-B1, C6ML3-9, EGFR.B11, EGFR.C10, EGFR.E12, EGFR.E8, F5, HER3.B12, HER3.E12, HER3.F4, HER3.H1, HER3.H3, HER4.B6, HER4.E3, and G98A. In certain embodiments the second antibody is joined to the first antibody by a linker (e.g., a peptide linker). In certain embodiments the cancer cell is from a cancer selected from the group consisting of breast, colon, ovarian, endometrial, gastric, pancreatic, prostate, and salivary gland cancer.

In certain embodiments methods of specifically or preferentially delivering an effector molecule to a cell bearing a receptor from the EGFR/ErbB protein family. The methods typically involve providing a chimeric moiety comprising the effector molecule attached to one or more of the antibodies described herein that bind to a member of the EGFR/ErbB protein family (e.g., an antibody that comprises a heavy chain variable domain (VH) comprising the three VH CDRs of the A5 antibody and/or a light chain variable domain (VL) comprising the three VL CDRs of the A5 or F5B6H2 antibody); and contacting the cell with the chimeric moiety, whereby the chimeric moiety specifically binds to the cell. In various embodiments the effector is selected from the group consisting of a cytotoxin, a label, a radionuclide, a drug, a liposome, a ligand, and an antibody. In certain embodiments the chimeric moiety is a fusion protein or a chemical conjugate. In certain embodiments the cell is a cell of a cancer selected from the group consisting of breast cancer, colon cancer, ovarian cancer, endometrial cancer, gastric cancer, pancreatic cancer, prostate cancer, salivary gland cancer, etc. In certain embodiments the "contacting" comprises administration to an organism by a route selected from the group consisting of oral administration, rectal administration, intravenous injection, intramuscular injection, injection into a tumor mass, administration to a surgical site, and the like.

Methods are also provided for specifically killing a cell bearing a receptor from EGFR/ErbB protein family. The methods typically involve providing a chimeric moiety comprising an antibody attached to an effector selected from the group consisting of a cytotoxin, a radioactive moiety, and a liposome comprising a cytotoxic or cytostatic agent, where the antibody comprises one or more of the antibodies described herein (e.g., an antibody comprising a heavy chain variable domain (VH) comprising the three VH CDRs of the A5 or the F5B6H2 antibody and/or a light chain variable domain (VL) comprising the three VL CDRs of the A5 or the F5B6H2 antibody; and contacting the cell with the chimeric moiety, whereby the chimeric moiety specifically binds to the cell resulting in the death of the cell. In certain embodiments the chimeric moiety is a fusion protein or a chemical conjugate. In certain embodiments the cell is a cell of a cancer selected from the group consisting of breast cancer, colon cancer, ovarian cancer, endometrial cancer, gastric cancer, pancreatic cancer, prostate cancer, salivary gland cancer, etc. In certain embodiments the "contacting" comprises administration to an organism by a route selected from the group consisting of oral administration, rectal administration, intravenous injection, intramuscular injection, injection into a tumor mass, administration to a surgical site, and the like.

Methods of detecting a cell or tissue expressing one or more members of the EGFR/ErbB protein family are also provided. These methods typically involve contacting a cell or tissue with a chimeric moiety comprising a detectable label attached to one or more of the antibodies described herein (e.g., an antibody comprising a heavy chain variable domain (VH) comprising the three VH CDRs of the A5 or the F5B6H2 antibody and/or a light chain variable domain (VL) comprising the three VL CDRs of the A5 or the F5B6H2 antibody; and detecting the label where detection of the label in association with the cell or tissue indicates the presence of a cell or tissue expressing one or more members of the EGFR/ErbB protein family. In certain embodiments the detectable label is selected from the group consisting of a gamma emitter, a positron emitter, an MRI label, and a fluorescent label. In certain embodiments the detectable label comprises a gamma emitter and the detecting comprises imaging with a gamma camera. In certain embodiments the detectable label comprises a positron emitter and the detecting comprises imaging with positron emission tomography (PET). In certain embodiments the detectable label comprises an MRI label and the detecting comprises detecting with magnetic resonance imaging. In certain embodiments the cell or tissue expressing one or more members of the Epidermal Growth Factor Receptor Protein family is a cancer cell or tissue. In certain embodiments the cell or tissue expressing one or more members of the EGFR/ErbB protein family comprises a cancer cell (e.g., a cell of a breast cancer, a colon cancer, an ovarian cancer, an endometrial cancer, a gastric cancer, a pancreatic cancer, a prostate cancer, a salivary gland cancer, etc.). In certain embodiments the detecting comprises a non-invasive imaging technique. In certain embodiments the detecting comprises immunohistochemistry. In certain embodiments the detecting comprises detecting in a tissue sample or biopsy. In certain embodiments the detecting comprises detecting in a tissue section. In certain embodiments the detecting comprises detecting the cell or tissue in a human. In certain embodiments the detecting comprises detecting the cell or tissue in a biological sample taken from a human Also provided are nucleic acids that encode any of the antibodies described herein, or any of the fusion proteins (e.g., bispecific antibodies) described herein. For example, nucleic acids are provided that encode an antibody comprising a heavy chain variable domain (VH) comprising the three VH CDRs of the A5 or F5B6H2 antibody and/or a light chain variable domain (VL) comprising the three VL CDRs of the A5 or F5B6H2 antibody. In certain embodiments the nucleic acid further encodes a second antibody attached the isolated antibody. Also provide are vectors (e.g., plasmid, cosmid, phage, virus, etc.) comprising the nucleic acid(s) endogin the isolated antibody and/or bispecific antibodies and/or other antibody fusion proteins.

In certain embodiments host cells are provided where the host cells are cells transfected with a nucleic acid that encodes one or more of the antibodies described herein and/or one or more of the fusion proteins (e.g., bispecific antibodies) described herein. For example in certain embodiments the host cellsa are transfected with a nucleic acid that encodes an antibody comprising a heavy chain variable domain (VH) comprising the three VH CDRs of the A5 or F6B6H2 antibody and/or a light chain variable domain (VL) comprising the three VL CDRs of the A5 or F6B6H2 antibody.

Definitions

The "ErbB family" and "Epidermal Growth Factor (EFG) family)" are used interchangeably and include EGFR/ErbB1/HER1, ErbB2/Neu/HER2, ErbB3/HER3, and ErbB4/HER4.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term also includes variants on the traditional peptide linkage joining the amino acids making up the polypeptide. Preferred "peptides", "polypeptides", and "proteins" are chains of amino acids whose α carbons are linked through peptide bonds. The terminal amino acid at one end of the chain (amino terminal) therefore has a free amino group, while the terminal amino acid at the other end of the chain (carboxy terminal) has a free carboxyl group. As used herein, the term "amino terminus" (abbreviated N-terminus) refers to the free α-amino group on an amino acid at the amino terminal of a peptide or to the α-amino group (imino group when participating in a peptide bond) of an amino acid at any other location within the peptide. Similarly, the term "carboxy terminus" refers to the free carboxyl group on the carboxy terminus of a peptide or the carboxyl group of an amino acid at any other location within the peptide. Peptides also include essentially any polyamino acid including, but not limited to peptide mimetics such as amino acids joined by an ether as opposed to an amide bond.

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as intact immunoglobulins or as a number of well-characterized fragments produced by digestion with various peptidases. Thus, for example, pepsin digests an antibody below the disulfide linkages in the hinge region to produce $F(ab)'_2$, a dimer of Fab which itself is a light chain joined to $V_H$-$C_H1$ by a disulfide bond. The $F(ab)'_2$ may be reduced under mild conditions to break the disulfide linkage in the hinge region thereby converting the $(Fab')_2$ dimer into a Fab' monomer. The Fab' monomer is essentially a Fab with part of the hinge region (see, *Fundamental Immunology*, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes whole antibodies, antibody fragments either produced by the modification of whole antibodies or synthesized de novo using recombinant DNA methodologies. Preferred antibodies include single chain antibodies (antibodies that exist as a single polypeptide chain), more preferably single chain Fv antibodies (scFv) in which a variable heavy and a variable light chain are joined together (directly or through a peptide linker) to form a continuous polypeptide. The single chain Fv antibody is a covalently linked $V_H$-$V_L$ heterodimer which may be expressed from a nucleic acid including $V_H$- and $V_L$-encoding sequences either joined directly or joined by a peptide-encoding linker. Huston, et al. (1988) *Proc. Nat. Acad. Sci. USA*, 85: 5879-5883. While the $V_H$ and $V_L$ are connected to each as a single polypeptide chain, the $V_H$ and $V_L$ domains associate non-covalently. The first functional antibody molecules to be expressed on the surface of filamentous phage were single-chain Fv's (scFv), however, alternative expression strategies have also been successful. For example Fab molecules can be displayed on phage if one of the chains (heavy or light) is fused to g3 capsid protein and the complementary chain exported to the periplasm as a soluble molecule. The two chains can be encoded on the same or on different replicons; the important point is that the two antibody chains in each Fab molecule assemble post-translationally and the dimer is incorporated into the phage particle via linkage of one of the chains to, e.g., g3p (see, e.g., U.S. Pat. No. 5,733,743). The scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art (see e.g., U.S. Pat. Nos. 5,091,513, 5,132,405, and 4,956,778). Particularly preferred antibodies should include all that have been displayed on phage (e.g., scFv, Fv, Fab and disulfide linked Fv (Reiter et al. (1995) *Protein Eng.* 8: 1323-1331), and in addition to monospecific antibodies, also include bispecific, trispecific, quad-raspecific, and generally polyspecific antibodies (e.g., bs scFv).

With respect to antibodies of the invention, the term "immunologically specific" "specifically binds" refers to antibodies that bind to one or more epitopes of a protein of interest (e.g., HER2/neu), but which do not substantially recognize and bind other molecules in a sample containing a mixed population of antigenic biological molecules.

The term "bispecific antibody" as used herein refers to an antibody comprising two antigen-binding sites, a first binding site having affinity for a first antigen or epitope and a second binding site having binding affinity for a second antigen or epitope distinct from the first.

The terms "nucleic acid" or "oligonucleotide" or grammatical equivalents herein refer to at least two nucleotides covalently linked together. A nucleic acid of the present invention is preferably single-stranded or double stranded and will generally contain phosphodiester bonds, although in some cases, as outlined below, nucleic acid analogs are included that may have alternate backbones, comprising, for example, phosphoramide (Beaucage et al. (1993) *Tetrahedron* 49(10):1925) and references therein; Letsinger (1970) *J. Org. Chem.* 35:3800; Sprinzl et al. (1977) *Eur. J. Biochem.* 81: 579; Letsinger et al. (1986) *Nucl. Acids Res.* 14: 3487; Sawai et al. (1984) *Chem. Lett.* 805, Letsinger et al. (1988) *J. Am. Chem. Soc.* 110: 4470; and Pauwels et al. (1986) *Chemica Scripta* 26: 141 9), phosphorothioate (Mag et al. (1991) *Nucleic Acids Res.* 19:1437; and U.S. Pat. No. 5,644,048), phosphorodithioate (Briu et al. (1989) *J. Am. Chem. Soc.* 111:2321, O-methylphophoroamidite linkages (see Eckstein, *Oligonucleotides and Analogues: A Practical Approach*, Oxford University Press), and peptide nucleic acid backbones and linkages (see Egholm (1992) *J. Am. Chem. Soc.* 114:1895; Meier et al. (1992) *Chem. Int. Ed. Engl.* 31: 1008; Nielsen (1993) *Nature,* 365: 566; Carlsson et al. (1996) *Nature* 380: 207). Other analog nucleic acids include those with positive backbones (Denpcy et al. (1995) *Proc. Natl. Acad. Sci. USA* 92: 6097; non-ionic backbones (U.S. Pat. Nos. 5,386,023, 5,637,684, 5,602,240, 5,216,141 and 4,469, 863; Angew. (1991) *Chem. Intl. Ed. English* 30: 423; Letsinger et al. (1988) *J. Am. Chem. Soc.* 110:4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghui and P. Dan Cook; Mesmaeker et al. (1994), *Bioorganic & Medicinal Chem. Lett.* 4: 395; Jeffs et al. (1994) *J. Biomolecular NMR* 34:17; *Tetrahedron Lett* 37:743 (1996)) and non-ribose backbones, including those described in U.S. Pat. Nos. 5,235,033 and 5,034,506, and Chapters 6 and 7, ASC Symposium Series 580, *Carbohydrate Modifications in Antisense Research*, Ed. Y. S. Sanghui and P. Dan Cook. Nucleic acids containing one or more carbocyclic sugars are also included within the definition of nucleic acids (see Jenkins et al. (1995), *Chem. Soc. Rev.* pp 169-176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments.

The terms "hybridizing specifically to" and "specific hybridization" and "selectively hybridize to," as used herein refer to the binding, duplexing, or hybridizing of a nucleic acid molecule preferentially to a particular nucleotide sequence under stringent conditions. The term "stringent conditions" refers to conditions under which a probe will hybridize preferentially to its target subsequence, and to a lesser extent to, or not at all to, other sequences. Stringent hybridization and stringent hybridization wash conditions in the context of nucleic acid hybridization are sequence dependent, and are different under different environmental parameters. An extensive guide to the hybridization of nucleic acids is found in, e.g., Tijssen (1993) *Laboratory Techniques in Biochemistry and Molecular Biology—Hybridization with Nucleic Acid Probes part I, chapt 2, Overview of principles of hybridization and the strategy of nucleic acid probe assays*, Elsevier, N.Y. (Tijssen). Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on an array or on a filter in a Southern or northern blot is 42° C. using standard hybridization solutions (see, e.g., Sambrook (1989) *Molecular Cloning: A Laboratory Manual (2nd ed.) Vol.* 1-3, Cold Spring Harbor Laboratory, Cold Spring Harbor Press, NY, and detailed discussion, below), with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, e.g., Sambrook supra.) for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example of a low stringency wash for a duplex of, e.g., more than 100 nucleotides, is 4× to 6×SSC at 40° C. for 15 minutes.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An "isolated nucleic acid" (either DNA or RNA) may further represent a molecule produced directly by biological or synthetic means and separated from other components present during its production.

A "replicon" is any genetic element, for example, a plasmid, cosmid, bacmid, plastid, phage or virus, that is capable of replication largely under its own control. A replicon may be either RNA or DNA and may be single or double stranded.

A "vector" is a replicon, such as a plasmid, cosmid, bacmid, phage or virus, to which another genetic sequence or element (either DNA or RNA) may be attached so as to bring about the replication of the attached sequence or element.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as appropriate temperature and pH, the primer can be extended at its 3' terminus by the addition of nucleotides by the action of a polymerase or similar activity to yield a primer extension product. The primer can vary in length depending on the particular conditions and requirement of the application. Often primers range from about 15 to about 25 or more nucleotides in length. The primer are typically of sufficient complementarity to the desired template to prime the synthesis of the desired extension product. In other words, the primers are able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases can be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radio immunoassay, or by colorimetric, fluorogenic, chemiluminescent or other methods. The nucleic acid can be either RNA or DNA, linear or circular, single or double stranded, antisense or sense polarity, and is operatively linked to the necessary control elements for the expression of the reporter gene product. The control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

The terms "transform", "transfect", "transduce", shall refer to any method or means by which a nucleic acid is introduced into a cell or host organism and may be used interchangeably to convey the same meaning. Such methods include, but are not limited to, transfection, electroporation, microinjection, PEG-fusion and the like. The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently.

The term "selectable marker gene" refers to a gene that when expressed confers a selectable phenotype, such as antibiotic resistance, on a transformed cell or plant.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g., enhancers) in an expression vector.

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection. With respect to the peptides of this invention sequence identity is determined over the full length of the peptide.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman (1988) *Proc. Natl. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendrogram showing the clustering relationships used to create the alignment. PILEUP uses a simplification of the progressive alignment method of Feng & Doolittle (1987) *J. Mol. Evol.* 35:351-360. The method used is similar to the method described by Higgins & Sharp (1989) *CABIOS* 5: 151-153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al. (1990) *J. Mol. Biol.* 215: 403-410. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul (1993) *Proc. Natl. Acad. Sci. USA*, 90: 5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

The phrase "specifically target/deliver" when used, for example with reference to a chimeric moiety of this invention refers to specific binding of the moiety to a target (e.g., a cell overexpressing the target protein(s)) this results in an increase in local duration and/or concentration of the moiety at or within the cell as compared to that which would be obtained without "specific" targeting. The specificity need not be absolute, but simply detectably greater/measurably avidity/affinity than that observed for a cell expressing the target protein(s) at normal (e.g., wildtype) or than that observed for a cell that does not express the target protein(s).

Amino acid residues are identified in the present application according to standard 3-letter or 1-letter abbreviations (e.g., as set forth in WIPO standard ST 25) and/or as set forth in Table 1.

TABLE 1

Amino acid abbreviations.

| Amino Acid | 3 Letter Abbreviation | 1 Letter Abbreviation |
|---|---|---|
| L-Alanine | Ala | A |
| L-Arginine | Arg | R |
| L-Asparagine | Asn | N |
| L-AsparticAcid | Asp | D |
| L-Cysteine | Cys | C |
| L-Glutamine | Gln | Q |
| L-GlutamicAcid | Glu | E |
| Glycine | Gly | G |
| L-Histidine | His | H |
| L-Isoleucine | Ile | I |
| L-Leucine | Leu | L |
| L-Methionine | Met | M |
| L-Phenylalanine | Phe | F |
| L-Proline | Pro | P |
| L-Serine | Ser | S |
| L-Threonine | Thr | T |
| L-Tryptophan | Trp | W |
| L-Tyrosine | Tyr | Y |
| L-Valine | Val | V |
| L-Lysine | Lys | K |

Enantiomeric amino acids described herein are preferred to be in the "L" isomeric form. However, residues in the "D" isomeric form can be substituted for any L-amino acid residue, provided the desired properties of the polypeptide are retained. All amino-acid residue sequences represented herein conform to the conventional left-to-right amino-terminus to carboxy-terminus orientation.

An "isolated antibody" refers to an antibody that at some time has existed outside an animal typically a mammal. Thus "isolated" excludes naturally occurring antibodies that have existed only in vivo. Alternatively, this term may refer to an antibody that has been sufficiently separated from other proteins or other biomolecules with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example pharmaceutically acceptable preparations.

The term "substantially pure" refers to a preparation comprising at least 50-60% by weight of a given material (e.g., nucleic acid, oligonucleotide, protein, etc.). More preferably, the preparation comprises at least 75% by weight, and most preferably 90-95% by weight of the given compound. Purity is measured by methods appropriate for the given compound (e.g., chromatographic methods, agarose or polyacrylamide gel electrophoresis, HPLC analysis, and the like).

The term "functional" as used herein implies that the nucleic or amino acid sequence is functional for the recited assay or purpose.

The phrase "consisting essentially of" when referring to a particular nucleotide or amino acid means a sequence having the properties of a given SEQ ID NO. For example, when used in reference to an amino acid sequence, the phrase includes the sequence per se and molecular modifications that would not affect the basic and novel characteristics of the sequence.

The term "tag", "tag sequence", or "protein tag" refers to a chemical moiety, either a nucleotide, oligonucleotide, polynucleotide or an amino acid, peptide or protein or other chemical, that when added to another sequence, provides additional utility or confers useful properties, particularly in the detection or isolation, of that sequence. Thus, for example, a homopolymer nucleic acid sequence or a nucleic acid sequence complementary to a capture oligonucleotide may be added to a primer or probe sequence to facilitate the subsequent isolation of an extension product or hybridized product. In the case of protein tags, histidine residues (e.g., 4 to 8 consecutive histidine residues) may be added to either the amino- or carboxy-terminus of a protein to facilitate protein isolation by chelating metal chromatography. Alternatively, amino acid sequences, peptides, proteins or fusion partners representing epitopes or binding determinants reactive with specific antibody molecules or other molecules (e.g., flag epitope, c-myc epitope, transmembrane epitope of the influenza A virus hemaglutinin protein, protein A, cellulose binding domain, calmodulin binding protein, maltose binding protein, chitin binding domain, glutathione S-transferase, and the like) may be added to proteins to facilitate protein isolation by procedures such as affinity or immunoaffinity chromatography. Chemical tag moieties include such molecules as biotin, which may be added to either nucleic acids or proteins and facilitates isolation or detection by interaction with avidin reagents, and the like. Numerous other tag moieties are known to, and can be envisioned by the trained artisan, and are contemplated to be within the scope of this definition.

A "clone" or "clonal cell population" is a population of cells derived from a single cell or common ancestor, e.g., by mitosis.

A "cell line" is a clone of a primary cell or cell population that is capable of stable growth in vitro for many generations.

The following antibody designations are used interchangeably: A5 is interchangeable with HER3.A5, B1D2 is interchangeable with C6-B1D2, ML3.9 is interchangeable with C6ML3-9, B12 is interchangeable with HER3.B12, F4 is interchangeable with HER3.F4, H3 is interchangeable with HER3.H3.

Where an antibody amino acid sequence is shown with a terminal $(His)_6$ (SEQ ID NO:1) sequence, it will be recognized that the $(His)_6$ sequence is a tag and not a component of the antibody CDR or framework. Where an antibody amino acid sequence is shown with the amino acids MA at the leader, it will be recognized that the MA is part of the bacterial leader sequence, not part of the antibody. It is not required for binding (for example we can make IgG without this MA and they bind with wildtype affinity.

BRIEF DESCRIPTION OF THE DRAWINGS

FIG. 13 shows the sequences of ScFv light and heavy chains as determined by the Adams Lab and used in the construction of certain bs-scFv molecules. Sequences are given for C6.5 heavy chain (SEQ ID NO:2), G98A heavy chain (SEQ ID NO:3), ML3-9 heavy chain (SEQ ID NO:4), H3B1 heavy chain (SEQ ID NO:5), B1D2 heavy chain (SEQ ID NO:6), C6.5 light chain (SEQ ID NO:7), G98A light chain (SEQ ID NO:8), ML3-9 light chain (SEQ ID NO:9), H3B1 light chain (SEQ ID NO:10), and B1D2 light chain (SEQ ID NO:11).

FIGS. 14A and 14B shows the amino acid sequence of the VH and VL domains of various antibodies described herein. FIG. 14A shows the VH domains of A5 (SEQ ID NO:12), B12 (SEQ ID NO:13), B1D2 (SEQ ID NO:14), ML3.9 (SEQ ID NO:15), F4 (SEQ ID NO:16), F5B6H2 (SEQ ID NO:17), and H3 (SEQ ID NO:18) antibodies. FIG. 14B shows the VL domains of A5 (SEQ ID NO:19), B12 (SEQ ID NO:20), B1D2 (SEQ ID NO:21), ML3.9 (SEQ ID NO:22), F4 (SEQ ID NO:23), F5B6H2 (SEQ ID NO:24), and H3 (SEQ ID NO:25) antibodies.

Figure 15A:
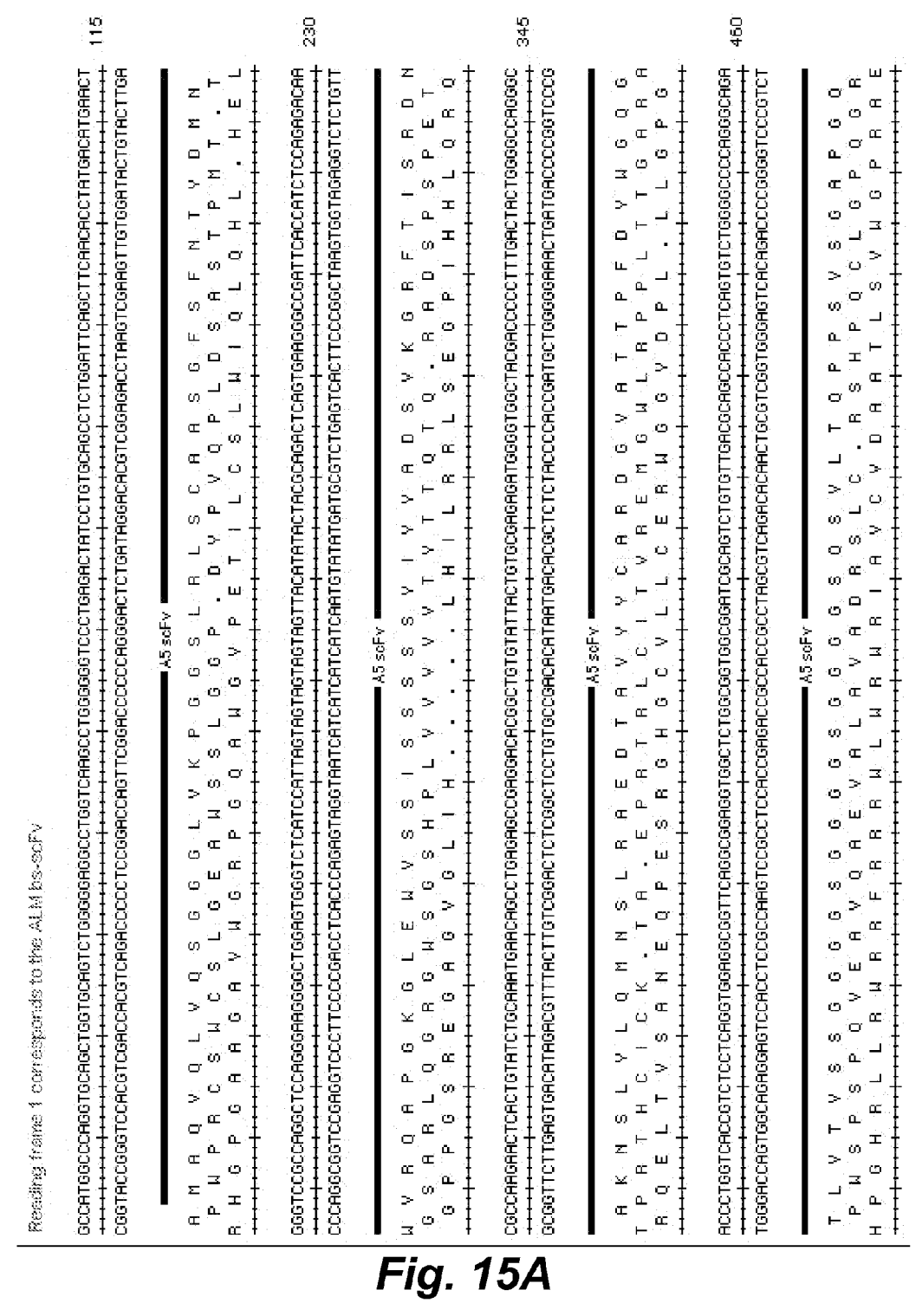
Figure 15B:
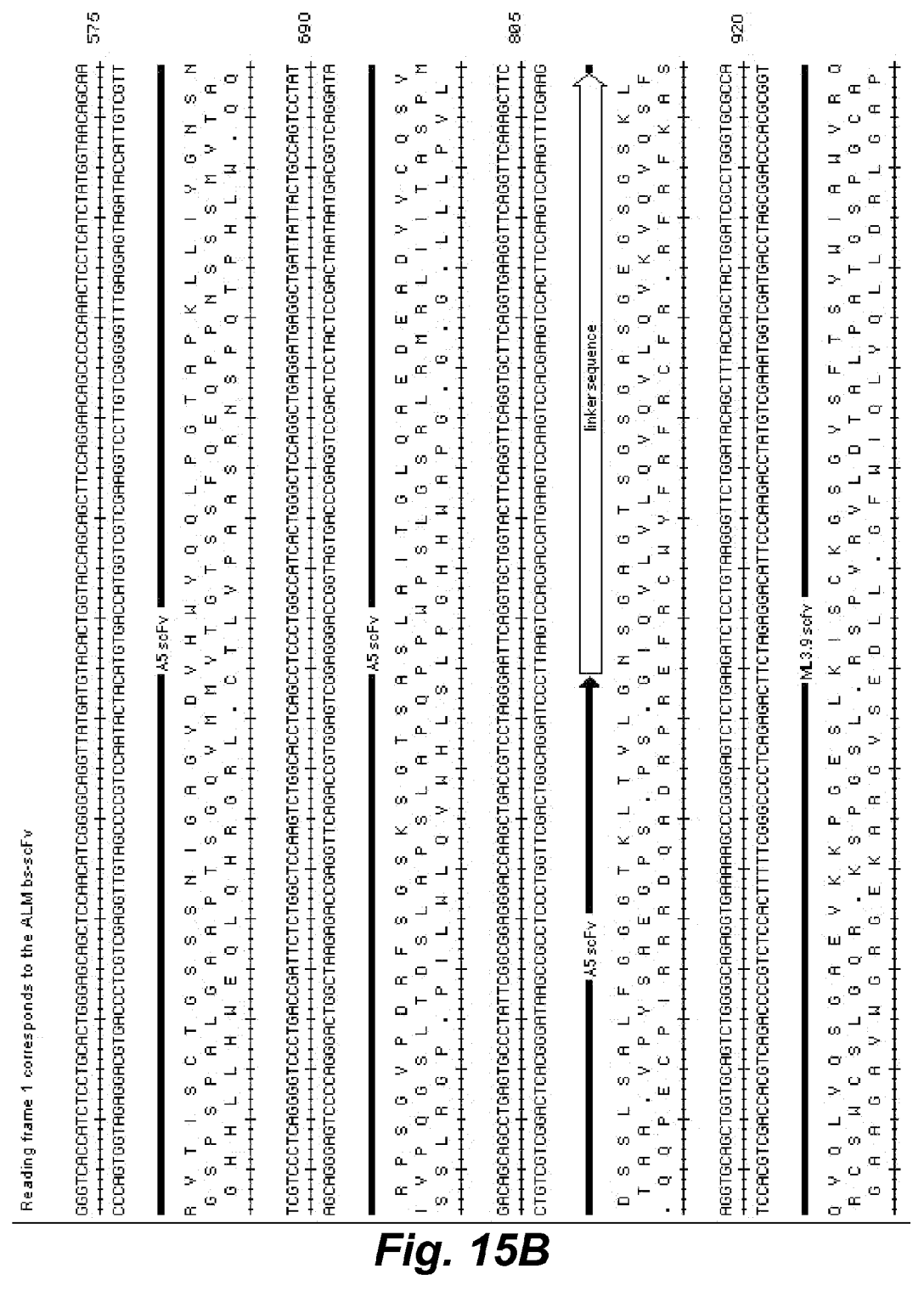
Figure 15C:
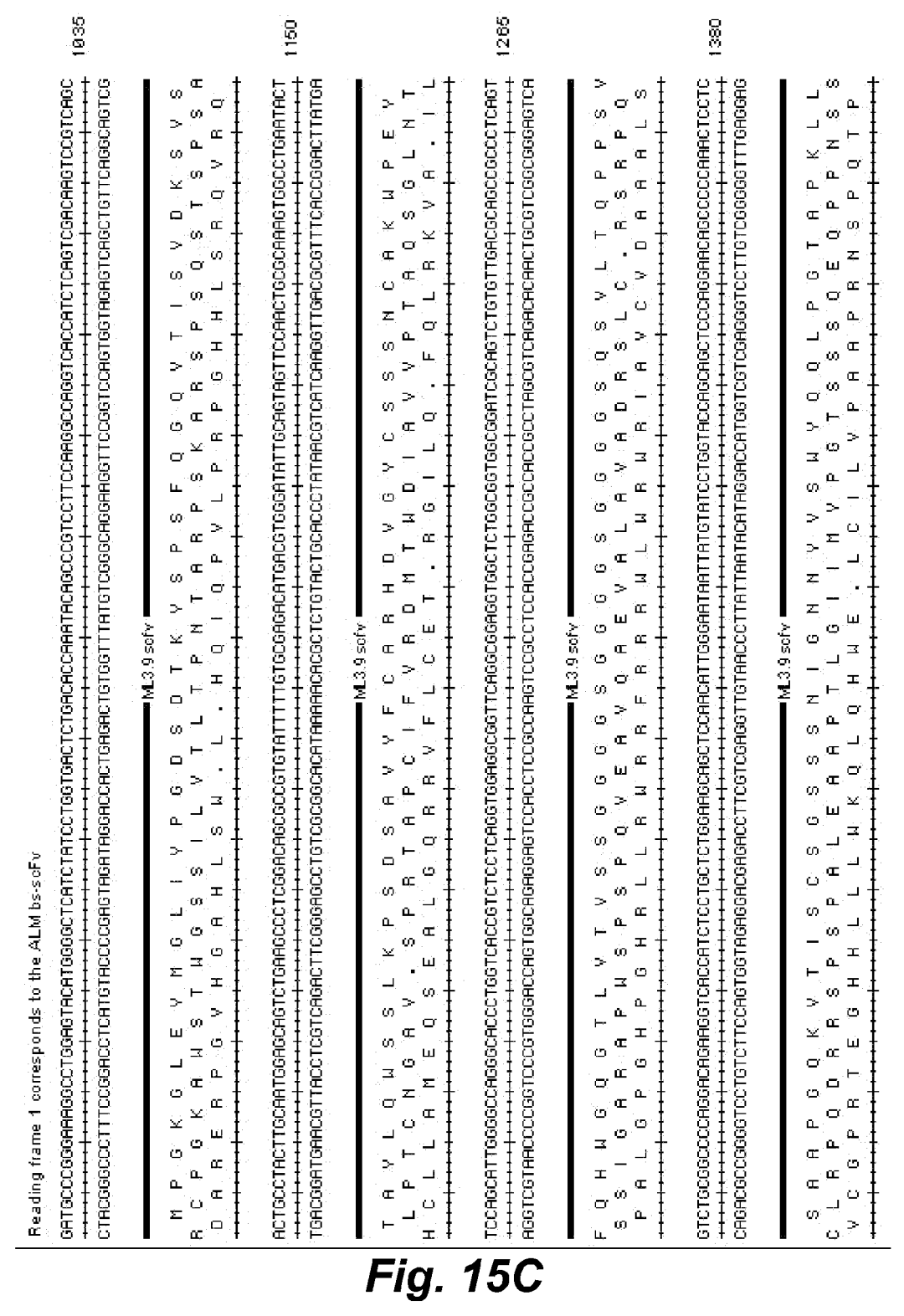
Figure 15D:
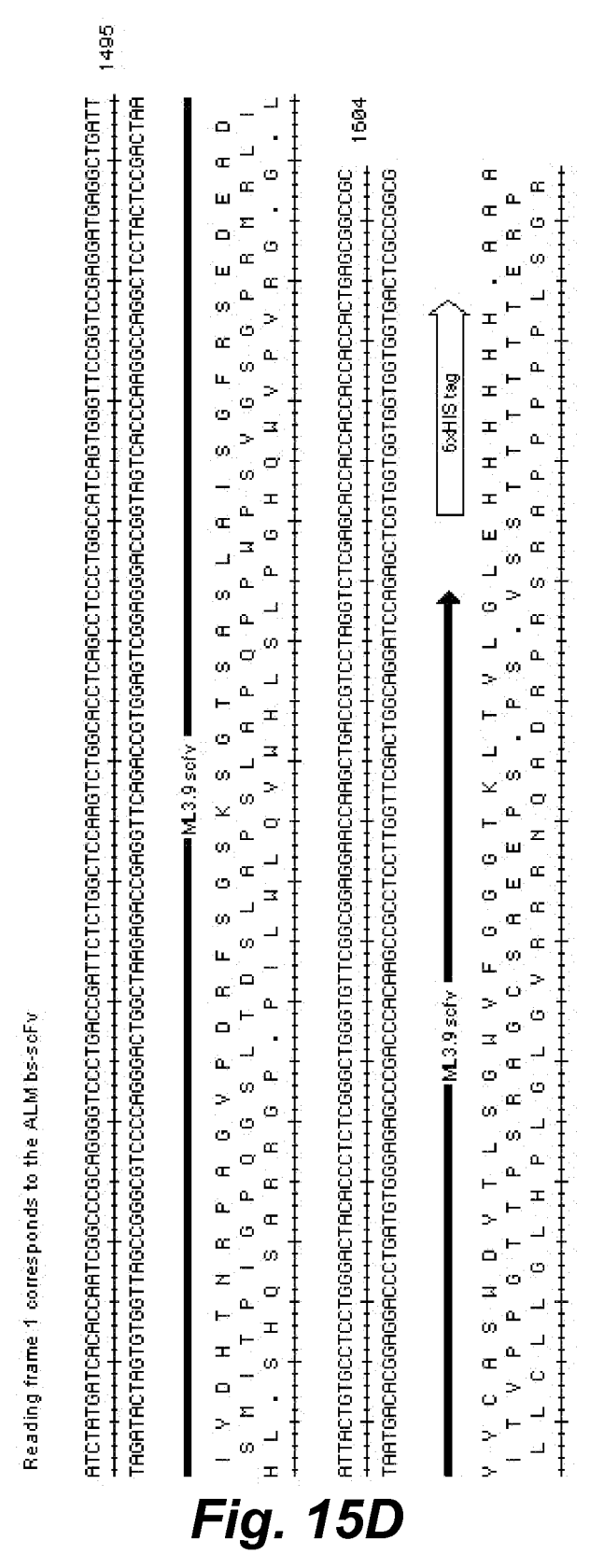

FIG. 15A-D shows the amino acid sequence of the ALM (A5-ML3.9) bispecific scFv (DNA: SEQ ID NO:26, peptide: SEQ ID NO:27). Alternate reading frames 2 (DNA: SEQ ID NO:28, peptide: SEQ ID NO:29) and 3 (DNA: SEQ ID NO:30, peptide: SEQ ID NO:31) are also shown.

FIG. 16 shows the amino acid sequence of anti-EGFR antibodies. The figure shows the VH domains of C10 (SEQ ID NO:32), and E12 (SEQ ID NO:33), and the VL domains of C10 (SEQ ID NO:34) and E12 (SEQ ID NO:35).

FIGS. 17A and 17B show amino acid sequences for the VH and VL regions of anti-Her2 antibodies. FIG. 17A shows VH amino acid sequences for C6.5 (SEQ ID NO:36), G98A (SEQ ID NO:37), ML3-9 (SEQ ID NO:38), H3B1 (SEQ ID NO:39), B1D2 (SEQ ID NO:40), F5 (SEQ ID NO:41), and F5B6H2 (SEQ ID NO:42). FIG. 17B shows VL amino acid sequences for C6.5 (SEQ ID NO:43), G98A (SEQ ID NO:44), ML3-9 (SEQ ID NO:45), H3B1 (SEQ ID NO:46), B1D2 (SEQ ID NO:47), F5 (SEQ ID NO:48), and F5B6H2 (SEQ ID NO:49).

FIGS. 18A and 18B show the amino acid sequences for anti-HER3 antibodies. FIG. 18A shows amino acid sequences for the VH domains of the A5 (SEQ ID NO:50), B12 (SEQ ID NO:51), E12 (SEQ ID NO:52), F4 (SEQ ID NO:53), and H3 (SEQ ID NO:54) antibodies. FIG. 18B shows amino acid sequences for the VL domains of the A5 (SEQ ID NO:55), B12 (SEQ ID NO:56), E12 (SEQ ID NO:57), F4 (SEQ ID NO:58), and H3 (SEQ ID NO:59) antibodies.

FIG. 19 shows the amino acid sequence for the VH (SEQ ID NO:60) and the VL (SEQ ID NO:61) domains of the anti-HER4 antibody B6.

DETAILED DESCRIPTION

Figure 1:
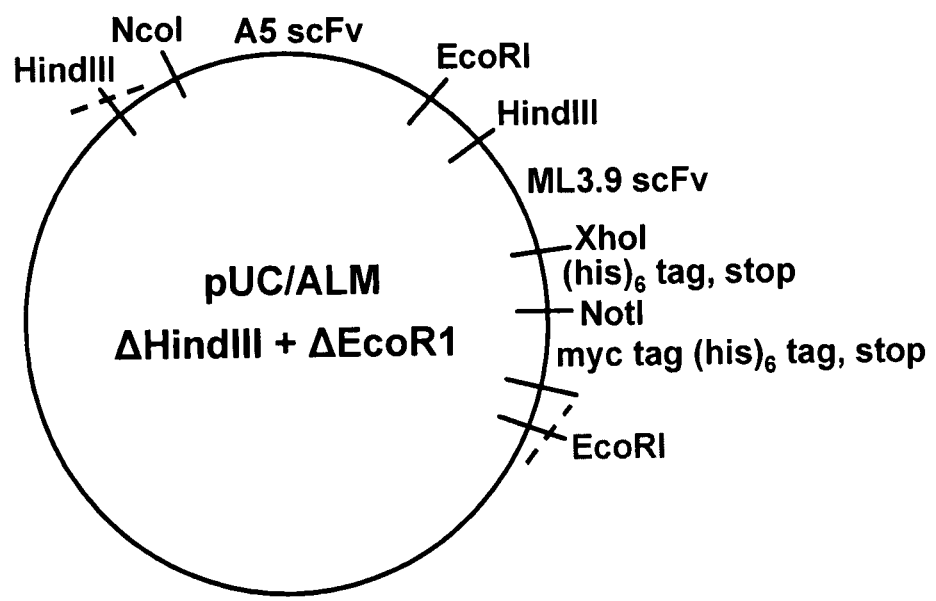
FIG. 1 shows a schematic diagram of the pUC/ALM vector.

Tumors often overexpress growth factor receptors that bind various ligands ligand and facilitate unrestricted tumor growth. One example of such growth factor receptors are the receptors of the Epidermal Growth Factor Receptor (EGFR) protein family.

Signal transduction through members of the Epidermal Growth Factor Receptor (EGFR) protein family is dependent upon the formation of homodimers or heterodimers triggered by the binding of ligand. This receptor family is comprised of four membrane-bound proteins: EGFR, HER2/neu, HER3 and HER4. Overexpression of these proteins has been correlated with a poor prognosis in a number of types of cancer, including, but not limited to, breast, colon, ovarian, endometrial, gastric, pancreatic, prostate and salivary gland cancers. While a number of groups have developed strategies to target individual members of the EGFR protein family (e.g., HER2/neu or EGFR) to inhibit tumor growth, none of the treatments has been proven to ultimately cure these forms of cancer.

In accordance with this invention, in certain embodiments, novel antibodies are provided that specifically or preferentially bind to members of the Epidermal Growth Factor Receptor (EGFR) family of proteins and that can be used to advantage in the detection and/or treatment of various cancers that overexpress the Epidermal Growth Factor Receptor (EGFR) family of proteins. In various embodiments the antibodies themselves can be contacted to such neoplastic cells whereby they inhibit growth and/or proliferation of such cells. Alternatively, the antibodies can be attached to an effector (e.g., detectable label, a cytotoxin, an epitope tag, a second antibody, etc.) whereby the effector can act to inhibit growth and/or proliferation of the target cells or can be used to detect and/or visualize the cells. In certain embodiments the effector is a second antibody thereby forming a bispecific antibody.

In various embodiments the bispecific antibody constructs are capable of simultaneously targeting multiple members (or multiple sites on a given member) of the EGFR protein family. The antibody constructs typically comprise a first antibody and a second antibody joined to each other where the first antibody and the second antibody bind specifically to different epitopes on the same or different members of the EGFR protein family. In certain embodiments, the bispecific antibody constructs are bispecific single chain molecules (e.g., bispecific single chain Fv (bs-scFv)), but the constructs need not be so limited. Thus, for example, chemically conjugated whole antibodies, or antibody fragments are also contemplated within the scope of this invention. In general, where bispecific antibodies are described herein, it will be appreciated that trispecfic, or more generally polyspecific antibodies are also contemplated.

In certain embodiments the bispecific antibodies of this invention bind to selected members of the EGFR protein family (e.g., EGFR, HER2/neu, HER3, HER4) to prevent ligand induced signaling and/or to trigger cytostatic and/or cytotoxic effects. The bispecific antibodies can also be used to specifically label cancer cells, solid tumors, and the like, and, more generally, to specifically target/deliver any conjugated or otherwise coupled effector (e.g., radioisotope, label, cytotoxin, drug, liposome, antibody, nucleic acid, dendrimer, etc.) to cancer cells including but not limited to isolated cancer cells, metastatic cells, solid tumor cells, and the like.

In certain preferred embodiments, the bispecific antibodies of this invention are bispecific single chain Fv antibodies (bs-scFv). Single chain Fv antibody fragments are engineered antibody derivatives that include both a heavy and a light chain variable region joined by a peptide linker molecule and are potentially more effective than unmodified IgG antibodies because their reduced size permits them to penetrate tissues and solid tumors more readily than IgG antibodies.

In one embodiment the bispecific antibodies of this invention (e.g., the bs-scFv antibody molecules) comprise two domains that provide two distinct binding specificities. A first domain can be selected for binding specificity to an epitope on one member of the EGFR protein family and the second domain can be selected for binding specificity for an epitope on a second member of the EGFR protein family. An illustrative bs-scFv molecule of the invention is "ALM"; a bispecific antibody that was created with one arm (domain) that exhibits binding specificity to an epitope on HER2/neu and a second arm (domain) that exhibits binding specificity to an epitope on HER3.

Alternatively, in certain embodiments, the bispecific antibodies of the invention can be generated such that one domain has binding specificity for one epitope on a member of the EGFR protein family and a second domain has binding specificity for a second distinct epitope on the same member of the EGFR protein family. An exemplary bs-scFv of this type is "ALF" which is composed of two distinct scFV molecules, both with a specificity for HER3.

I. Antibodies Forming the Monospecific, Bispecific or Polyspecific Antibodies of this Invention.

As indicated above, in certain embodiments, this invention provides novel isolated antibodies that specifically bind to a member of the EGFR protein family (e.g., EGFR/ErbB1, HER2/neu (ErbB2), HER3 (ErbB3), HER4 (ErbB4). Also, in certain embodiments, this invention a composition comprising these anti-EGFR member antibodies attached to an effector. Where the effector comprise a second (or more) antibodies, a bispecific (or polyspecific) antibody is provided.

In certain embodiments the bispecific or polyspecific antibodies of this invention comprise two or more binding domains (antibodies) at least two of which are specific to different epitopes of the EGFR protein family (e.g., two or more monospecific antibodies). Preferred antibodies of this invention comprise domains specific to epitopes of EGFR, HER2/neu, HER3 and HER4.

Using phage display approaches, a number of single chain antibodies have been raised that are specific to various epitopes on members of the EGFR protein family. These single chain Fv antibodies can be used as domains/arms to construct a bispecific or polyspecific antibody. A number of these antibodies are provided, below, in Table 2 and in the Figures (e.g., FIGS. 13-19).

TABLE 2

Single-chain Fv antibodies directed against epitopes of the EGFR protein family.

| Anti-HER2/neu*: | Anti-HER3**: |
|---|---|
| C6.5*** | HER3.A5 |
| C6ML3-9 (ML3.9 or C6ML3.9) | HER3.F4 |
| C6MH3-B1 (B1 or C6MH3.B1) | HER3.H1 |
| C6-B1D2 (B1D2 or C6MH3-B1D2) | HER.H3 |
| F5** | HER.E12 |
| F5B6H2 | HER3.B12 |
| Anti-EGFR**: | Anti-HER4: |
| EGFR.E12 | HER4.B4 |
| EGFR.C10 | HER4.G4 |
| EGFR.B11 | HER4.F4 |
| EGFR.E8 | HER4.A8 |
| EGFR.1C10 | HER4.B6 |
|  | HER4.D4 |
|  | HER4.D7 |
|  | HER4.D11 |
|  | HER4.D12 |
|  | HER4.E3 |
|  | HER4.E7 |
|  | HER4.F8 |
|  | HER4.C7 |

*Sequences are disclosed in Schier et al. (1996). *J. Mol. Biol.*, 255(1): 28-43. See also Schier et al. (1995) *Immunotechnology*, 1: 73-81.
**Sequences are provided in Appendix A hereinbelow;
***Sequences are also shown in FIGS. 13-19.

In addition amino acid sequences for the VH and VL domains are listed in Tables 3 and 4, respectively. (SEQ ID NO:62)

TABLE 3

Illustrative VH domains of anti-EGFR family member antibodies.

| Ab | Fr1 | CDR1 | Fr2 | CDR2 | Fr3 | CDR3 | Fr4 |
|---|---|---|---|---|---|---|---|
| A5 | QVQLVQSGGGLVKPGG SLRLSCAASGFSFN (SEQ ID NO: 62) | TYDMN (SEQ ID NO: 63) | WVRQAPGKGLEWVS (SEQ ID NO: 64) | SISSSSSYIYYADSVKG (SEQ ID NO: 65) | RFTISRDNAKNSLY6LQMNSLRAEDT AVYYCAR (SEQ ID NO: 66) | DGVATTPFDY (SEQ ID NO: 67) | WGQGTLVTVSS (SEQ ID NO: 68) |
| F5B6H2 | QVQLVESGGGLVQPGG SLRLSCAASGFTFR (SEQ ID NO: 69) | SYAMS (SEQ ID NO: 70) | WVRQAPGKGLEWVS (SEQ ID NO: 71) | AISGRGDNTYYADSVKG (SEQ ID NO: 72) | RFTISRDNSKNTLYLQMNSLRAEDTA VYYCAR (SEQ ID NO: 73) | MTSNAVGFDY (SEQ ID NO: 74) | WGQGTLVTVSS (SEQ ID NO: 75) |
| B1D2 | QVQLVQSGAEVKKPGE SLKISCKGSGYSFT (SEQ ID NO: 76) | STWIA (SEQ ID NO: 77) | WVRQMPGKGLEYMG (SEQ ID NO: 78) | LIYPGDSDTKYSPSFQG (SEQ ID NO: 79) | QVTISVDKSVSTAYLQWSSLKPSDSA VYYCAR (SEQ ID NO: 80) | HDVGYCTDRTCAKWPEWL GV (SEQ ID NO: 81) | WGQGTLVTVSS (SEQ ID NO: 82) |
| ML3.9 | QVQLVQSGAEVKKPGE SLKISCKGSGYSFT (SEQ ID NO: 83) | STWIA (SEQ ID NO: 84) | WVRQMPGKGLEYMG (SEQ ID NO: 85) | LIYPGDSDTKYSPSFQG (SEQ ID NO: 86) | QVTISVDKSVSTAYLQWSSLKPSDSA VYYCAR (SEQ ID NO: 87) | HDVGYCSSSNCAKWPEYF QH (SEQ ID NO: 88) | WGQGTLVTVSS (SEQ ID NO: 89) |
| B12 (HER3.B12) | QVQLVQSGGGLVQPGR SLRLSCAASGFTFD (SEQ ID NO: 90) | DYAMH (SEQ ID NO: 91) | WVRQAPGKGLEWVS (SEQ ID NO: 92) | GISWNSGSIGYADSVKG (SEQ ID NO: 93) | RFTISRDNAKNSLYLQMNSLRPEDTA VYYCAR (SEQ ID NO: 94) | DLGAKQMLEGFDY (SEQ ID NO: 95) | WGQGTLVTVSS (SEQ ID NO: 96) |
| F4 | QVQLQESGGGLVQPGG SLRLSCAASGFTFS (SEQ ID NO: 97) | SYAMS (SEQ ID NO: 98) | WVRQAPGKGLEWVS (SEQ ID NO: 99) | TISGSGGSTYYADSVKG (SEQ ID NO: 100) | RFTISRDNSKNTLYLQMNSLRAEDTA VYYCAK (SEQ ID NO: 101) | GYSSSESEVASGY (SEQ ID NO: 102) | WGQGTLVTVSS (SEQ ID NO: 103) |
| H3 (HER3.H3) | QVQLQESGGGLVKPGG SLRLSCAASGFTFS (SEQ ID NO: 104) | SYWMS (SEQ ID NO: 105) | WVRQAPGKGLEWMG (SEQ ID NO: 106) | NINRDGSASYYVDSVKG (SEQ ID NO: 107) | RFTISRDNSKAKNSLYLQMNSLRAEDTA VYYCAK (SEQ ID NO: 108) | DRGVGYFDL (SEQ ID NO: 109) | WGRGTLVTVSS (SEQ ID NO: 110) |
| C6.5 | QVQLVQSGAEVKKPGE SLKISCKGSGYSFT (SEQ ID NO: 111) | STWIA (SEQ ID NO: 112) | WVRQMPGKGLEWMG (SEQ ID NO: 113) | LIYPGDSDTKYSPSFQG (SEQ ID NO: 114) | QVTISVDKSVSTAYLQWSSLKPSDSA VYFCAR (SEQ ID NO: 115) | HDVGYCSSSNCSKWPEY FQH (SEQ ID NO: 116) | WGQGTLVTVSS (SEQ ID NO: 117) |
| C6MH3-B1 (HER3.B1) | QVQLVQSGAEVKKPGE SLKISCKGSGYSFT (SEQ ID NO: 118) | STWIA (SEQ ID NO: 119) | WVRQMPGKGLEYMG (SEQ ID NO: 120) | LIYPGDSDTKYSPSFQG (SEQ ID NO: 121) | QVTISVDKSVSTAYLQWSSLKPSDSA VYFCAR (SEQ ID NO: 122) | HDVGYCTDRTCAKWPEY FQH (SEQ ID NO: 123) | WGQGTLVTVSS (SEQ ID NO: 124) |
| EGFR.C10 | EVQLVQSGAEVKKPGS SVKVSCKASGGTFS (SEQ ID NO: 125) | SYAIS (SEQ ID NO: 126) | WVRQAPGQGLEWMG (SEQ ID NO: 127) | GIIPIFGTANYAQKFQG (SEQ ID NO: 128) | RVTITADESTSTAYMELSSLRSEDTA VYYCAR (SEQ ID NO: 129) | EEGPYCSSTSCYGAFDI (SEQ ID NO: 130) | WGQGTLVTVSS (SEQ ID NO: 131) |
| EGFR.E12 | EVQLVQSGAEVKKPGS SVKVSCKASGGTFS (SEQ ID NO: 132) | SYAIS (SEQ ID NO: 133) | WVRQAPGQGLEWMG (SEQ ID NO: 134) | GIIPIFGTANYAQKFQG (SEQ ID NO: 135) | RVTITADESTSTAYMELSSLRSEDTA VYYCAR (SEQ ID NO: 136) | EEGPYCSSTSCYGAFDI (SEQ ID NO: 137) | WGQGTLVTVSS (SEQ ID NO: 138) |
| F5 | QVQLVESGGGLVQPGG SLRLSCAASGFTFR (SEQ ID NO: 139) | SYAMDS (SEQ ID NO: 140) | WVRQAPGKGLEWVS (SEQ ID NO: 141) | AISGRGDNTYYADSVKG (SEQ ID NO: 142) | RFTISRDNSKNTLYLQMNSLRAEDTA VYYCAK (SEQ ID NO: 143) | MTSNAFAFDY (SEQ ID NO: 144) | WGQGTLVTVSS (SEQ ID NO: 145) |

TABLE 3-continued

Illustrative VH domains of anti-EGFR family member antibodies.

| Ab | Fr1 | CDR1 | Fr2 | CDR2 | Fr3 | CDR3 | Fr4 |
|---|---|---|---|---|---|---|---|
| HER3.E12 | QVQLVESGGGVVQPGR SLRLSCAASGFTFS (SEQ ID NO: 146) | DYYIH (SEQ ID NO: 147) | WVRQAPGKGLEWMA (SEQ ID NO: 148) | VISYDGNNKYYAASVKD (SEQ ID NO: 149) | RFTISRDNSKNTVSLQMNSLRAEDTA VYYCAR (SEQ ID NO: 150) | DLYGDYALDY (SEQ ID NO: 151) | WGQGTLVTVSS (SEQ ID NO: 152) |
| HER4.B6 | QVQLVESGGGVVQPGR SLRLSCAASGFTFS (SEQ ID NO: 153) | SYGMH (SEQ ID NO: 154) | WVRQAPGKGLEWVA (SEQ ID NO: 155) | VISYDGSNKYYADSVKG (SEQ ID NO: 156) | RFTISRDNSKNTVSLQMNSLRAEDTA VYYCAK (SEQ ID NO: 157) | YPLN (SEQ ID NO: 158) | WGQGTLVTVSS (SEQ ID NO: 159) |
| G98A. | QVQLVQSGAEVKKPGE SLKISCKGSGYSFT (SEQ ID NO: 160) | SYWIA (SEQ ID NO: 161) | WVRQMPGKGLEYMG (SEQ ID NO: 162) | LIYPGDSDTKYSPSFQ G (SEQ ID NO: 163) | QVTISVDKSVSTAYLQWSSLKPSDSA VYFCAR (SEQ ID NO: 164) | HDVAYCSSSNCAKWPEYF QH (SEQ ID NO: 165) | WGQGTLVTVSS (SEQ ID NO: 166) |

TABLE 4

Illustrative VL domains of anti-EGFR family member antibodies.

| Ab | Fr1 | CDR1 | Fr2 | CDR2 | FR3 | CDR3 | Fr4 |
|---|---|---|---|---|---|---|---|
| A5 | QSVLTQPPSVSGAPGQTVTISC (SEQ ID NO: 167) | TGSSSNIGAGYDVH (SEQ ID NO: 168) | WYQQLPGTAPKLLIY (SEQ ID NO: 169) | GNSNRPS (SEQ ID NO: 170) | GVPDRFSGSKSGTSASLAITGL QAEDEADYYC (SEQ ID NO: 171) | QSYDSSLSAL (SEQ ID NO: 172) | FGGGTKLTVLG (SEQ ID NO: 173) |
| F5B6H2 | QSVLTQPPSVSGAPGQRVTISC (SEQ ID NO: 174) | TGRHSNIGLGYGVH (SEQ ID NO: 175) | WYQQLPGTAPKLLIY (SEQ ID NO: 176) | GNTNRPS (SEQ ID NO: 177) | GVPDRFSGPKGFTSASLAITGL QAEDEADYYC (SEQ ID NO: 178) | QSYDRRTPGWV (SEQ ID NO: 179) | FGGGTKLTVLG (SEQ ID NO: 180) |
| B1D2 | QSVLTQPPSVSQQPGQKVTISC (SEQ ID NO: 181) | SGSSSNIGNNYVS (SEQ ID NO: 182) | WYQQLPGTAPKLLIY (SEQ ID NO: 183) | DHTNRPA (SEQ ID NO: 184) | GVPDRFSGSKSGTSASLAISGF RSEDEADYYC (SEQ ID NO: 185) | ASWDYTLSGWV (SEQ ID NO: 186) | FGGGTKLTVL (SEQ ID NO: 187) |
| ML3.9 | QSVLTQPPSVSAAPGQKVTISC (SEQ ID NO: 188) | SGSSSNIGNNYVS (SEQ ID NO: 189) | WYQQLPGTAPKLLIY (SEQ ID NO: 190) | DHTNRPA (SEQ ID NO: 191) | GVPDRFSGSKSGTSASLAISGF RSEDEADYYC (SEQ ID NO: 192) | ASWDYTLSGWV (SEQ ID NO: 193) | FGGGTKLTVL (SEQ ID NO: 194) |
| B12 | NFMLTQDPAVSVALGQTVRITC (SEQ ID NO: 195) | QGDSLRSYYAS (SEQ ID NO: 196) | WYQQKPGQAPVLVIY (SEQ ID NO: 197) | GKNNRPS (SEQ ID NO: 198) | GIPDRFSGSTSGNSASLTITGA QAEDEADYYC (SEQ ID NO: 199) | NSRDSSGNHWV (SEQ ID NO: 200) | FGGGTKVTVL (SEQ ID NO: 201) |
| F4 | DIVMTQSPSSLSASVGDRVTITC (SEQ ID NO: 202) | RASQGIRNDLG (SEQ ID NO: 203) | WYQQKAGKAPKLLIY (SEQ ID NO: 204) | AASSLQS (SEQ ID NO: 205) | GVPSRFSGSGSGTDFTLTISSL QPDDFATYFC (SEQ ID NO: 206) | QQAHSFPPT (SEQ ID NO: 207) | FGGGTKVEIKR (SEQ ID NO: 208) |
| H3 (HER3.H3) | QSALTQPASVSGSPGQSITISC (SEQ ID NO: 209) | TGTSSDVGGYNFVS (SEQ ID NO: 210) | WYQQHPGKAPKLMIY (SEQ ID NO: 211) | DVSDRPS (SEQ ID NO: 212) | GVSDRFSGSKSGNTASLIISGL QAEDEADYYC (SEQ ID NO: 213) | SSYGSSTHVI (SEQ ID NO: 214) | FGGGTKVTVL (SEQ ID NO: 215) |
| C6.5 | QSVLTQPPSVSQQPGQKVTISC (SEQ ID NO: 216) | SGSSSNIGNNYVS (SEQ ID NO: 217) | WYQQLPGTAPKLLIY (SEQ ID NO: 218) | GHTNRPA (SEQ ID NO: 219) | GVPDRFSGSKSGTSASLAISGF RSEDEADYYC (SEQ ID NO: 220) | AAWDDSLSGWV (SEQ ID NO: 221) | FGGGTKLTVL (SEQ ID NO: 222) |
| C6MH3-B1 (HEB1) | QSVLTQPPSVSQQPGQKVTISC (SEQ ID NO: 223) | SGSSSNIGNNYVS (SEQ ID NO: 224) | WYQQLPGTAPKLLIY (SEQ ID NO: 225) | DHTNRPA (SEQ ID NO: 226) | GVPDRFSGSKSGTSASLAISGF RSEDEADYYC (SEQ ID NO: 227) | ASWDYTLSGWV (SEQ ID NO: 228) | FGGGTKLTVL (SEQ ID NO: 229) |
| EGFR.C10 | QSVLTQDPAVSVALGQTVKITC (SEQ ID NO: 230) | QGDSLRSYFAS (SEQ ID NO: 231) | WYQQKPGQAPTLVMY (SEQ ID NO: 232) | ARNDRPA (SEQ ID NO: 233) | GVPDRFSGSKSGTSASLAISGL QSEDEADYYC (SEQ ID NO: 234) | AAWDDSLNGYL (SEQ ID NO: 235) | FGAGTKLTVL (SEQ ID NO: 236) |
| EGFR.E12 | QSVLTQDPAVSVALGQTVKITC (SEQ ID NO: 237) | QGDSLRSYFAS (SEQ ID NO: 238) | WYQQKPGQAPTLVMY (SEQ ID NO: 239) | ARNDRPA (SEQ ID NO: 240) | GVPDRFSGSKSGTSASLAISGL QSEDEADYYC (SEQ ID NO: 241) | AAWDDSLNGYL (SEQ ID NO: 242) | FGAGTKLTVL (SEQ ID NO: 243) |
| F5 | QSVLTQPPSVSGAPGQTVTISC (SEQ ID NO: 244) | TGSSSNIGAGYGVH (SEQ ID NO: 245) | WYQQLPGTAPKLLIY (SEQ ID NO: 246) | GNTNRPS (SEQ ID NO: 247) | GVPDRFSGFKSGTSASLAITGL QAEDEADYYC (SEQ ID NO: 248) | QSYDSSLSGWV (SEQ ID NO: 249) | FGGGTKLTVL (SEQ ID NO: 250) |

TABLE 4-continued

Illustrative VL domains of anti-EGFR family member antibodies.

| Ab | Fr1 | CDR1 | Fr2 | CDR2 | FR3 | CDR3 | Fr4 |
|---|---|---|---|---|---|---|---|
| HER3.E12 | DIQMTQSPSTLSASLGDRVTITC (SEQ ID NO: 251) | RASQSIGSWLA (SEQ ID NO: 252) | WYQQKPGKAPKLLIY (SEQ ID NO: 253) | KASTLES (SEQ ID NO: 254) | GCPSRFTGSGSGTEFTLTISGL QPEDFATYYC (SEQ ID NO: 255) | QKLSSYPLT (SEQ ID NO: 256) | FGGGTKVEIKR (SEQ ID NO: 257) |
| HER4.B6 | QSALTQPASVSGSPGQSITISC (SEQ ID NO: 258) | TGTSDVGGYNYVS (SEQ ID NO: 259) | WYQQHPGKAPKLMIY (SEQ ID NO: 260) | EVSNRPS (SEQ ID NO: 261) | GVSNRFSGSKSGNTASLTISGL QAEDEADYYC (SEQ ID NO: 262) | NSYTSSSTWV (SEQ ID NO: 263) | FGGGTKLTVL (SEQ ID NO: 264) |
| G98A | QSVLTQPPSVSQPGQKVTISC (SEQ ID NO: 265) | SGSSSNIGNNYVS (SEQ ID NO: 266) | WYQQLPGTAPKLLIY (SEQ ID NO: 267) | GHTNRPA (SEQ ID NO: 268) | GVPDRFSGSKSGTSASLAISGF RSEDEADYYC (SEQ ID NO: 269) | AAWDDSLSGWV (SEQ ID NO: 270) | FGGGTKLTVL (SEQ ID NO: 271) |

In various embodiments, two or more of these antibodies can be paired to form either a bs-scFv antibody with binding specificity for two distinct epitopes on different members of the EGFR protein family or a bs-scFv antibody with binding specificity for two distinct epitopes on the same member of the EGFR protein family.

A) Identification of Other Antibodies Binding the Same Epitope(s) as Antibodies the Illustrated Anti-EGFR Family Member Antibodies.

The antibodies of this invention need not be limited to the use of the particular antibodies enumerated in Tables 2-4 and/or shown in the Figures herewith. In effect, each of these identifies an epitope of a member of the EGFR protein family and these antibodies can readily be used to identify other antibodies that bind to the same epitopes. Thus, in certain embodiments, the antibodies of this invention comprise one or more antibodies that specifically bind an epitope specifically bound by an antibody of Tables 2-4 and/or shown in the Figures herewith (e.g., an antibody selected from the group consisting of C6.5, C6ML3-9, C6 MH3-B1, C6-B1D2, F5, HER3.A5, HER3.F4, HER3.H1, HER3.H3, HER3.E12, HER3.B12, EGFR.E12, EGFR.C10, EGFR.B11, EGFR.E8, HER4.B4, HER4.G4, HER4.F4, HER4.A8, HER4.B6, HER4.D4, HER4.D7, HER4.D11, HER4.D12, HER4.E3, HER4.E7, HER4.F8, F5B6H2, and HER4.C7).

Such antibodies are readily identified by screening whole antibodies, antibody fragments, or single chain antibodies for their ability to compete with the antibodies listed in Table 2 for their ability to bind to a protein comprising the target epitope. In other words, candidate antibodies can be screened for cross-reactivity with the antibodies listed in Tables 2-4 and/or shown in the Figures herewith against the target protein in the EGFR protein family.

In one illustrative embodiment, the antibodies of this invention specifically bind to one or more epitopes recognized by antibodies listed in Tables 2-4 and/or shown in the Figures herewith. In other words, such antibodies are cross-reactive with one of more of these antibodies. Means of assaying for cross-reactivity are well known to those of skill in the art (see, e.g., Dowbenko et al. (1988) *J. Virol.* 62: 4703-4711).

For example, in certain embodiments, cross-reactivity can be ascertained by providing an isolated EGFR family member (e.g., EGFR, HER2/neu, HER3 and HER4 or a fragment thereof) attached to a solid support and assaying the ability of a test antibody to compete with one or more of the antibodies listed in Tables 2-4 and/or shown in the Figures herewith for binding to the target protein. Thus, immunoassays in a competitive binding format are can be used for crossreactivity determinations. For example, in one embodiment, the EGFR family member polypeptide is immobilized to a solid support. Antibodies to be tested (e.g., generated by selection from a phage-display library, or generated in a whole antibody library) are added to the assay compete with one or more of the antibodies listed in Tables 2-4 and/or shown in the Figures herewith for binding to the immobilized polypeptide. The ability of test antibodies to compete with the binding of the antibodies of Tables 2-4 and/or shown in the Figures herewith to the immobilized protein are compared. The percent cross-reactivity above proteins can then calculated, using standard calculations. If the test antibody competes with one or more of the antibodies of Tables 2-4 and/or shown in the Figures herewith and has a binding affinity comparable to or greater than about $1 \times 10^{-8}$ M, more preferably greater than $1 \times 10^{-9}$, or $1 \times 10^{-10}$, or more generally with an affinity equal to or greater than the corresponding (competing) antibody, e.g., of Tables 2-4 and/or shown in the Figures herewith then the antibody is well suited for use in the present invention.

In one illustrative embodiment, cross-reactivity is performed by using surface plasmon resonance in a BIAcore. In a BIAcore flow cell, the EGFR protein is coupled to a sensor chip. With a typical flow rate of 5 ml/min, a titration of 100 nM to 1 μM antibody is injected over the flow cell surface for about 5 minutes to determine an antibody concentration that results in near saturation of the surface. Epitope mapping or cross-reactivity is then evaluated using pairs of antibodies at concentrations resulting in near saturation and at least 100 RU of antibody bound. The amount of antibody bound is determined for each member of a pair, and then the two antibodies are mixed together to give a final concentration equal to the concentration used for measurements of the individual antibodies. Antibodies recognizing different epitopes show an essentially additive increase in the RU bound when injected together, while antibodies recognizing identical epitopes show only a minimal increase in RU. In a particularly preferred embodiment, antibodies are said to be cross-reactive if, when "injected" together they show an essentially additive increase (preferably an increase by at least a factor of about 1.4, more preferably an increase by at least a factor of about 1.6, and most preferably an increase by at least a factor of about 1.8 or 2.

Cross-reactivity at the epitopes recognized by the antibodies listed in Tables 2-4 and/or shown in the Figures herewith can ascertained by a number of other standard techniques (see, e.g., Geysen et al (1987) *J. Immunol. Meth.* 102: 259-274).

In addition, number of the antibodies identified in Table 2 have been sequenced (see, e.g., Tables 3-4 and/or the Figures herewith). The amino acid sequences comprising the complementarity determining regions (CDRs) are therefore known. Using this sequence information, the same or similar complementarity determining regions can be engineered into other antibodies to produce chimeric full size antibodies and/or antibody fragments, e.g., to ensure species compatibility, to increase serum half-life, and the like. A large number of methods of generating chimeric antibodies are well known to those of skill in the art (see, e.g., U.S. Pat. Nos. 5,502,167, 5,500,362, 5,491,088, 5,482,856, 5,472,693, 5,354,847, 5,292,867, 5,231,026, 5,204,244, 5,202,238, 5,169,939, 5,081,235, 5,075,431, and 4,975,369).

B) Phage Display Methods to Select Other "Related" Anti-EGFR Family Member Antibodies.

1) Chain Shuffling Methods.

One approach to creating modified single-chain antibody (scFv) gene repertoires has been to replace the original $V_H$ or $V_L$ gene with a repertoire of V-genes to create new partners (chain shuffling) (Clackson et al. (1991) *Nature*. 352: 624-628). Using chain shuffling and phage display, the affinity of a human scFv antibody fragment that bound the hapten phenyloxazoline (phOx) was increased from 300 nM to 1 nM (300 fold) (Marks et al. (1992) *Bio/Technology* 10: 779-783).

Thus, for example, to alter the affinity of an anti-EGFR family member antibody (e.g., A5, F5B6H2, etc.), a mutant scFv gene repertoire can be created containing a $V_H$ gene of the prototypic antibodies (e.g. as shown in Table 3 and/or the figures herewith) and a human $V_L$ gene repertoire (light chain shuffling). The scFv gene repertoire can be cloned into a phage display vector, e.g., pHEN-1 (Hoogenboom et al. (1991) *Nucleic Acids Res.*, 19: 4133-4137) or other vectors and, after transformation, a library of transformants is obtained.

Similarly, for heavy chain shuffling, the anti-EGFR family member antibody (e.g., A5, F5B6H2, etc.) $V_L$ CDR1 and/or CDR2, and/or CDR3 and light chain e.g. as shown in Table 4 and/or the figures herewith) are cloned into a vector containing a human $V_H$ gene repertoire to create a phage antibody library transformants. For detailed descriptions of chain shuffling to increase antibody affinity see Schier et al. (1996) *J. Mol. Biol.*, 255: 28-43, and the like.

2) Site-Directed Mutagenesis to Improve Binding Affinity.

The majority of antigen contacting amino acid side chains are typically located in the complementarity determining regions (CDRs), three in the $V_H$ (CDR1, CDR2, and CDR3) and three in the $V_L$ (CDR1, CDR2, and CDR3) (Chothia et al. (1987) *J. Mol. Biol.*, 196: 901-917; Chothia et al. (1986) *Science*, 233: 755-758; Nhan et al. (1991) *J. Mol. Biol.*, 217: 133-151). These residues contribute the majority of binding energetics responsible for antibody affinity for antigen. In other molecules, mutating amino acids which contact ligand has been shown to be an effective means of increasing the affinity of one protein molecule for its binding partner (Lowman et al. (1993) *J. Mol. Biol.*, 234: 564-578; Wells (1990) *Biochemistry*, 29: 8509-8516). Site-directed mutagenesis of CDRs and screening against the cells overexpressing one or more EGFR family members can produce antibodies having improved binding affinity.

3) CDR Randomization to Produce Higher Affinity Human scFv.

In an extension of simple site-directed mutagenesis, mutant antibody libraries can be created where partial or entire CDRs are randomized ($V_L$ CDR1 CDR2 and/or CDR3 and/or $V_H$ CDR1, CDR2 and/or CDR3). In one embodiment, each CDR is randomized in a separate library, using a known antibody (e.g., UA20, UA8, 585I41, 585I41.1, 585I56, 3076, 3051, M49R, RCI-14, II79_4, II79_3, T5II-4B.1, T5II-4B.2, RCI-11, RCI-20, CI-11A, CI-14A, and/or S95-2) as a template. The CDR sequences of the highest affinity mutants from each CDR library are combined to obtain an additive increase in affinity. A similar approach has been used to increase the affinity of human growth hormone (hGH) for the growth hormone receptor over 1500 fold from $3.4 \times 10^{-10}$ to $9.0 \times 10^{-13}$ M (Lowman et al. (1993) *J. Mol. Biol.*, 234: 564-578).

$V_H$ CDR3 often occupies the center of the binding pocket, and thus mutations in this region are likely to result in an increase in affinity (Clackson et al. (1995) *Science*, 267: 383-386). In one embodiment, four $V_H$ CDR3 residues are randomized at a time using the nucleotides NNS (see, e.g., Schier et al. (1996) *Gene*, 169: 147-155; Schier and Marks (1996) *Human Antibodies and Hybridomas*. 7: 97-105, 1996; and Schier et al. (1996) *J. Mol. Biol.* 263: 551-567).

C) Creation of Other Antibody Forms.

Using the known and/or identified sequences (e.g. $V_H$ and/or $V_L$ sequences) of the single chain antibodies provided herein other antibody forms can readily be created. Such forms include, but are not limited to multivalent antibodies, full antibodies, scFv, (scFv')$_2$, Fab, (Fab')$_2$, chimeric antibodies, and the like.

1) Creation of Homodimers.

For example, to create (scFv')$_2$ antibodies, two scFvs are joined, either directly, or through a linker (e.g., a carbon linker, a peptide, etc.), or through a disulfide bond between, for example, two cysteins. Thus, for example, to create disulfide linked scFv, a cysteine residue can be introduced by site directed mutagenesis at the carboxy-terminus of the antibodies described herein.

An scFv can be expressed from this construct, purified by IMAC, and analyzed by gel filtration. To produce (scFv')$_2$ dimers, the cysteine is reduced by incubation with 1 mM 3-mercaptoethanol, and half of the scFv blocked by the addition of DTNB. Blocked and unblocked scFvs are incubated together to form (scFv')$_2$ and the resulting material can be analyzed by gel filtration. The affinity of the resulting dimer can be determined using standard methods, e.g. by BIAcore.

In one particularly preferred embodiment, the (scFv')$_2$ dimer is created by joining the scFvs fragments through a linker, more preferably through a peptide linker. This can be accomplished by a wide variety of means well known to those of skill in the art. For example, one preferred approach is described by Holliger et al. (1993) *Proc. Natl. Acad. Sci. USA*, 90: 6444-6448 (see also WO 94/13804).

It is noted that using the $V_H$ and/or $V_L$ sequences provided herein Fabs and (Fab')$_2$ dimers can also readily be prepared. Fab is a light chain joined to $V_H$-$C_H$1 by a disulfide bond and can readily be created using standard methods known to those of skill in the art. The F(ab)'$_2$ can be produced by dimerizing the Fab, e.g. as described above for the (scFv')$_2$ dimer.

2) Chimeric Antibodies.

The antibodies of this invention also include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816,567; Morrison et al. (1984) *Proc. Natl. Acad. Sci.* 81: 6851-6855, etc.).

While the prototypic antibodies provided herein are fully human antibodies, chimeric antibodies are contemplated, particularly when such antibodies are to be used in species other than humans (e.g., in veterinary applications). Chimeric antibodies are antibodies comprising a portions from two different species (e.g. a human and non-human portion). Typically, the antigen combining region (or variable region) of a chimeric antibody is derived from a one species source and the constant region of the chimeric antibody (which confers biological effector function to the immunoglobulin) is derived from another source. A large number of methods of generating chimeric antibodies are well known to those of skill in the art (see, e.g., U.S. Pat. Nos. 5,502,167, 5,500,362, 5,491,088, 5,482,856, 5,472,693, 5,354,847, 5,292,867, 5,231,026, 5,204,244, 5,202,238, 5,169,939, 5,081,235, 5,075,431, and 4,975,369, and PCT application WO 91/0996).

In general, the procedures used to produce chimeric antibodies consist of the following steps (the order of some steps may be interchanged): (a) identifying and cloning the correct gene segment encoding the antigen binding portion of the antibody molecule; this gene segment (known as the VDJ, variable, diversity and joining regions for heavy chains or VJ, variable, joining regions for light chains, or simply as the V or variable region or $V_H$ and $V_L$ regions) may be in either the cDNA or genomic form; (b) cloning the gene segments encoding the human constant region or desired part thereof; (c) ligating the variable region to the constant region so that the complete chimeric antibody is encoded in a transcribable and translatable form; (d) ligating this construct into a vector containing a selectable marker and gene control regions such as promoters, enhancers and poly(A) addition signals; (e) amplifying this construct in a host cell (e.g., bacteria); (f) introducing the DNA into eukaryotic cells (transfection) most often mammalian lymphocytes; and culturing the host cell under conditions suitable for expression of the chimeric antibody.

Antibodies of several distinct antigen binding specificities have been manipulated by these protocols to produce chimeric proteins (e.g., anti-TNP: Boulianne et al. (1984) *Nature*, 312: 643; and anti-tumor antigens: Sahagan et al. (1986) *J. Immunol.*, 137: 1066). Likewise several different effector functions have been achieved by linking new sequences to those encoding the antigen binding region. Some of these include enzymes (Neuberger et al. (1984) *Nature* 312: 604), immunoglobulin constant regions from another species and constant regions of another immunoglobulin chain (Sharon et al. (1984) *Nature* 309: 364; Tan et al., (1985) *J. Immunol.* 135: 3565-3567).

In certain embodiments, a recombinant DNA vector is used to transfect a cell line that produces a cancer specific antibody of this invention. The novel recombinant DNA vector contains a "replacement gene" to replace all or a portion of the gene encoding the immunoglobulin constant region in the cell line (e.g., a replacement gene may encode all or a portion of a constant region of a human immunoglobulin, a specific immunoglobulin class, or an enzyme, a toxin, a biologically active peptide, a growth factor, inhibitor, or a linker peptide to facilitate conjugation to a drug, toxin, or other molecule, etc.), and a "target sequence" that allows for targeted homologous recombination with immunoglobulin sequences within the antibody producing cell.

In another embodiment, a recombinant DNA vector is used to transfect a cell line that produces an antibody having a desired effector function, (e.g., a constant region of a human immunoglobulin) in which case, the replacement gene contained in the recombinant vector may encode all or a portion of a region of an antibody of this invention and the target sequence contained in the recombinant vector allows for homologous recombination and targeted gene modification within the antibody producing cell. In either embodiment, when only a portion of the variable or constant region is replaced, the resulting chimeric antibody can define the same antigen and/or have the same effector function yet be altered or improved so that the chimeric antibody may demonstrate a greater antigen specificity, greater affinity binding constant, increased effector function, or increased secretion and production by the transfected antibody producing cell line, etc.

Regardless of the embodiment practiced, the processes of selection for integrated DNA (via a selectable marker), screening for chimeric antibody production, and cell cloning, can be used to obtain a clone of cells producing the chimeric antibody.

Thus, a piece of DNA that encodes a modification for a monoclonal antibody can be targeted directly to the site of the expressed immunoglobulin gene within a B-cell or hybridoma cell line. DNA constructs for any particular modification can be made to alter the protein product of any monoclonal cell line or hybridoma. The level of expression of chimeric antibody should be higher when the gene is at its natural chromosomal location rather than at a random position. Detailed methods for preparation of chimeric (humanized) antibodies can be found in U.S. Pat. No. 5,482,856.

3) Intact Human Antibodies.

In another embodiment, this invention provides for intact, fully human antibodies. Such antibodies can readily be produced in a manner analogous to making chimeric human antibodies. In this instance, instead of using a recognition function derived, e.g. from a murine, the fully human recognition function (e.g., VH and $V_L$) of the antibodies described herein is utilized.

4) Diabodies.

In certain embodiments, this invention contemplates diabodies comprising one or more of the $V_H$ and $V_L$ domains described herein. The term "diabodies" refers to antibody fragments typically having two antigen-binding sites. The fragments typically comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161, and Holliger et al. (1993) *Proc. Natl. Acad. Sci. USA* 90: 6444-6448.

In short, using routine methods, the antibodies listed in Tables 2-3 and/or shown in the Figures herewith can readily be used to generate or identify other antibodies (full length, antibody fragments, single-chain, and the like) that bind to the same epitope. Similarly, the antibodies listed in Tables 2-3 and/or shown in the Figures herewith can readily be utilized to generate other antibodies that have the same or similar complementarity determining regions (CDRs).

II. Preparation of Antibody Molecules.

The antibodies, bispecific antibodies, polyspecific antibodies, and chimeric moieties described herein can be made by methods well known to those of skill in the art.

A) Chemical Synthesis.

Using the sequence information provided herein, for example, the antibodies of this invention (e.g., A5, F5B6H2, etc.), or variants thereof, can be chemically synthesized using well known methods of peptide synthesis. Solid phase synthesis in which the C-terminal amino acid of the sequence is attached to an insoluble support followed by sequential addition of the remaining amino acids in the sequence is one preferred method for the chemical synthesis of single chain antibodies. Techniques for solid phase synthesis are described by Barany and Merrifield, *Solid Phase Peptide Synthesis*; pp. 3-284 in *The Peptides: Analysis, Synthesis, Biology. Vol. 2: Special Methods in Peptide Synthesis*, Part A., Merrifield et al. (1963) *J. Am. Chem. Soc.*, 85: 2149-2156, and Stewart et al. (1984) *Solid Phase Peptide Synthesis*, 2nd ed. Pierce Chem. Co., Rockford, Ill.

B) Recombinant Expression of Antibodies.

In certain preferred embodiments, the antibodies of this invention (e.g., A5, F5B6H2, etc.), or variants thereof, and/or bispecific moieties, etc., are prepared using standard techniques well known to those of skill in the art. Using the sequence information provided herein, nucleic acids encoding the desired antibody can be chemically synthesized according to a number of standard methods known to those of skill in the art. Oligonucleotide synthesis, is preferably carried out on commercially available solid phase oligonucleotide synthesis machines (Needham-VanDevanter et al. (1984) *Nucleic Acids Res.* 12: 6159-6168) or manually synthesized using the solid phase phosphoramidite triester method described by Beaucage et. al. (Beaucage et. al. (1981) *Tetrahedron Letts.* 22(20): 1859-1862). Alternatively, nucleic acids encoding the antibody can be amplified and/or cloned according to standard methods.

Molecular cloning techniques to achieve these ends are known in the art. A wide variety of cloning and in vitro amplification methods are suitable for the construction of recombinant nucleic acids. Examples of these techniques and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); Sambrook et al. (1989) *Molecular Cloning—A Laboratory Manual* (2nd ed.) Vol. 1-3, Cold Spring Harbor Laboratory, Cold Spring Harbor Press, NY, (Sambrook); and *Current*

*Protocols in Molecular Biology*, F. M. Ausubel et al., eds., Current Protocols, a joint venture between Greene Publishing Associates, Inc. and John Wiley & Sons, Inc., (1994 Supplement) (Ausubel). Methods of producing recombinant immunoglobulins are also known in the art. See, Cabilly, U.S. Pat. No. 4,816,567; and Queen et al. (1989) *Proc. Natl Acad. Sci. USA* 86: 10029-10033. In addition, detailed protocols for the expression of antibodies are also provided by Liu et al. (2004) *Cancer Res.* 64: 704-710, Poul et al. (2000) *J. Mol. Biol.* 301: 1149-1161, and the like.

The chimeric and/or bispecific, and/or polyspecific moieties described herein can be prepared using a variety of methods. For example, antibodies can be prepared separately (e.g., using chemical protein synthesis, recombinant expression methods, hybridoma technology, etc.) and then chemically attached to each other, either directly or through a linker. Where the antibody and "effector" are single chain peptides the chimeric moieties can be chemically synthesized, or more preferably recombinantly expressed.

Means of chemically conjugating molecules are well known to those of skill in the art. The procedures for chemically coupling two antibodies are straightforward. Polypeptides typically contain variety of functional groups; e.g., carboxylic acid (COOH) or free amine (—$NH_2$) groups, that are available for reaction with a suitable functional group on the corresponding antibody or on a linker.

Alternatively, the antibodies (and/or other effector(s)) can be derivatized to expose or attach additional reactive functional groups. The derivatization can involve attachment of any of a number of linker molecules such as those available from Pierce Chemical Company, Rockford Ill. A variety of suitable linkers are known to those of skill in the art (see, e.g., European Patent Application No. 188,256; U.S. Pat. Nos. 4,671,958, 4,659,839, 4,414,148, 4,699,784; 4,680,338; 4,569,789; and 4,589,071; and Borlinghaus et al. (1987) *Cancer Res.* 47: 4071-4075) and suitable linkers are also described below with respect to the coupling of effectors to bispecific antibodies.

In certain preferred embodiments of the invention, the bs-scFv antibody molecules are produced by expression of recombinant antibody fragments produced in host cells. The genes for several of the scFv molecules that target various epitopes on members of the EGFR protein family have been cloned (see, e.g. Tables and Figures herein, and Schier et al. (1996) *J. Mol. Biol.*, (1): 28-43) and pairs (or other combinations) of these scFv genes can be operably linked directly or via a linker molecule. The resulting nucleic acid molecules encoding the bs-scFv antibody fragments are inserted into expression vectors and introduced into host cells. The resulting bs-scFv antibody molecules are then isolated and purified from the expression system.

In certain preferred embodiments of the invention, the scFv antibody molecules are paired together with a novel linker molecule designed to protect against proteolytic degradation of the bs-scFv antibody molecules. This linker typically lacks a proteolytic cleavage site and is typically characterized by containing primarily neutral (non-charged) amino acids. One such linker has the sequence: Asn Ser Gly Ala Gly Thr Ser Gly Ser Gly Ala Ser Gly Glu Gly Ser Gly Ser Lys Leu (SEQ ID NO:272).

The scFv antibodies provided in Table 2 are incorporated into new bs-scFv based upon the following factors: (1) descending affinity for a given target, (2) the lack of cross-reactive epitopes (as determined by binding inhibition and sandwich assays on a BIAcore), (3) combinations that target EGFR family member pairs that have not yet been paired, and (4) inclusion of scFv arms that have led to growth inhibition and altered signal transduction when employed in other bs-scFv combinations.

The purity of the bs-scFv antibody molecules of the invention can be assessed using standard methods known to those of skill in the art, including, but not limited to, ELISA, immunohistochemistry, ion-exchange chromatography, affinity chromatography, immobilized metal affinity chromatography (IMAC), size exclusion chromatography, polyacrylamide gel electrophoresis (PAGE), western blotting, surface plasmon resonance and mass spectroscopy.

Using the antibodies, nucleic acid sequences, and other teaching provided herein, bispecific or polyspecific antibodies of this invention can be recombinantly expressed using routine methods such as those set forth in Sambrook et al. (1989) *Molecular Cloning*, Cold Spring Harbor Laboratory, or Ausubel et al. (eds) (1997) *Current Protocols in Molecular Biology*, John Wiley & Sons N.Y. In addition illustrative methods of producing recombinant bispecific single chain antibodies of this invention are set forth in the Examples. To the extent that specific materials are mentioned, it is merely for purposes of illustration and is not intended to limit the invention.

III. Chimeric Moieties.

In many embodiments, the antibodies described herein are capable of inhibiting cancer cell growth and/or proliferation without the use of any additional "effector". However, in certain embodiments, antibodies and/or the bispecific antibodies and/or polyspecific antibodies are additionally coupled to an effector thereby forming chimeric moieties that preferentially target/deliver the effector to a cell overexpressing the EGFR family member or members.

Since EGFR proteins are often found in upregulated in cancer cells, these proteins can be can be exploited as target(s) for the efficient and specific delivery of an effector (e.g., an effector molecule such as a cytotoxin, a radiolabel, etc.) to various cancer cells (e.g., isolated cells, metastatic cells, solid tumor cells, etc.), in particular to epithelial cancer cells (e.g., breast cancer cells). The target EGFR protein(s) need not exist solely on cancer cells to provide an effective target. Differential expression of EGFR on cancer cells, as compared to healthy cells, is sufficient to provide significant and useful targeting advantage, i.e. resulting in preferential delivery of the effector moiety to and/or into the target (e.g., cancer) cell.

In certain preferred embodiments, antibodies, and/or the bispecific or polyspecific antibodies of this invention are utilized in a "pretargeting" strategy (resulting in formation of a chimeric moiety at the target site after administration of the effector moiety) or in a "targeting" strategy where the bispecific and/or polyspecific antibody is coupled to an effector molecule prior to use to provide a chimeric moiety.

A chimeric molecule or chimeric composition or chimeric moiety refers to a molecule or composition wherein two or more molecules or compositions that exist separately in their native state are joined together to form a single molecule moiety or composition having the desired functionality of its constituent members. Typically, one of the constituent molecules of a chimeric moiety is a "targeting molecule". i.e., in the present case an antibody that specifically binds a member of the EGFR family, a bispecific antibody, and/or a polyspecific antibody that specifically binds one or more members of the EGFR family.

It will be noted that in certain embodiments single antibody of this invention can be regarded as a targeting moiety that can be attached to an effector. When the effector is a second antibody this forms a chimeric moiety that can be a bispecific antibody. In other embodiments, the bispecific and/or polyspecific constructs (while themselves chimeric moieties) are used as a targeting moiety and are attached to a "third" effector. Thus use of a polyspecific targeting moiety can, in certain instances, improve specificity for the target cell(s).

As indicated above, the typically chimeric moiety comprises an a targeting moiety (e.g., an antibody, bispecific antibody, etc.) attached to an "effector". The effector refers to a molecule or group of molecules that is to be specifically transported to (or into) the target cell (e.g., a cell overexpressing an EGFR family member). The effector molecule typically has a characteristic activity that is to be delivered to the target cell. Effector molecules include, but are not limited to cytotoxins, labels, radionuclides, ligands, antibodies, drugs, liposomes, and the like.

In certain embodiments, the effector is a detectable label, with preferred detectable labels including radionuclides. Among the radionuclides and labels useful in the radionuclide-chelator—(e.g., biotin) conjugates of the present invention, gamma-emitters, positron-emitters, x-ray emitters and fluorescence-emitters are suitable for localization, diagnosis and/or staging, and/or therapy, while beta and alpha-emitters and electron and neutron-capturing agents, such as boron and uranium, also can be used for therapy.

The detectable labels can be used in conjunction with an external detector and/or an internal detector and provide a means of effectively localizing and/or visualizing, e.g., cancer cells overexpressing one or more EGFR family members. Such detection/visualization can be useful in various contexts including, but not limited to pre-operative and intraoperative settings. Thus, in certain embodiment this invention relates to a method of intraoperatively detecting and locating tissues having EGFR family markers in the body of a mammal. These methods typically involve administering to the mammal a composition comprising, in a quantity sufficient for detection by a detector (e.g., a gamma detecting probe), a bispecific and/or polyspecific antibody of this invention labeled with a detectable label (e.g., anti-EGFR family member antibodies of this invention labeled with a radioisotope, e.g., $^{161}$Tb, $^{123}$I, $^{125}$I, and the like), and, after allowing the active substance to be taken up by the target tissue, and preferably after blood clearance of the label, subjecting the mammal to a radioimmunodetection technique in the relevant area of the body, e.g., by using a gamma detecting probe.

The chimeric moiety comprising an label-bound to an antibody or bispecific antibody of this invention can be used in the technique of radioguided surgery, wherein relevant tissues in the body of a subject can be detected and located intraoperatively by means of a detector, e.g., a gamma detecting probe. The surgeon can, intraoperatively, use this probe to find the tissues in which uptake of the compound labeled with a radioisotope, that is, e.g., a low-energy gamma photon emitter, has taken place.

In addition to detectable labels, preferred effectors include cytotoxins (e.g., *Pseudomonas* exotoxin, ricin, abrin, Diphtheria toxin, and the like), or cytotoxic drugs or prodrugs, in which case the chimeric moiety can act as a potent cell-killing agent specifically targeting the cytotoxin to cells bearing the EGFR family member(s).

In still other embodiments, the effector can include a liposome encapsulating a drug (e.g., an anti-cancer drug such as doxorubicin, vinblastine, taxol, etc.), an antigen that stimulates recognition of the bound cell by components of the immune system, an antibody that specifically binds immune system components and directs them to the target cell(s), and the like.

A) The Bispecific or Polyspecific Anti-EGFR Family Member Targeting Molecule.

In preferred embodiments, of the methods and compositions of this invention, the targeting moiety is an antibody and/or a bispecific and/or polyspecific antibody that specifically binds to one or more members of the EGFR family as described herein. The antibody, bispecific, and/or polyspecific antibody can comprise full-length antibodies, antibody fragment(s) (e.g., Fv, Fab, etc.), and/or single chain antibodies (e.g., scFv).

B) Certain Preferred Effectors.

1) Imaging Compositions.

In certain embodiments, the chimeric molecules of this invention can be used to direct detectable labels to a tumor site. This can facilitate tumor detection and/or localization. In certain particularly preferred embodiments, the effector component of the chimeric molecule is a "radiopaque" label, e.g., a label that can be easily visualized using x-rays. Radiopaque materials are well known to those of skill in the art. The most common radiopaque materials include iodide, bromide or barium salts. Other radiopaque materials are also known and include, but are not limited to organic bismuth derivatives (see, e.g., U.S. Pat. No. 5,939,045), radiopaque polyurethanes (see U.S. Pat. No. 5,346,9810, organobismuth composites (see, e.g., U.S. Pat. No. 5,256,334), radio-opaque barium polymer complexes (see, e.g., U.S. Pat. No. 4,866,132), and the like.

The antibodies (e.g., monospecific, bispecific and/or polyspecific antibodies of this invention) can be coupled directly to the radiopaque moiety or they can be attached to a "package" (e.g., a chelate, a liposome, a polymer microbead, etc.) carrying or containing the radiopaque material as described below.

In addition to radiopaque labels, other labels are also suitable for use in this invention. Detectable labels suitable for use as the effector molecule component of the chimeric molecules of this invention include any composition detectable by spectroscopic, photochemical, biochemical, immunochemical, electrical, optical or chemical means. Useful labels in the present invention include magnetic beads (e.g., Dynabeads™), fluorescent dyes (e.g., fluorescein isothiocyanate, texas red, rhodamine, green fluorescent protein, and the like), radiolabels (e.g., $^{3}$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads.

Various preferred radiolabels include, but are not limited to $^{99}$Tc, $^{203}$Pb, $^{67}$Ga, $^{68}$Ga, $^{72}$As, $^{111}$In, $^{113m}$In, $^{97}$Ru, $^{62}$Cu, $^{641}$Cu, $^{52}$Fe, $^{52m}$Mn, $^{51}$Cr, $^{186}$R, $^{188}$Re, $^{77}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, and $^{111}$Ag.

Means of detecting such labels are well known to those of skill in the art. Thus, for example, radiolabels may be detected using photographic film, scintillation detectors, and the like. Fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

In certain specific embodiments, this invention contemplates the use of immunoconjugates (chimeric moieties) for the detection of tumors and/or other cancer cells. Thus, for example, the bispecific antibodies of this invention can be conjugated to gamma-emitting radioisotopes (e.g., Na-22, Cr-51, Co-60, Tc-99, I-125, I-131, Cs-137, GA-67, Mo-99) for detection with a gamma camera, to positron emitting isotopes (e.g., C-11, N-13, O-15, F-18, and the like) for detection on a Positron Emission Tomography (PET) instrument, and to metal contrast agents (e.g., Gd containing reagents, Eu containing reagents, and the like) for magnetic resonance imaging (MRI), In addition, the bispecific antibodies of this invention can be used in traditional immunohistochemistry (e.g., fluorescent labels, nanocrystal labels, enzymatic and colormetric labels etc.).

2) Radiosensitizers.

In another embodiment, the effector can be a radiosensitizer that enhances the cytotoxic effect of ionizing radiation (e.g., such as might be produced by $^{60}$Co or an x-ray source) on a cell. Numerous radiosensitizing agents are known and include, but are not limited to benzoporphyrin derivative compounds (see, e.g., U.S. Pat. No. 5,945,439), 1,2,4-benzotriazine oxides (see, e.g., U.S. Pat. No. 5,849,738), compounds containing certain diamines (see, e.g., U.S. Pat. No. 5,700,825), BCNT (see, e.g., U.S. Pat. No. 5,872,107), radiosensitizing nitrobenzoic acid amide derivatives (see, e.g., U.S. Pat. No. 4,474,814), various heterocyclic derivatives (see, e.g., U.S. Pat. No. 5,064,849), platinum complexes (see, e.g., U.S. Pat. No. 4,921,963), and the like.

3) Ligands.

In certain embodiments the effector molecule can also comprise a ligand, an epitope tag, or an antibody. Particularly preferred ligand and antibodies are those that bind to surface markers on immune cells. Chimeric molecules utilizing such antibodies as effector molecules act as bifunctional linkers establishing an association between the immune cells bearing binding partner for the ligand or antibody and the tumor cells expressing the EGFR family member(s).

3) Chelates

Many of the pharmaceuticals and/or radiolabels described herein are provided as a chelate, particularly where a pre-targeting strategy is utilized. The chelating molecule is typically coupled to a molecule (e.g., biotin, avidin, streptavidin, etc.) that specifically binds an epitope tag attached to the antibody, and/or bispecific, and/or polyspecific antibody.

Chelating groups are well known to those of skill in the art. In certain embodiments, chelating groups are derived from ethylene diamine tetra-acetic acid (EDTA), diethylene triamine penta-acetic acid (DTPA), cyclohexyl 1,2-diamine tetra-acetic acid (CDTA), ethyleneglycol-O,O'-bis(2-aminoethyl)-N,N,N',N'-tetra-acetic acid (EGTA), N,N-bis(hydroxybenzyl)-ethylenediamine-N,N'-diacetic acid (HBED), triethylene tetramine hexa-acetic acid (TTHA), 1,4,7,10-tetraazacyclododecane-N,N'-,N'',N'''-tetra-acetic acid (DOTA), hydroxyethyldiamine triacetic acid (HEDTA), 1,4,8,11-tetra-azacyclotetradecane-N,N',N'',N'''-tetra-acetic acid (TETA), substituted DTPA, substituted EDTA, and the like.

Examples of certain preferred chelators include unsubstituted or, substituted 2-iminothiolanes and 2-iminothiacyclohexanes, in particular 2-imino-4-mercaptomethylthiolane, and SAPS(N-(4-[211At] astatophenethyl) succinamate).

One chelating agent, 1,4,7,10-tetraazacyclododecane-N,N,N'',N'''-tetraacetic acid (DOTA), is of particular interest because of its ability to chelate a number of diagnostically and therapeutically important metals, such as radionuclides and radiolabels.

Conjugates of DOTA and proteins such as antibodies have been described. For example, U.S. Pat. No. 5,428,156 teaches a method for conjugating DOTA to antibodies and antibody fragments. To make these conjugates, one carboxylic acid group of DOTA is converted to an active ester which can react with an amine or sulfhydryl group on the antibody or antibody fragment. Lewis et al. (1994) *Bioconjugate Chem.* 5: 565-576, describes a similar method wherein one carboxyl group of DOTA is converted to an active ester, and the activated DOTA is mixed with an antibody, linking the antibody to DOTA via the epsilon-amino group of a lysine residue of the antibody, thereby converting one carboxyl group of DOTA to an amide moiety.

Alternatively the chelating agent can be coupled, directly or through a linker, to an epitope tag or to a moiety that binds an epitope tag. Conjugates of DOTA and biotin have been described (see, e.g., Su (1995) *J. Nucl. Med.*, 36 (5 Suppl): 154P, which discloses the linkage of DOTA to biotin via available amino side chain biotin derivatives such as DOTA-LC-biotin or DOTA-benzyl-4-(6-amino-caproamide)-biotin). Yau et al., WO 95/15335, disclose a method of producing nitro-benzyl-DOTA compounds that can be conjugated to biotin. The method comprises a cyclization reaction via transient projection of a hydroxy group; tosylation of an amine; deprotection of the transiently protected hydroxy group; tosylation of the deprotected hydroxy group; and intramolecular tosylate cyclization. Wu et al. (1992) *Nucl. Med. Biol.*, 19(2): 239-244 discloses a synthesis of macrocylic chelating agents for radiolabeling proteins with $^{111}$In and $^{90}$Y. Wu et al. makes a labeled DOTA-biotin conjugate to study the stability and biodistribution of conjugates with avidin, a model protein for studies. This conjugate was made using a biotin hydrazide which contained a free amino group to react with an in situ generated activated DOTA derivative.

4) Cytotoxins.

In various embodiments the effector comprises a cytotoxin. Illustrative cytotoxins include, but are not limited to *Pseudomonas* exotoxins, *Diphtheria* toxins, ricin, abrin, and variants thereof.

*Pseudomonas* exotoxin A (PE) is an extremely active monomeric protein (molecular weight 66 kD), secreted by *Pseudomonas aeruginosa*, which inhibits protein synthesis in eukaryotic cells through the inactivation of elongation factor 2 (EF-2) by catalyzing its ADP-ribosylation (catalyzing the transfer of the ADP ribosyl moiety of oxidized NAD onto EF-2).

The toxin contains three structural domains that act in concert to cause cytotoxicity. Domain Ia (amino acids 1-252) mediates cell binding. Domain II (amino acids 253-364) is responsible for translocation into the cytosol and domain III (amino acids 400-613) mediates ADP ribosylation of elongation factor 2, which inactivates the protein and causes cell death. The function of domain Ib (amino acids 365-399) remains undefined, although a large part of it, amino acids 365-380, can be deleted without loss of cytotoxicity. See Siegall et al. (1989) *J. Biol. Chem.* 264: 14256-14261.

Where the targeting molecule (e.g., anti-EGFR family member antibody) is fused to PE, a preferred PE molecule is one in which domain Ia (amino acids 1 through 252) is deleted and amino acids 365 to 380 have been deleted from domain Ib. However all of domain Ib and a portion of domain II (amino acids 350 to 394) can be deleted, particularly if the deleted sequences are replaced with a linking peptide such as GGGGS (SEQ ID NO:273).

In addition, the PE molecules can be further modified using site-directed mutagenesis or other techniques known in the art, to alter the molecule for a particular desired application. Means to alter the PE molecule in a manner that does not substantially affect the functional advantages provided by the PE molecules described here can also be used and such resulting molecules are intended to be covered herein.

For maximum cytotoxic properties several modifications to the molecule can be made. An appropriate carboxyl terminal sequence to the recombinant molecule is preferred to translocate the molecule into the cytosol of target cells. Amino acid sequences which have been found to be effective include, REDLK (SEQ ID NO:274) (as in native PE), REDL (SEQ ID NO:275), RDEL (SEQ ID NO:276), or KDEL (SEQ ID NO:277), repeats of those, or other sequences that function to maintain or recycle proteins into the endoplasmic reticulum, referred to here as "endoplasmic retention sequences". See, for example, Chaudhary et al. (1991) *Proc. Natl. Acad. Sci. USA* 87:308-312 and Seetharam et al, *J. Biol. Chem.* 266: 17376-17381. Preferred forms of PE comprise the PE molecule designated PE38QQR. (Debinski et al. *Bioconj. Chem.*, 5: 40 (1994)), and PE4E (see, e.g., Chaudhary et al. (1995) *J. Biol. Chem.*, 265: 16306).

Methods of cloning genes encoding PE fused to various ligands are well known to those of skill in the art (see, e.g., Siegall et al. (1989) *FASEB J.*, 3: 2647-2652; and Chaudhary et al. (1987) *Proc. Natl. Acad. Sci. USA*, 84: 4538-4542).

Like PE, diphtheria toxin (DT) kills cells by ADP-ribosylating elongation factor 2 thereby inhibiting protein synthesis. Diphtheria toxin, however, is divided into two chains, A and B, linked by a disulfide bridge. In contrast to PE, chain B of DT, which is on the carboxyl end, is responsible for receptor binding and chain A, which is present on the amino end, contains the enzymatic activity (Uchida et al. (1972) *Science*, 175: 901-903; Uchida et al. (1973) *J. Biol. Chem.*, 248: 3838-3844).

In a preferred embodiment, the targeting molecule-Diphtheria toxin fusion proteins of this invention have the native receptor-binding domain removed by truncation of the Diphtheria toxin B chain. Particularly preferred is DT388, a DT in which the carboxyl terminal sequence beginning at residue 389 is removed. Chaudhary et al. (1991) *Bioch. Biophys. Res. Comm.*, 180: 545-551. Like the PE chimeric cytotoxins, the DT molecules may be chemically conjugated to the MUC-1 antibody, but, in certain preferred embodiments, the targeting molecule will be fused to the Diphtheria toxin by recombinant means (see, e.g., Williams et al. (1990) *J. Biol. Chem.* 265: 11885-11889).

5) Other Therapeutic Moieties.

Other suitable effector molecules include pharmacological agents or encapsulation systems containing various pharmacological agents. Thus, the targeting molecule of the chimeric molecule may be attached directly to a drug that is to be delivered directly to the tumor. Such drugs are well known to those of skill in the art and include, but are not limited to, doxorubicin, vinblastine, genistein, an antisense molecule, an RNAi molecule, and the like.

Alternatively, the effector molecule may be an encapsulation system, such as a viral capsid, a liposome, or micelle that contains a therapeutic composition such as a drug, a nucleic acid (e.g., an antisense nucleic acid), or another therapeutic moiety that is preferably shielded from direct exposure to the circulatory system (e.g. an anti-cancer drug such as abraxane, doxorubicin, pamidronate disodium, anastrozole, exemestane, cyclophosphamide, epirubicin, toremifene, letrozole, trastuzumab, megestroltamoxifen, paclitaxel, docetaxel, capecitabine, goserelin acetate, zoledronic acid, vinblastine, etc.), an antigen that stimulates recognition of the bound cell by components of the immune system, an antibody that specifically binds immune system components and directs them to the prostate cancer, and the like.

C) Attachment of the Targeting Molecule to the Effector Molecule.

One of skill will appreciate that the antibody, and/or bispecific and/or polyspecific antibody of this invention and the effector moieties can typically be joined together in any order. Thus, for example, where the targeting molecule is a single chain protein the effector molecule may be joined to either the amino or carboxy termini of the targeting molecule. The effector can also be joined to an internal region of the monospecific and/or bispecific and/or polyspecific antibody, or conversely. Similarly, the monospecific, and/or bispecific and/or polyspecific antibody can be joined to an internal location or a terminus of the effector molecule. In any case, attachment points are selected that do not interfere with the respective activities of the monospecific, bispecific and/or polyspecific antibody or the effector.

The bispecific and/or polyspecific antibody and the effector molecule can be attached by any of a number of means well known to those of skill in the art. Typically the effector molecule is conjugated, either directly or through a linker (spacer), to the bispecific antibody. However, where both the effector molecule and the bispecific antibody are both polypeptides it is preferable to recombinantly express the chimeric molecule as a single-chain fusion protein.

1) Conjugation of the Effector Molecule to the Targeting Molecule.

In one embodiment, the antibody, bispecific and/or polyspecific antibody is chemically conjugated to the effector molecule (e.g., a cytotoxin, a label, a ligand, a drug, an antibody, a liposome, etc.). Means of chemically conjugating molecules are well known to those of skill.

The procedure for attaching an agent to an antibody or other polypeptide targeting molecule will vary according to the chemical structure of the agent. Polypeptides typically contain variety of functional groups; e.g., carboxylic acid (COOH) or free amine ($-NH_2$) groups, which are available for reaction with a suitable functional group on an effector molecule to bind the effector thereto.

Alternatively, the bispecific antibody and/or effector molecule can be derivatized to expose or attach additional reactive functional groups. The derivatization can involve attachment of any of a number of linker molecules such as those available from Pierce Chemical Company, Rockford Ill.

A "linker", as used herein, is a molecule that is used to join the targeting molecule to the effector molecule. The linker is capable of forming covalent bonds to both the targeting molecule and to the effector molecule. Suitable linkers are well known to those of skill in the art and include, but are not limited to, straight or branched-chain carbon linkers, heterocyclic carbon linkers, or peptide linkers. Where a monospecific, and/or bispecific and/or polyspecific antibody and the effector molecule are polypeptides, the linkers can be joined to the constituent amino acids through their side groups (e.g., through a disulfide linkage to cysteine). However, in a preferred embodiment, the linkers will be joined to the alpha carbon amino and carboxyl groups of the terminal amino acids.

A bifunctional linker having one functional group reactive with a group on a particular agent, and another group reactive with an antibody, can be used to form the desired immunoconjugate. Alternatively, derivatization can involve chemical treatment of the antibody, e.g., glycol cleavage of a sugar moiety of a glycoprotein antibody with periodate to generate free aldehyde groups. The free aldehyde groups on the antibody can be reacted with free amine or hydrazine groups on an agent to bind the agent thereto. (See U.S. Pat. No. 4,671, 958). Procedures for generation of free sulfhydryl groups on polypeptide, such as antibodies or antibody fragments, are also known (See U.S. Pat. No. 4,659,839).

Many procedures and linker molecules for attachment of various compounds including radionuclide metal chelates, toxins and drugs to proteins such as antibodies are known (see, e.g., European Patent Application No. 188,256; U.S. Pat. Nos. 4,671,958, 4,659,839, 4,414,148, 4,699,784; 4,680,338; 4,569,789; and 4,589,071; and Borlinghaus et al. (1987) *Cancer Res.* 47: 4071-4075). In particular, production of various immunotoxins is well-known within the art and can be found, for example in "Monoclonal Antibody-Toxin Conjugates: Aiming the Magic Bullet," Thorpe et al., *Monoclonal Antibodies in Clinical Medicine*, Academic Press, pp. 168-190 (1982), Waldmann (1991) *Science,* 252: 1657, U.S. Pat. Nos. 4,545,985 and 4,894,443.

In some circumstances, it is desirable to free the effector molecule from the antibody (e.g., monospecific, bispecific and/or polyspecific antibody) when the chimeric moiety has reached its target site. Therefore, chimeric conjugates comprising linkages that are cleavable in the vicinity of the target site can be used when the effector is to be released at the target site. Cleaving of the linkage to release the agent from the antibody may be prompted by enzymatic activity or conditions to which the immunoconjugate is subjected either inside the target cell or in the vicinity of the target site. When the target site is a tumor, a linker which is cleavable under conditions present at the tumor site (e.g., when exposed to tumor-associated enzymes or acidic pH) may be used.

A number of different cleavable linkers are known to those of skill in the art (see, e.g., U.S. Pat. Nos. 4,618,492; 4,542,225, and 4,625,014). The mechanisms for release of an agent from these linker groups include, for example, irradiation of a photolabile bond and acid-catalyzed hydrolysis. U.S. Pat. No. 4,671,958, for example, includes a description of immunoconjugates comprising linkers that are cleaved at the target site in vivo by the proteolytic enzymes of the patient's complement system. In view of the large number of methods that have been reported for attaching a variety of radiodiagnostic compounds, radiotherapeutic compounds, drugs, toxins, and other agents to antibodies one skilled in the art will be able to determine a suitable method for attaching a given agent to an antibody or other polypeptide.

2 Conjugation of Chelates.

In certain preferred embodiments, the effector comprises a chelate that is attached to an antibody or to an epitope tag. The monospecific, and/or bispecific, and/or polyspecific antibody bears a corresponding epitope tag or antibody so that simple contacting of antibody to the chelate results in attachment of the antibody to the effector. The combining step can be performed after the moiety is used (pretargeting strategy) or the target tissue can be bound to the monospecific, bispecific, and/or polyspecific antibody before the chelate is delivered. Methods of producing chelates suitable for coupling to various targeting moieties are well known to those of skill in the art (see, e.g., U.S. Pat. Nos. 6,190,923, 6,187,285, 6,183,721, 6,177,562, 6,159,445, 6,153,775, 6,149,890, 6,143,276, 6,143,274, 6,139,819, 6,132,764, 6,123,923, 6,123,921, 6,120,768, 6,120,751, 6,117,412, 6,106,866, 6,096,290, 6,093,382, 6,090,800, 6,090,408, 6,088,613, 6,077,499, 6,075,010, 6,071,494, 6,071,490, 6,060,040, 6,056,939, 6,051,207, 6,048,979, 6,045,821, 6,045,775, 6,030,840, 6,028,066, 6,022,966, 6,022,523, 6,022,522, 6,017,522, 6,015,897, 6,010,682, 6,010,681, 6,004,533, and 6,001,329).

3) Production of Fusion Proteins.

Where antibody and/or the effector molecule are both single chain proteins and relatively short (i.e., less than about 50 amino acids) they can be synthesized using standard chemical peptide synthesis techniques. Where both components are relatively short the chimeric moiety can be synthesized as a single contiguous polypeptide. Alternatively the antibody and the effector molecule may be synthesized separately and then fused by condensation of the amino terminus of one molecule with the carboxyl terminus of the other molecule thereby forming a peptide bond. Alternatively, the monospecific, bispecific and/or polyspecific antibody and effector molecules can each be condensed with one end of a peptide spacer molecule thereby forming a contiguous fusion protein.

Solid phase synthesis in which the C-terminal amino acid of the sequence is attached to an insoluble support followed by sequential addition of the remaining amino acids in the sequence is the preferred method for the chemical synthesis of the polypeptides of this invention. Techniques for solid phase synthesis are described by Barany and Merrifield, *Solid-Phase Peptide Synthesis*; pp. 3-284 in *The Peptides: Analysis, Synthesis, Biology. Vol. 2: Special Methods in Peptide Synthesis, Part A.*, Merrifield, et al. *J. Am. Chem. Soc.*, 85: 2149-2156 (1963), and Stewart et al., *Solid Phase Peptide Synthesis, 2nd ed.* Pierce Chem. Co., Rockford, Ill. (1984).

In a preferred embodiment, the where the monospecific, and/or bispecific, and/or polyspecific antibody is a single chain polypeptide and the effector is a polypeptide, chimeric fusion proteins of the present invention are synthesized using recombinant DNA methodology. Generally this involves creating a DNA sequence that encodes the fusion protein, placing the DNA in an expression cassette under the control of a particular promoter, expressing the protein in a host, isolating the expressed protein and, if required, renaturing the protein.

DNA encoding the fusion proteins (e.g., ALM-PE38QQR) of this invention may be prepared by any suitable method, including, for example, cloning and restriction of appropriate sequences or direct chemical synthesis by methods such as the phosphotriester method of Narang et al. (1979) *Meth. Enzymol.* 68: 90-99; the phosphodiester method of Brown et al. (1979) *Meth. Enzymol.* 68: 109-151; the diethylphosphoramidite method of Beaucage et al. (1981) *Tetra. Lett.*, 22: 1859-1862; and the solid support method of U.S. Pat. No. 4,458,066.

Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences can be obtained by the ligation of shorter sequences.

Alternatively, subsequences can be cloned and the appropriate subsequences cleaved using appropriate restriction enzymes. The fragments can then be ligated to produce the desired DNA sequence.

In a preferred embodiment, DNA encoding fusion proteins of the present invention may be cloned using DNA amplification methods such as polymerase chain reaction (PCR). Thus, for example, the nucleic acid encoding a bispecific and/or polyspecific antibody is PCR amplified, using a sense primer containing the restriction site for NdeI and an antisense primer containing the restriction site for HindIII. This produces a nucleic acid encoding antibody and having terminal restriction sites. A PE38QQR fragment can be cut out of the plasmid pWDMH4-38QQR or plasmid pSGC242FdN1 described by Debinski et al. (1994) *Int. J. Cancer,* 58: 744-748. Ligation of the antibody and PE38QQR sequences and insertion into a vector produces a vector encoding the monospecific, bispecific and/or polyspecific antibody joined to the amino terminus of PE38QQR (position 253 of PE). The two molecules are joined by a three amino acid junction consisting of glutamic acid, alanine, and phenylalanine introduced by the restriction site.

While the two molecules are preferably essentially directly joined together, one of skill will appreciate that the molecules may be separated by a peptide spacer consisting of one or more amino acids. Generally the spacer will have no specific biological activity other than to join the proteins or to preserve some minimum distance or other spatial relationship between them. However, the constituent amino acids of the spacer can be selected to influence some property of the molecule such as the folding, net charge, or hydrophobicity.

The nucleic acid sequences encoding the fusion proteins can be expressed in a variety of host cells, including E. coli, other bacterial hosts, yeast, and various higher eukaryotic cells such as the COS, CHO and HeLa cells lines and myeloma cell lines. The recombinant protein gene will be operably linked to appropriate expression control sequences for each host. For E. coli this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The plasmids of the invention can be transferred into the chosen host cell by well-known methods such as calcium chloride transformation for E. coli and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant fusion proteins can be purified according to standard procedures of the art, including ammonium sulfate precipitation, affinity columns, column chromatography, gel electrophoresis and the like (see, generally, R. Scopes (1982) *Protein Purification*, Springer-Verlag, N.Y.; Deutscher (1990) *Methods in Enzymology Vol. 182: Guide to Protein Purification.*, Academic Press, Inc. N.Y.). Substantially pure compositions of at least about 90 to 95% homogeneity are preferred, and 98 to 99% or more homogeneity are most preferred for pharmaceutical uses. Once purified, partially or to homogeneity as desired, the polypeptides may then be used therapeutically.

One of skill in the art would recognize that after chemical synthesis, biological expression, or purification, the EGFR polypeptide targeted fusion protein can possess a conformation substantially different than the native conformations of the constituent polypeptides. In this case, it may be necessary to denature and reduce the polypeptide and then to cause the polypeptide to re-fold into the preferred conformation. Methods of reducing and denaturing proteins and inducing re-folding are well known to those of skill in the art (See, Debinski et al. (1993) *J. Biol. Chem.,* 268: 14065-14070; Kreitman and Pastan (1993) *Bioconjug. Chem.,* 4: 581-585; and Buchner, et al. (1992) *Anal. Biochem.,* 205: 263-270).

One of skill would recognize that modifications can be made to the fusion proteins without diminishing their biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids placed on either terminus to create conveniently located restriction sites or termination codons.

IV. Uses of Bispecific Antibody Molecules and/or Chimeric Moieties:

The antibodies of this invention and the bispecific antibodies having affinity for two distinct antigens have broad applications in therapy and diagnosis. For example, the antibodies, and/or the bs-antibody molecules of the invention (e.g., bs-scFv)., can be used: (1) to directly alter the growth of tumors that overexpress members of the EGFR protein family; (2) in combination with other cytotoxic agents (e.g., chemotherapeutic agents, external beam radiation, targeted radioisotopes, and other antibodies or signal transduction inhibitors); and (3) to recruit a variety of different cytotoxic agents or effector cells directly to targeted tumor cells that express members of the EGFR protein family.

Targeting cytotoxic agents or effector cells to specific tumor cells utilizing the antibodies and/or bs-scFv antibody molecules of the invention provides added tumor-directed specificity due to the increased expression of these targets on tumor cells relative to normal tissue. In addition, the bispecific antibodies can bind to multiple receptors or receptor components, thereby cross-linking receptors or receptor components producing a cytotoxic and/or cytostatic effect. Antibody-based agents that only bind to one target on normal tissue will typically not crosslink the receptors and trigger cytotoxic results.

In certain embodiments the bispecific antibodies of this invention show higher avidity to the target cell(s) (as compared to single antibodies) which helps stabilize the antibody/target complex and provide long-term association of the antibody with the cell, thus providing added specificity for the agent on tumor cells that overexpress both targets.

In addition, the binding of antibodies to the members of the EGFR protein family often triggers the internalization of these proteins, making these antibodies effective platforms for the delivery of toxins, drugs, radioisotopes or other cytotoxic agents. For example, the bispecific antibody ALM mediates a reduction in the quantity of HER2/neu and HER3 on the surface of tumor cells, suggesting a similar internalization mechanism. Therefore, the combination of these bs-scFv molecules with cytotoxic or other agents (effectors), e.g., in a chimeric moiety, will result in effective delivery to cells that overexpress both targets, thus increasing the specificity and efficacy of the therapy. By incorporating additional sequences (e.g., Fc receptor targeting arms) that interact with effector cells, a similar increase in targeting specificity can also be incorporated into effector cell-based treatment strategies.

The antibodies or bispecific antibody molecules of the invention can also be used in gene therapy for direct targeting and internalization of nucleic acids encoding therapeutic agents (e.g., pseudomonas exotoxin, diphtheria toxin, various tumor suppressor genes, various labels, etc.), In addition, the bispecific antibodies can be conjugated, e.g., via a chelate to cytotoxic radioactive moieties (e.g., $^{211}$At) to radiation enhancing agents, and to various detectable labels (e.g., radio opaque labels). In addition, the bispecific antibody molecules can be coupled to lipids, liposomes, dendrimers, and the like. The lipids, liposomes and dendrimers can combine with and/or encapsulate various therapeutic moieties (e.g., anticancer drugs including, but not limited to, alkylating agents such as busulfan, chlorambucal, cis-platinum, cyanomorpholino-doxorubicin, etc., antimitotic agents such as allocolchicine, cohchicine, taxol, vinblastine, vincristine, and the like, topoisomerase I inhibitors such as camptothecin, aminocamptothecin, and the like, topoisomerase II inhibitors such as doxorubicin, amonafide, daunorubicin, deoxydoxorubicin, mitoxantrone, and the like, RNA/DNA antimetabolites such as acivicin, ftorafur, methotrexate, trimetrexate, and the like; DNA antimetabolites such as 2'deoxy-5-fluorouridine, cyclocytidine, guanazole, and the like). Lipids, liposomes and dendrimers can also complex with protein therapeutics, nucleic acids encoding, e.g., therapeutic moieties, and the like.

When used as a targeting component of a chimeric moiety, as described above, the antibodies and/or bispecific and/or polyspecific antibodies of this invention preferentially target/deliver the associated effector to the target cell(s) expressing the target EGFR proteins. By increasing the association (e.g., duration of contact or amount of contact) of the effector with the cell (in contact or close proximity), the antibodies of this invention increase the likelihood of the effector internalizing into the cell and/or exerting its characteristic activity on that cell.

Thus, for example, bispecific or polyspecific antibody targeted liposomes or other therapeutic vesicles (liposomes, viruses etc.) show increased exposure (duration/concentration) to target tumors. In an exemplary embodiment, liposomes can be studded by the bs-scFv antibody molecules of the invention to facilitate tumor specific targeting. Anti-cancer agents such as chemotherapeutic agents, antibodies, antisense molecules and/or radioisotopes may be encapsulated in liposomes so modified.

In another embodiment, the antibodies, bispecific antibodies, or polyspecific antibodies (e.g., bs-scFv antibody) can be used to direct gene therapy vectors, including but not limited to modified viruses, to cells that express both target antigens. Viruses can also be utilized to deliver the genes for these bs-scFv antibody molecules to tumor cells where they could be produced and secreted into the cellular microenvironment or, through the addition of additional intracellular targeting sequences, they could be turned into intrabodies that localize to specific cellular compartments and knockout the expression of their targets.

In addition, the molecules of the invention can be used to advantage to detect aberrant expression of members of the EGFR protein family. Such detection can lead to early diagnosis of cancers associated with aberrant tumor growth facilitated by these cell surface proteins. In general, the detection of immunocomplex formation is well known in the art and can be achieved through the application of numerous approaches. These methods are generally based upon the detection of a label or marker, such as any radioactive, fluorescent, biological or enzymatic tags or labels of standard use in the art. U.S. patents concerning the use of such labels include U.S. Pat. Nos. 3,817,837; 3,850,752; 3,939,350; 3,996,345; 4,277,437; 4,275,149 and 4,366,241. Of course, one may find additional advantages through the use of a secondary binding ligand such as a second antibody or a biotin/avidin ligand binding arrangement, as is known in the art.

V. Administration of Antibodies, Bispecific Antibodies and/or Chimeric Moieties.

A) Pharmaceutical Formulations.

The antibodies, bispecific antibodies, or other constructs of the present invention can be formulated as "bulk" compositions useful in the manufacture of non-pharmaceutical compositions (e.g., impure or non-sterile compositions) and/or and pharmaceutical compositions (i.e., compositions that are suitable for administration to a subject or patient (i.e., human or non-human subject) that can be used directly and/or in the preparation of unit dosage forms. In certain embodiments, such compositions comprise a therapeutically effective amount of one or more therapeutic agents (e.g., bispecific and/or polyspecific antibodies, and/or chimeric moieties comprising such antibodies) and a pharmaceutically acceptable carrier.

As indicated above, the agents of this invention can be used in a wide variety of contexts including, but not limited to the detection and/or imaging of tumors or cancer cells, inhibition of tumor growth and/or cancer cell growth and/or proliferation, and the like. One or more bispecific antibodies, and/or functionalized bispecific antibodies, and/or chimeric moieties of this invention can be administered by injection, that is, intravenously, intramuscularly, intracutaneously, subcutaneously, intraduodenally, or intraperitoneally. Also, in certain embodiments, the compounds can be administered by inhalation, for example, intranasally. Additionally, certain compounds can be administered orally, or transdermally.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans, or suitable for administration to an animal or human. The term "carrier" or refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

Generally, the ingredients of the compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be provided as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Pharmaceutical compositions comprising the bispecific antibodies, and/or functionalized bispecific antibodies, and/or chimeric moieties of this invention can be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries that facilitate processing of the molecules into preparations that can be used pharmaceutically. Proper formulation is dependent upon the route of administration chosen.

For topical or transdermal administration, the bispecific antibodies, and/or functionalized bispecific antibodies, and/or chimeric moieties of this invention can be formulated as solutions, gels, ointments, creams, lotion, emulsion, suspensions, etc. as are well-known in the art. Systemic formulations include those designed for administration by injection, e.g., subcutaneous, intravenous, intramuscular, intrathecal or intraperitoneal injection, as well as those designed for transdermal, transmucosal, inhalation, oral or pulmonary administration.

For injection, the bispecific antibodies, and/or functionalized bispecific antibodies, and/or chimeric moieties of this invention can be formulated in aqueous solutions, preferably in physiologically compatible buffers such as Hanks's solution, Ringer's solution, or physiological saline buffer. The solution can contain formulatory agents such as suspending, stabilizing and/or dispersing agents. Alternatively, compositions comprising the iron chelating agent(s) can be in powder form for constitution with a suitable vehicle, e.g., sterile pyrogen-free water, before use.

For transmucosal administration, penetrants appropriate to the barrier to be permeated are used in the formulation. Such penetrants are generally known in the art.

For oral administration, the bispecific antibodies, and/or functionalized bispecific antibodies, and/or chimeric moieties of this invention can be readily formulated by combining the agent(s) with pharmaceutically acceptable carriers well known in the art. Such carriers enable the agent(s) to be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, e.g., lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate.

If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. Additionally, flavoring agents, preservatives, coloring agents and the like can be added.

For buccal administration, the iron chelating agent(s) can take the form of tablets, lozenges, etc. formulated in conventional manner.

For administration by inhalation, bispecific antibodies, and/or functionalized bispecific antibodies, and/or chimeric moieties of this invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of gelatin for use in an inhaler or insufflator may be formulated containing a powder mix of the iron chelating agent(s) and a suitable powder base such as lactose or starch.

The bispecific antibodies, and/or functionalized bispecific antibodies, and/or chimeric moieties of this invention (can also be formulated in rectal or vaginal compositions such as suppositories or retention enemas, e.g., containing conventional suppository bases such as cocoa butter or other glycerides.

In addition to the formulations described previously, the bispecific antibodies, and/or functionalized bispecific antibodies, and/or chimeric moieties of this invention can also be formulated as a depot preparation. Such long acting formulations may be administered by implantation (for example subcutaneously or intramuscularly) or by intramuscular injection. Thus, for example, the agent(s) of this invention can be formulated with suitable polymeric or hydrophobic materials (for example as an emulsion in an acceptable oil) or ion exchange resins, or as sparingly soluble derivatives, for example, as a sparingly soluble salt.

Other pharmaceutical delivery systems can also be employed. Liposomes and emulsions are well known examples of delivery vehicles that may be used to deliver the bispecific antibodies, and/or functionalized bispecific antibodies, and/or chimeric moieties of this invention. Certain organic solvents such as dimethylsulfoxide also may be employed, although usually at the cost of greater toxicity. Additionally, the bispecific antibodies, and/or functionalized bispecific antibodies, and/or chimeric moieties of this invention can be delivered using a sustained-release system, such as semipermeable matrices of solid polymers containing the therapeutic agent. Various sustained-release materials have been established and are well known by those skilled in the art. Sustained-release capsules may, depending on their chemical nature, can release the active agent(s) for a few days, a few weeks, or up to over 100 days. Depending on the chemical nature and the biological stability of the agent(s) additional strategies for stabilization can be employed.

As the bispecific antibodies, and/or functionalized bispecific antibodies, and/or chimeric moieties of this invention may contain charged side chains or termini, they can be included in any of the above-described formulations as the free acids or bases or as pharmaceutically acceptable salts. Pharmaceutically acceptable salts are those salts which substantially retain the biological activity of the free bases and which are prepared by reaction with inorganic acids. Pharmaceutical salts tend to be more soluble in aqueous and other protic solvents than are the corresponding free base forms.

B) Effective Dosages.

The antibodies, bispecific antibodies, and/or functionalized bispecific antibodies, and/or chimeric moieties of this invention will generally be used in an amount effective to achieve the intended purpose (e.g., to image a tumor or cancer cell, to inhibit growth and/or proliferation of cancer cells, etc.). In certain preferred embodiments, the antibodies, bispecific antibodies, and/or functionalized bispecific antibodies, and/or chimeric moieties utilized in the methods of this invention are administered at a dose that is effective to partially or fully inhibit cancer cell proliferation and/or growth, or to enable visualization of a cancer cell or tumor characterized by overexpression of an EGFR family protein. In certain embodiments, dosages are selected that inhibit cancer cell growth and/or proliferation at the 90%, more preferably at the 95%, and most preferably at the 98% or 99% confidence level. Preferred effective amounts are those that reduce or prevent tumor growth or that facilitate cancer cell detection and/or visualization. With respect to inhibitors of cell growth and proliferation, the compounds can also be used prophalactically at the same dose levels.

Typically, the antibodies, bispecific antibodies, and/or functionalized bispecific antibodies, and/or chimeric moieties of this invention, or pharmaceutical compositions thereof, are administered or applied in a therapeutically effective amount. A therapeutically effective amount is an amount effective to reduce or prevent the onset or progression (e.g., growth and/or proliferation) of a cancer cell and/or a tumor. Determination of a therapeutically effective amount is well within the capabilities of those skilled in the art, especially in light of the detailed disclosure provided herein.

For systemic administration, a therapeutically effective dose can be estimated initially from in vitro assays. For example, a dose can be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art. One skilled in the art could readily optimize administration to humans based on animal data.

Dosage amount and interval can be adjusted individually to provide plasma levels of the inhibitors which are sufficient to maintain therapeutic effect.

Dosages for typical therapeutics are known to those of skill in the art. Moreover, such dosages are typically advisorial in nature and may be adjusted depending on the particular therapeutic context, patient tolerance, etc. Single or multiple administrations of the compositions may be administered depending on the dosage and frequency as required and tolerated by the patient.

In certain embodiments, an initial dosage of about 1 µg, preferably from about 1 mg to about 1000 mg per kilogram daily will be effective. A daily dose range of about 5 to about 75 mg is preferred. The dosages, however, can be varied depending upon the requirements of the patient, the severity of the condition being treated, and the compound being employed. Determination of the proper dosage for a particular situation is within the skill of the art. Generally, treatment is initiated with smaller dosages that are less than the optimum dose of the compound. Thereafter, the dosage is increased by small increments until the optimum effect under the circumstance is reached. For convenience, the total daily dosage can be divided and administered in portions during the day if desired. Typical dosages will be from about 0.1 to about 500 mg/kg, and ideally about 25 to about 250 mg/kg.

In cases of local administration or selective uptake, the effective local concentration of the bispecific antibodies and/or chimeric molecules may not be related to plasma concentration. One skilled in the art will be able to optimize therapeutically effective local dosages without undue experimentation. The amount of antibody and/or chimeric moiety will, of course, be dependent on the subject being treated, on the subject's weight, the severity of the affliction, the manner of administration and the judgment of the prescribing physician.

The therapy can be repeated intermittently. In certain embodiments, the pharmaceutical preparation comprising the bispecific antibody molecules cam be administered at appropriate intervals, for example, at least twice a day or more until the pathological symptoms are reduced or alleviated, after which the dosage may be reduced to a maintenance level. The appropriate interval in a particular case would normally depend on the condition of the patient. The therapy can be provided alone or in combination with other drugs, and/or radiotherapy, and/or surgical procedures.

C) Toxicity.

Preferably, a therapeutically effective dose of antibodies, bispecific antibodies, and/or functionalized bispecific antibodies, and/or chimeric moieties of this invention described herein will provide therapeutic benefit without causing substantial toxicity.

Toxicity of the agents described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Agents that exhibit high therapeutic indices are preferred. Data obtained from cell culture assays and animal studies can be used in formulating a dosage range that is not toxic for use in human. The dosage of the bispecific antibodies, and/or functionalized bispecific antibodies, and/or chimeric moieties of this invention preferably lie within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition (see, e.g., Fingl et al. (1975) In: *The Pharmacological Basis of Therapeutics*, Ch.1, p. 1).

VI. Kits.

The present invention further encompasses kits for use in detecting cells expressing or overexpressing members of the EGFR protein family in vivo, and/or in biological samples. Kits are also provided for in inhibiting the growth and/or proliferation of cells expressing or overexpressing members of the Epidermal Growth Factor Family (e.g., cancer cells).

In certain embodiments, the kits comprise one or more antibodies, bispecific and/or polyspecific antibodies of this invention. In certain preferred embodiments, the antibodies are bispecific scFv antibodies. Depending on use, the antibodies can be functionalized with linkers and/or chelators for coupling to an effector (e.g., a radioactive moiety, a liposome, a cytotoxin, another antibody, etc.) as described herein.

In certain embodiments, the kits can comprise the molecules of the invention specific for members of the EGFR protein family as well as buffers and other compositions to be used for detection of the bs-scFv antibody molecules.

The kits can also include instructional materials teaching the use of the antibodies for detecting, e.g., cancer cells, and/or teaching the combination of the antibodies with functionalizing reagents or teaching the use of functionalized antibodies for imaging and/or therapeutic applications. In certain embodiments, the antibody is provided functionalized with a linker and/or a chelator (in one container) along with one or more effectors, e.g., cytotoxins, radioactive labels (in a second container) such that the two components can be separately administered (e.g., in pre-targeting approaches) or such that the two components can be administered shortly before use.

Certain instructional materials will provide recommended dosage regimen, counter indications, and the like. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such.

EXAMPLES

The following examples are offered to illustrate, but not to limit the claimed invention.

Example 1

Preparation of Bs-Scfv Antibody Molecules

Overexpression of EGFR and HER2/neu has been correlated with a poor prognosis in many solid tumors. Antibodies that perturb signaling through these receptors, such as Herceptin[7] (anti-HER2) and C225 (anti-EGFR), have demonstrated significant utility in the treatment of cancer. Signal transduction through members of the EGFR family (EGFR, Her-2/neu, Her3 and Her4) is dependent upon the formation of homodimers, heterodimers or heterogenous multimers of these receptors triggered by the binding of ligand. Bispecific scFv antibody molecules that engage multiple epitope pairs of these receptor proteins have been generated as described herein below for use in preventing formation of these signaling complexes in cancerous tumor cells.

Materials and Methods:

The following materials and methods are provided to facilitate the practice of the present invention:

Cloning:

The genes coding for single chain Fv (scFv) antibody molecules specific for the different members of the EGFR family (EGFR, HER2/neu, HER3, HER4) were obtained from Dr. Jim Marks (University of California San Francisco). The scFv genes were isolated from large naïve human scFv libraries. The scFv genes specific for the EGFR proteins were isolated by selection against the extracellular domains of these proteins. All of the scFv genes were provided as inserts in a pUC119myc/his vector, between the NcoI and NotI restriction sites. Sequences for the VH and VL domains of the scFv are provided herein.

Construction of a 20 Amino Acid Linker Molecule.

Proteolytic degradation of the bs-scFv antibody molecules in circulation may limit their effectiveness. Thus, a novel 20 amino acid linker that was devoid of all known proteolytic sites was designed and synthesized. The amino acids employed in the construction of the linker were selected to be primarily neutral (not charged, hydrophobic or hydrophilic) to facilitate efficient transport of the protein into the bacterial periplasmic space. The following two primers were synthesized which encode the new linker molecule: LW583 (5'-AAT TCA GGT GCT GGT ACT TCA GGT TCA GGT GCT TCA GGT GAA GGT TCA GGT TCA A-3', (SEQ ID NO:278); and LW584 (5'-AGC TTT GAA CCT GAA CCT TCA CCT GAA GCA CCT GAA CCT GAA GTA CCA GCA CCT G-3', SEQ ID NO:279).

Hybridization of these oligonucleotides formed a "sticky" ends linker with EcoRI and HindIII digested ends. This product was inserted into the pET20b(+) vector previously digested with EcoRI and HindIII. Plasmid DNA was generated from transformed DH5α E. coli using a commercially available kit for DNA plasmid isolation and purification (Qiagen or Gibco BRL Co.) and was subsequently named "pET20b(+)/Linker". The linker molecule is encoded by the following nucleic acid sequence: 5'-AAT TCA GGT GCT GGT ACT TCA GGT TCA GGT GCT TCA GGT GAA GGT TCA GGT TCA AAG CTA-3' (SEQ ID NO:280)), and the resulting linker molecule has the following amino acid sequence: NSG AGT SGS GAS GEG SGS KL(SEQ ID NO:281).

Cloning Anti-HER3 Gene into pET20b(+)/Linker Vector.

The gene coding for the anti-HER3 scFv antibody molecule, A5, was amplified from the A5-pUC119myc/his plasmid with the following two primers: LW687 (5'-CGA CCA TGG CCC AGG TGC AGC TGG TGC AG-3', SEQ ID NO:282); and LW688 (5'-CGA ATT CAC CTA GGA CGG TCA GCT TGG-3', SEQ ID NO:283).

The amplified product and vector, pET20b(+)/Linker, were both digested with NcoI and EcoRI enzymes, ligated and transformed into competent DH5α E. coli for plasmid DNA production. Selected enzymes directed the A5 gene upstream from the linker. The new plasmid, called "pET20b(+)A5/Linker", was then isolated and purified.

Cloning Anti HER2/Neu Gene into pET20b(+)A5/Linker Vector.

The gene coding for the anti-HER2/neu scFv antibody molecule, ML3.9, was amplified from the ML3.9-pUC119myc/his plasmid using the following two primers: LW697 (5'-GGG AAG CTT CAG GTG CAG CTG GTG CAG TCT GG-3', SEQ ID NO:284); and LW698 (5'-GGG CTC GAG ACC TAG GAC GGT CAG CTT GGT TCC-3', SEQ ID NO:285).

The PCR amplified product and plasmid DNA, pET20b(+)A5/Linker, were digested with HindIII and XhoI restriction enzymes, ligated and transformed into competent DH5α E. coli for production of the new plasmid DNA, pET20b(+)A5/Linker/ML3.9. Selected enzymes directed the ML3.9 gene downstream from the linker sequence. The new plasmid, called ApET20b(+)A5/Linker/ML3.9", was then isolated and purified.

Cloning of the A5/Linker/ML3.9 Gene into pUC119/Myc/His Vector.

The nucleic acid molecule encoding the bs-scFv product from pET20b(+) was cloned into a pUC119myc/his vector. A (histidine)$_6$ (SEQ ID NO:286) tag and one "stop" codon, which are part of the pET vector, were amplified together with the A5/Linker/ML3.9 nucleic acid construct. PCR amplification was performed using the following two primers: LW687 (5'-CGA CCA TGG CCC AGG TGC AGC TGG TGC AG-3', SEQ ID NO:287); and LW686 (5'-GAT ATA ATG CGG CCG CTC AGT GGT GGT GGT GGT G-3', (SEQ ID NO:288).

Digestion of the pUC119myc/his vector and amplified product with NcoI and NotI enzymes was followed by a ligation step and transformation of the DH5α E. coli. The resulting plasmid DNA, called "pUC/ALM", was then purified and isolated (FIG. 1).

B. Transformation of the Expression Clone, TG1.

pUC/ALM was transformed into E. coli strain, TG1, and the clones producing the A5/Linker/ML3.9 bs-scFv antibody molecules were isolated as follows. The bs-scFv molecules were dialyzed overnight, purified by immobilized metal affinity chromatography using Ni-NTA resin (Qiagen), followed by size-exclusion chromatography on an HPLC system using a Superdex-75 column (Pharmacia).

Results:

As a proof of concept, two different bs-scFv antibody molecules were created. The first, named "ALM", was composed of the A5 scFv and the ML3.9 scFv which specifically binds to both HER3 and HER2/neu, respectively. The second bs-scFv antibody molecule, named "ALF", was composed of two distinct scFv molecules, A5 and F4, both with a specificity for HER3. Both bs-scFv antibody molecules were cloned and expressed from E. coli.

Figure 2:
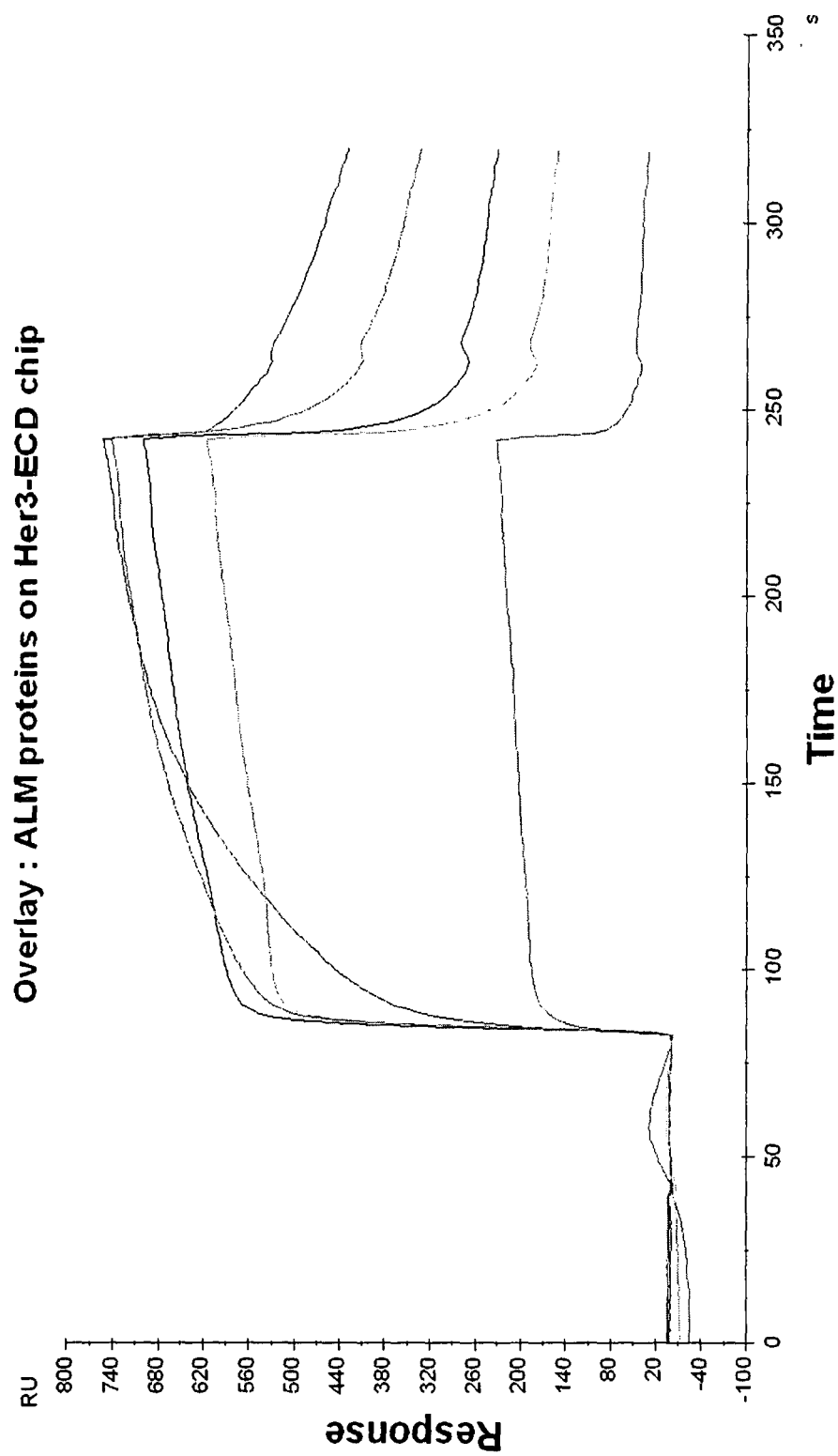
FIG. 2 shows a graph illustrating the binding of ALM proteins to the HER3 extracellular domain on a BIAcore chip.
Figure 3:
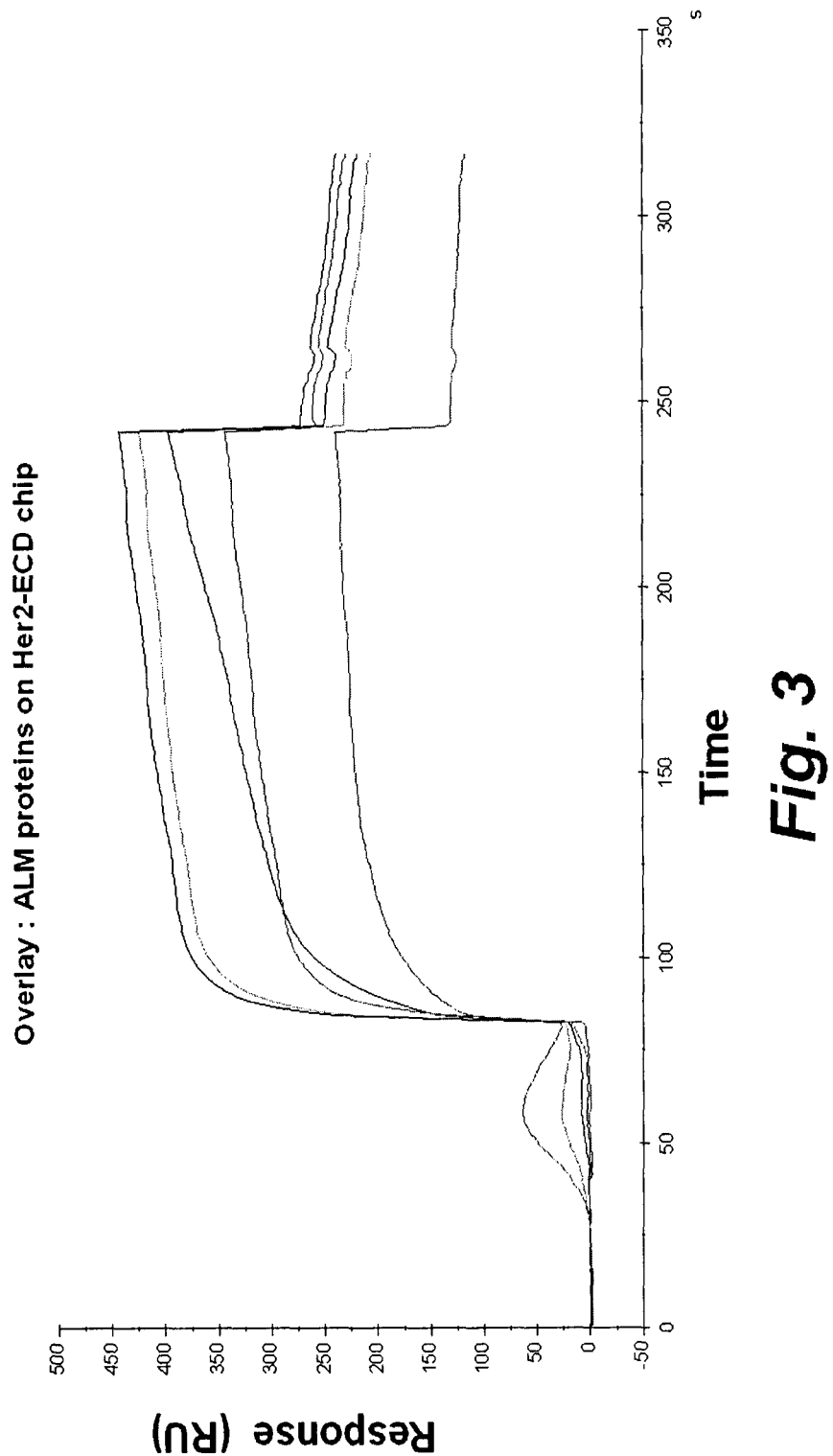
FIG. 3 shows a graph illustrating the binding of ALM proteins to the HER2/neu extracellular domain on a BIAcore chip.
Figure 4:
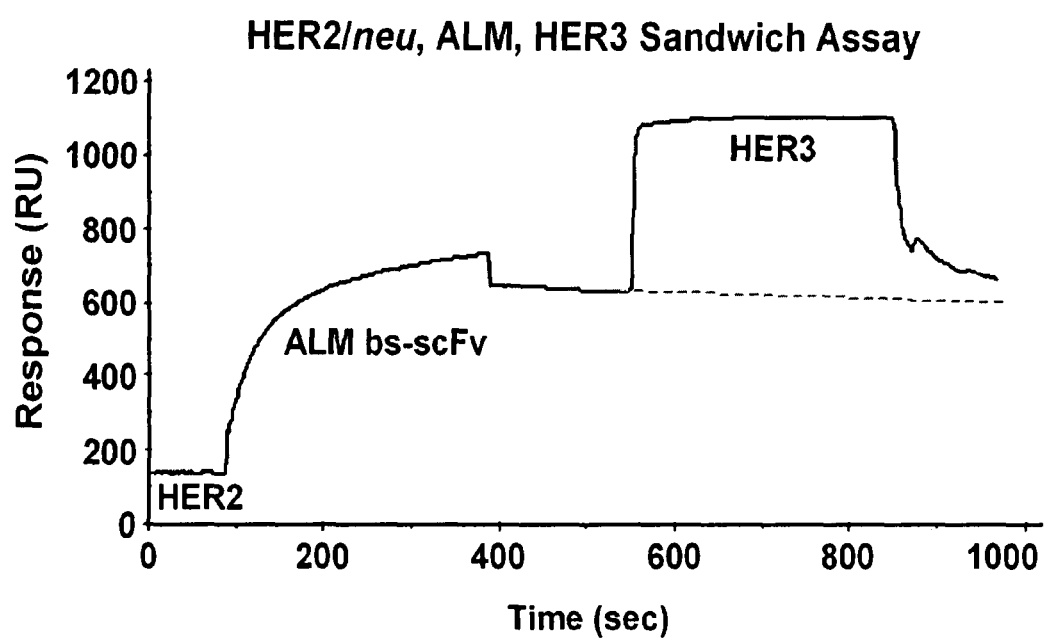
FIG. 4 shows a graph illustrating the simultaneous binding of ALM proteins to HER3 and HER2/neu on a BIAcore chip.
Figure 5A:
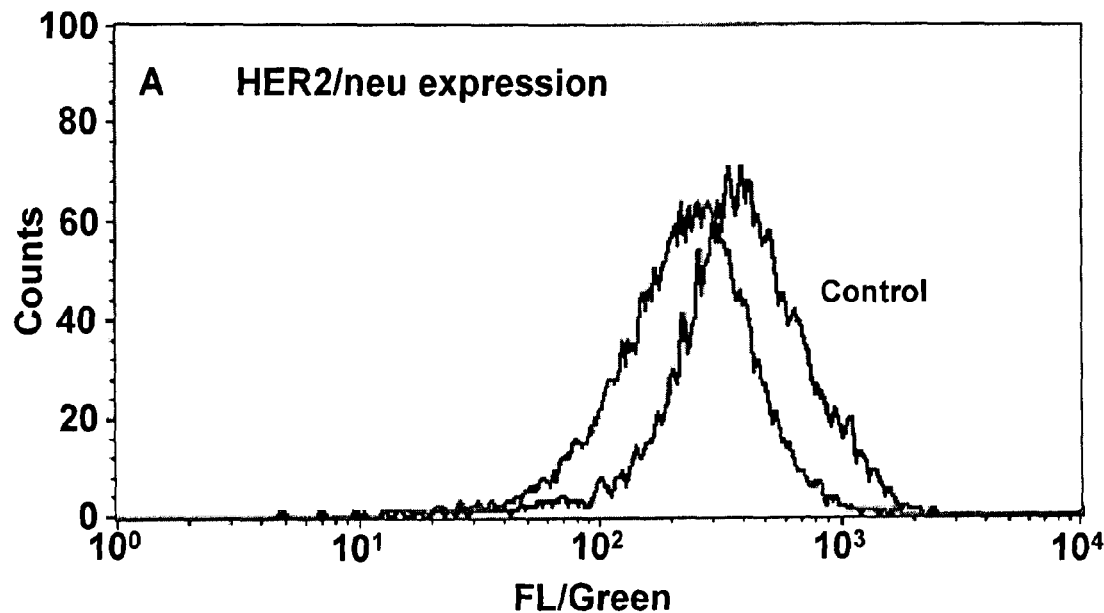
FIGS. 5A and 5B show graphs of flow cytometry results displaying a reduction in cell surface HER2/neu and HER3 following in vitro incubation of ALM with human BT-474 breast cancer cells expressing both HER2/neu and HER3.
Figure 5B:
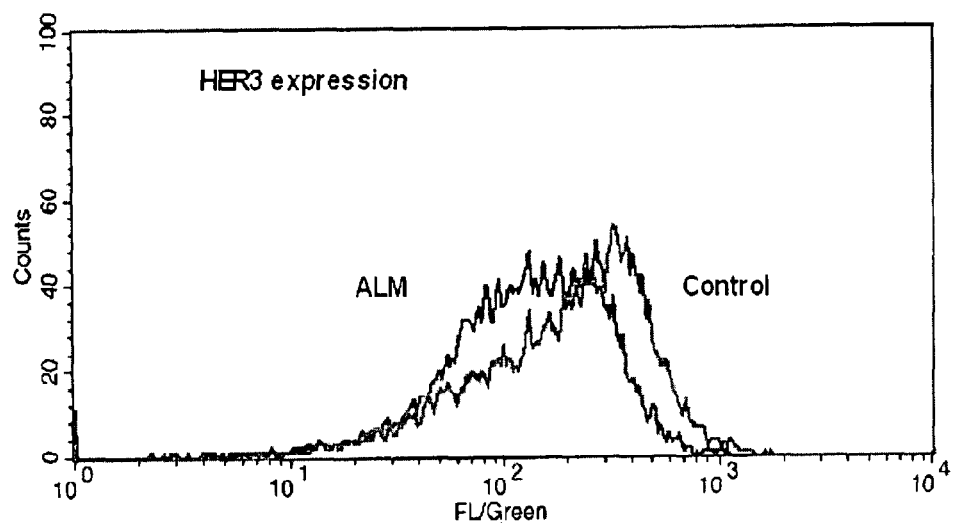
Figure 6:
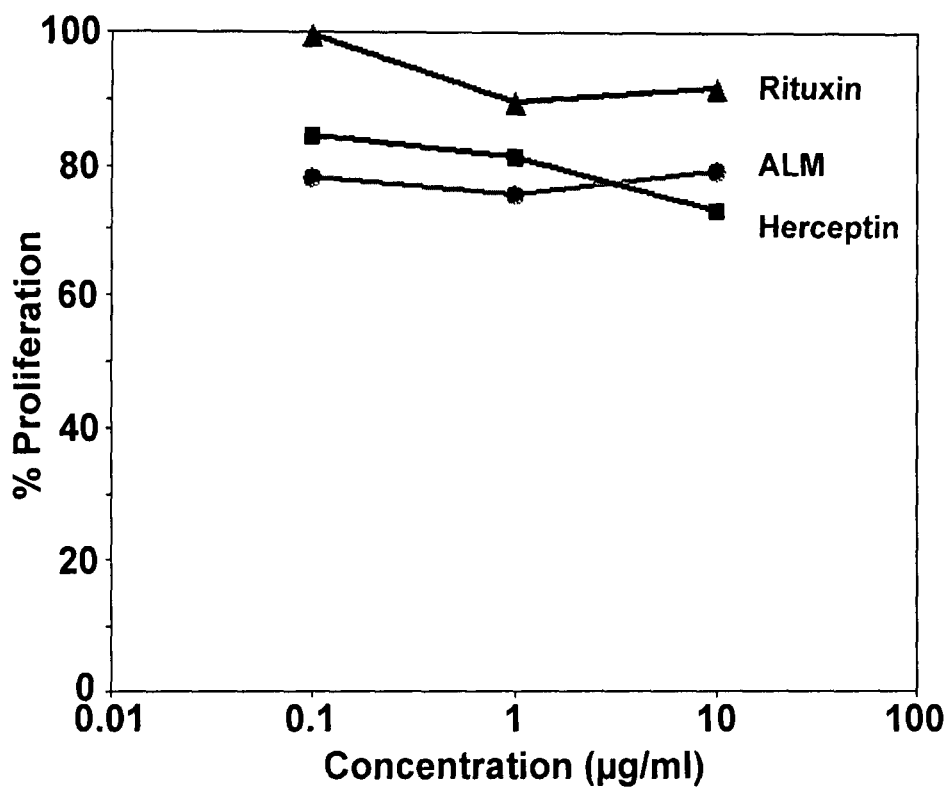
FIG. 6 Shows a graph of the results of an MTT assay demonstrating that ALM diminishes proliferation of BT-474 breast cancer cells expressing both HER2/neu and HER3.
Figure 7:
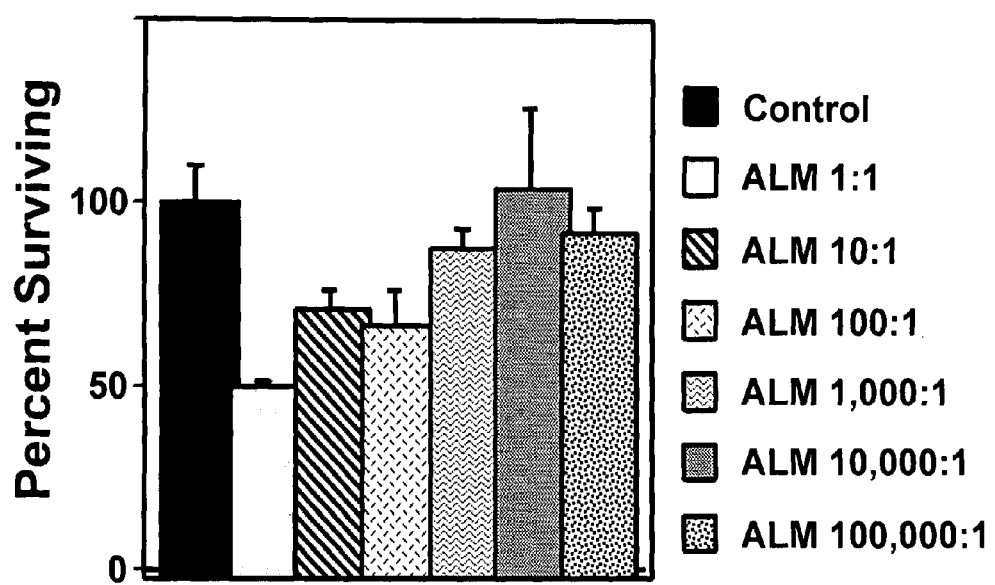
FIG. 7 shows a graph illustrating the results of a 17 day clonogenicity assay demonstrating that incubation of BT-474 cells with ALM at a concentration that is equimolar with cell surface HER2/neu expression leads to a 50% reduction in colony formation (cell survival).
Figure 8:
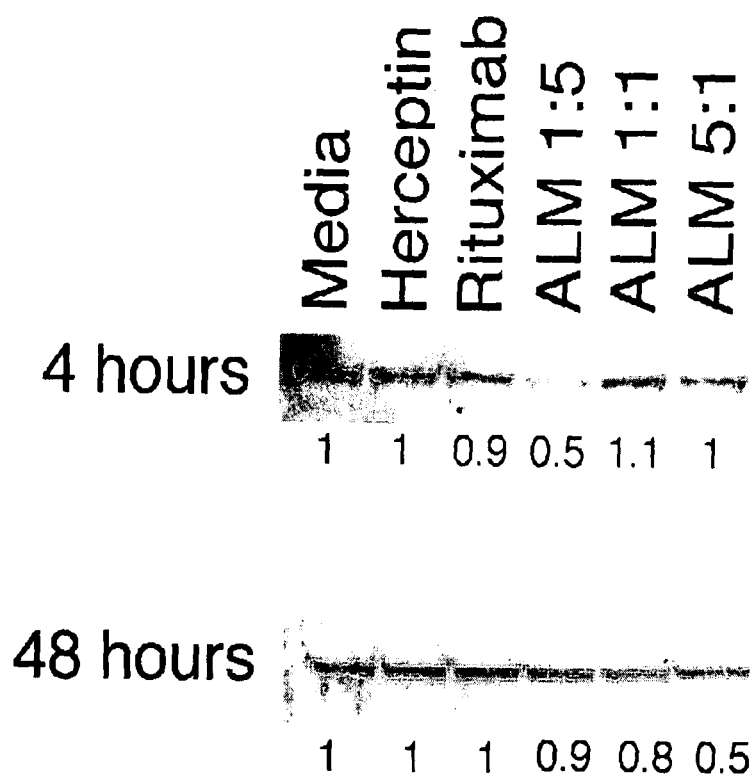
FIG. 8 shows a western blot analysis exhibiting alterations in phosphorylation of AKT over 48 hours following in vitro incubation of different concentrations of ALM with human BT-474 breast cancer cells expressing both HER2/neu and HER3.

ALM was evaluated in a series of in vitro and in vivo assays. Its ability to simultaneously bind to both HER3 and HER2/neu, individually and simultaneously, was demonstrated by surface plasmon resonance on a BIAcore instrument (FIGS. 2, 3 and 4). In vitro, incubation of ALM with human BT-474 breast cancer cells overexpressing both HER3 and HER2/neu lead to reduced cell surface expression of HER2/neu and HER 3 (FIG. 5), decreased proliferation in MTT assays (FIG. 6), reduced survival in a clonogenicity assay (FIG. 7) and increased phosphorylation followed by marked dephosphorylation of AKT2 (FIG. 8), an important protein in the apoptotic pathway. These effects were comparable (MTT assay) or greater (dephosphorylation of AKT2) than those observed using Herceptin[7] (data not shown).

Figure 9:
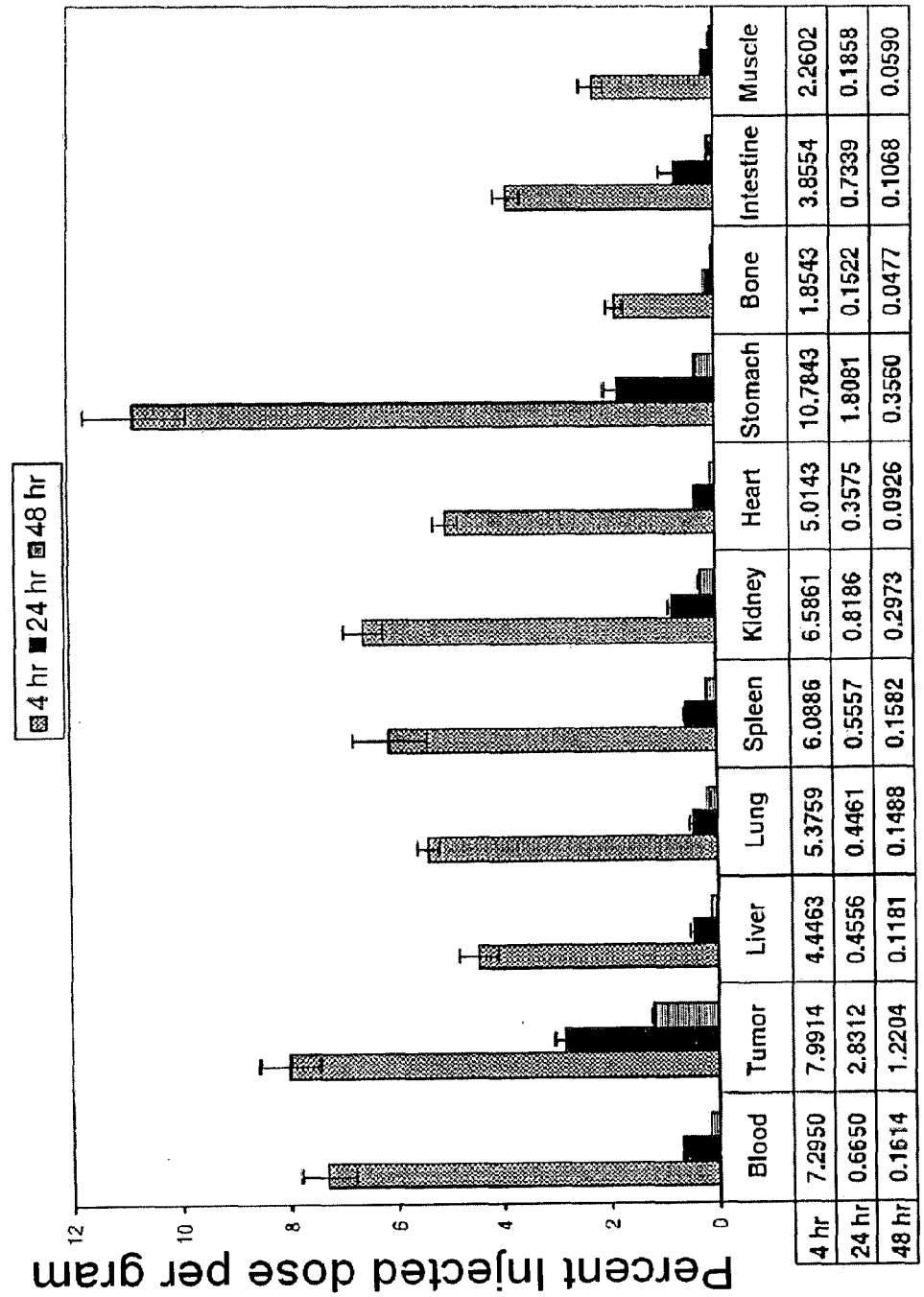
FIG. 9 shows a graph mapping the biodistribution of 1-labeled ALM over 48 hours in immunodeficient mice.

In vivo, radioiodinated ALM exhibited enhanced specific tumor targeting within 24 hours after administration to immunodeficient mice bearing s.c. human BT-474 tumor xenografts (FIG. 9).

These results demonstrate the utility of the bs-scFv antibody molecules of the invention for the treatment of tumor cells that overexpress EGFR proteins. The novel bs-scFv antibody molecules can be used alone or in combination with existing chemotherapeutic methods to treat a variety of cancers including, but not limited to breast, colon, ovarian, endometrial, gastric, pancreatic, prostate and salivary gland cancers.

Example 2

Combined Chemotherapeutic Approaches

HER2/neu is a compelling target for combined chemotherapy approaches as it is overexpressed in a variety of tumors and its overexpression has been correlated with a poor prognosis. While HER2/neu lacks a ligand that can trigger signaling through its tyrosine kinase domain, when overexpressed at high concentrations, HER2/neu can spontaneously form homodimers (Yarden and Sliwkowski (2001) *Nature Reviews, Molecular Cell Biology* 2: 127-137). HER3 is in many ways the opposite of HER2/neu. It actively binds to ligand but lacks a functional tyrosine kinase domain, thus requiring heterodimerization with HER2/neu for signaling. In fact, this combination is believed by many to be the most potent of the signaling complexes formed by the members of the EGFR family (Lohrisch and Piccart (2001) *Sem. Oncology* (28) Suppl 18: 3-11).

Many chemotherapeutic agents lead to damage that in a normal cell will trigger apoptosis. However, some tumor cells have aberrant signaling that interferes with the normal apoptosis signaling pathway. The phosphorylation of AKT2 in HER2/neu overexpressing tumor cells leads to an anti-apoptotic cascade that could interfere with the antitumor effects of chemotherapeutic or biological agents (Zhou et al. (2000) *J. Biol. Chem.*, 275: 8027-8031). Thus, targeting HER2/neu with bs-scFv antibody molecules in combination with existing chemotherapeutic treatments will be more effective in killing the tumor cells than chemotherapy alone.

Example 3

In Vivo Efficacy of $^{211}$At-Labeled Bispecific scFv

Figure 10:
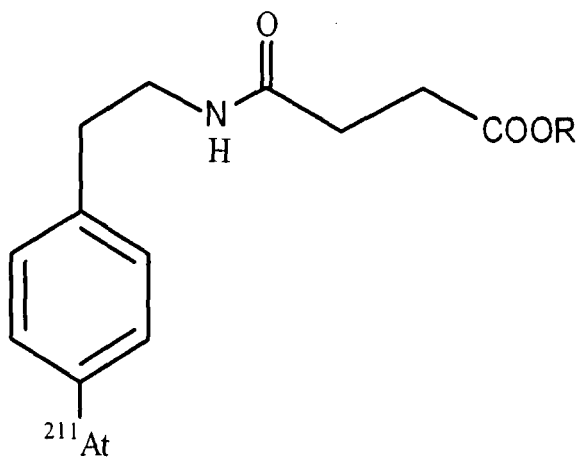
FIG. 10 illustrates a chelate $^{211}$At-SAPS used to label a bispecific antibody according to this invention.

An in vivo study was conducted to evaluate the efficacy of $^{211}$At labeled bispecific scFv against tumors. The bispecific antibody as labeled using $^{211}$At-SAPS chelate (N-(4-[$^{211}$At] astatophenethyl) succinamate) (see, e.g., FIG. 10).

Four days before injection of BT474 breast cancer cells, mice were implanted with a β-estradiol tablet. On day zero, the mice were injected with $5 \times 10^{6 \ BT}474$ breast cancer cells. On day 14, the first therapeutic dose of $^{211}$AT conjugated bispecific antibody (ALM) was administered i.p. at a high dose of 80 µg and at a low dose of 10 µg. Subsequent therapeutic doses were administered on day 16 and on day 18. Tumor volume was then tracked as shown in FIGS. 11A through 11C.

Figure 11A:
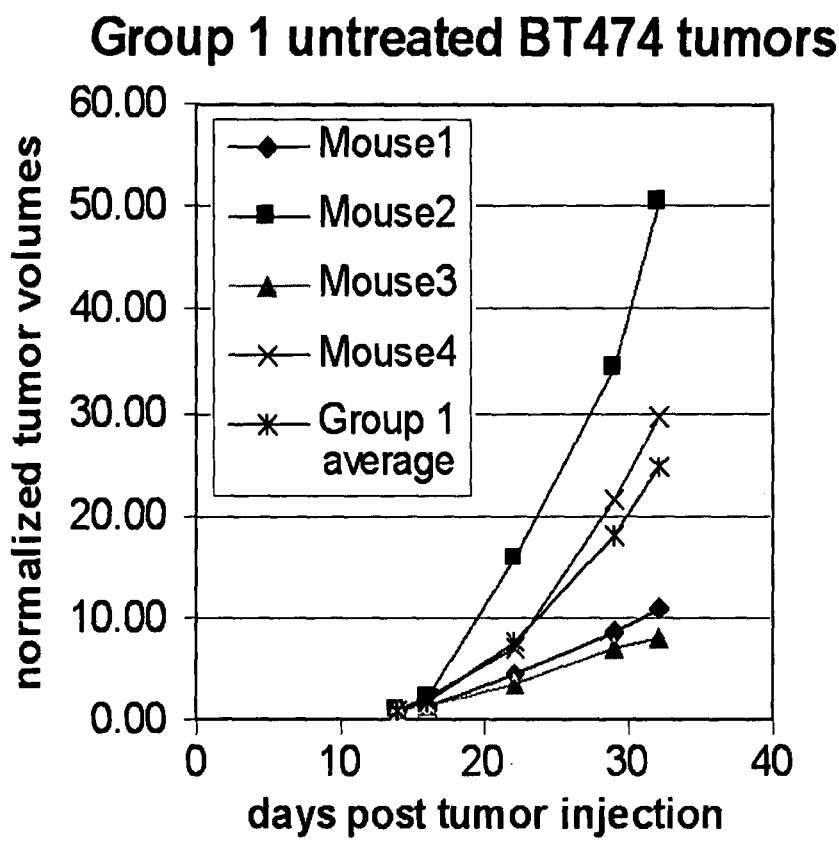
FIGS. 11A through 11C show the effects of $^{211}$At-conjugated ALM at low dosage of 10 μg (FIG. 11C) and at high a dose of 80 μg (FIG. 11B) as compared to untreated controls (FIG. 11A).
Figure 11B:
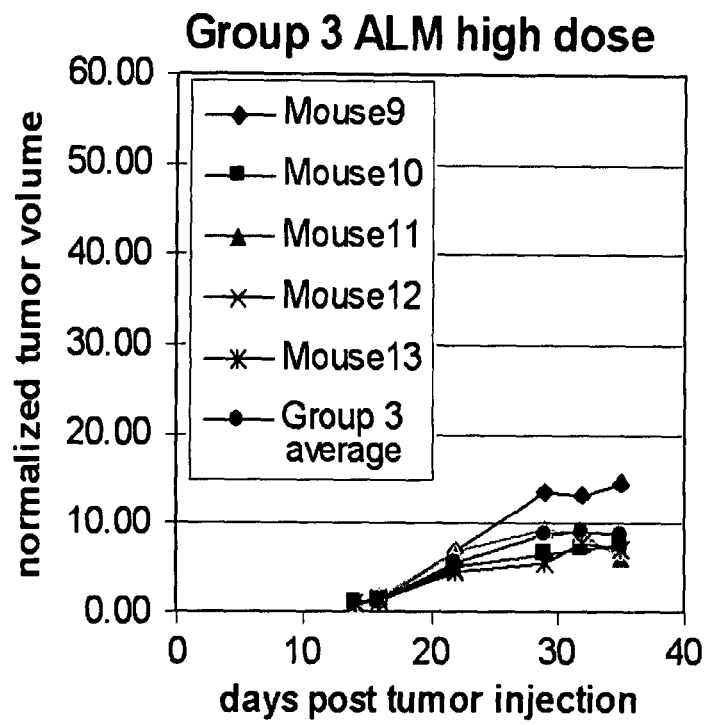
Figure 11C:
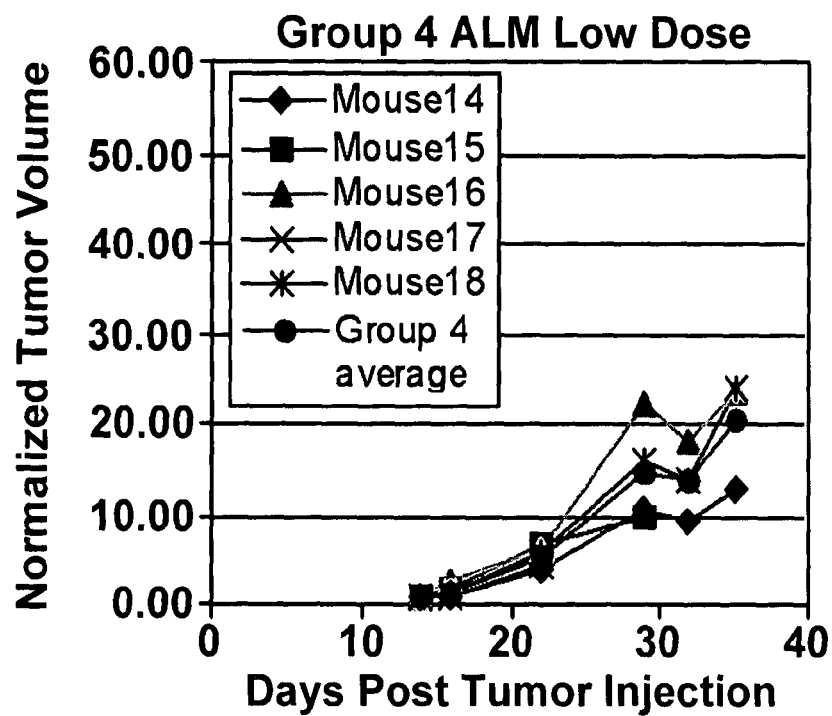

Tumor volume was generally lower in the treated animals (FIGS. 11B and 11C) as compared to the untreated control (FIG. 11A).

Example 4

Cancer Imaging

Figure 12:
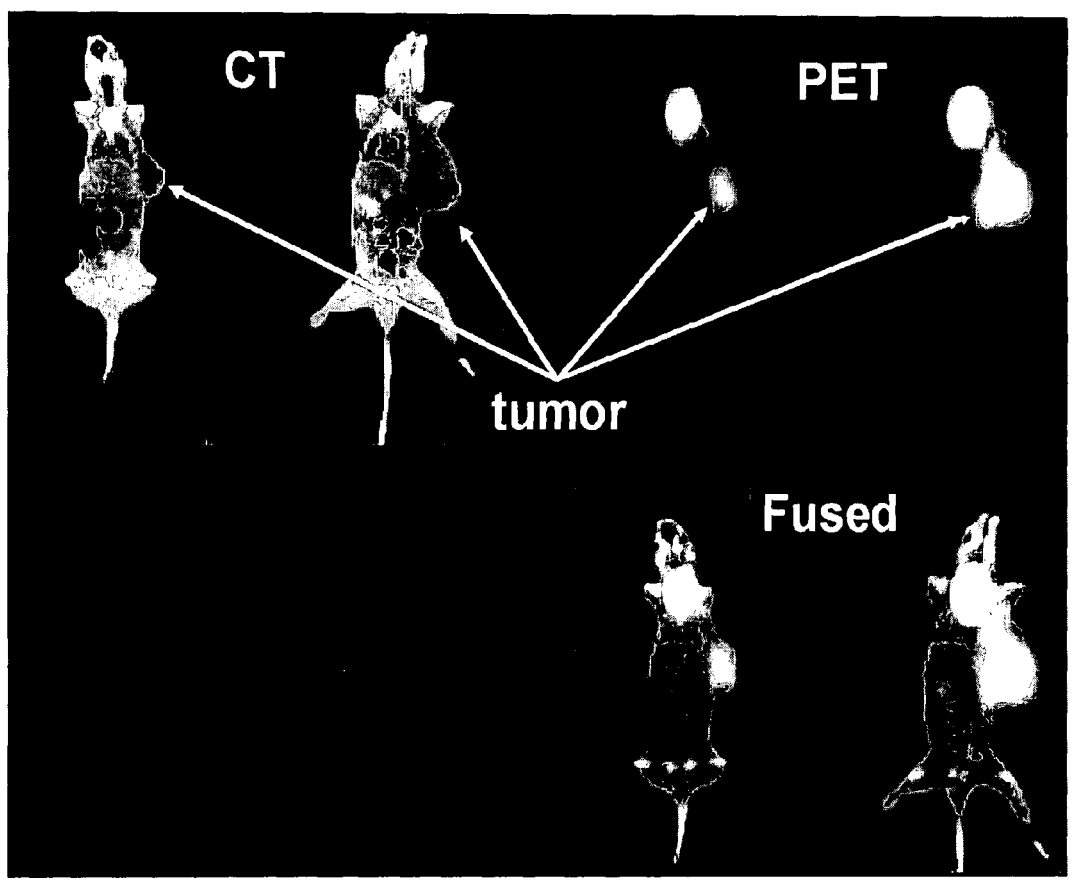
FIG. 12 illustrates specific tumor labeling in a mouse using a $^{124}$I-labeled bispecific antibody (ALM). PET(upper right) and CT (upper left) images of scid mice with SK-OV-3 ovarian carcinoma xenograft expressing HER2/neu and HER3 antigens and imaged 48 hours post-injection on a G.E. Discovery LS at FCCC. The CT slide thickness is 0.63 mm. Image fusion (lower right) performed with MIM software.

FIG. 12 shows a PET-CT image of two mice using Iodine-124 labeled ALM bispecific single-chain Fv. The mice were injected i.v. with 50 microCuries (50 micrograms) of labeled ALM and were imaged 48 hours later.

This should illustrates the efficacy of the bispecific antibodies of this invention for the detection of cancer.

It is understood that the examples and embodiments described herein are for illustrative purposes only and that various modifications or changes in light thereof will be suggested to persons skilled in the art and are to be included within the purview of this application and the scope of the appended claims. All publications, patents, and patent applications cited herein and accompanying appendices are hereby incorporated by reference in their entirety for all purposes.

What is claimed is:

1. An isolated antibody that binds to an EGFR family member, wherein said antibody comprises a heavy chain variable domain (VH) comprising the three VH CDRs of the F5B6H2 antibody and/or a light chain variable domain (VL) comprising the three VL CDRs of the F5B6H2 antibody.

2. The antibody of claim 1, wherein said antibody comprises a heavy chain variable domain (VH) of the F5B6H2 antibody and/or a light chain variable domain (VL) of the F5B6H2 antibody.

3. The antibody of claim 1, wherein said antibody comprises a heavy chain variable domain (VH) comprising the three VH CDRs of the F5B6H2 antibody and a light chain variable domain (VL) comprising the three VL CDRs of the F5B6H2 antibody.

4. The antibody of claim 1, wherein said antibody comprises a heavy chain variable domain (VH) of the F5B6H2 antibody and a light chain variable domain (VL) of the F5B6H2 antibody.

5. The antibody of claim 1, wherein said antibody is an antibody selected from the group consisting of an scFv, an IgG, a Fab, an (Fab')$_2$, and an (scFv')$_2$.

6. The antibody of claim 1, wherein said antibody is coupled to an effector.

7. The antibody claim 6, wherein said effector comprises a second antibody.

8. The antibody of claim 6, wherein said effector comprises a second antibody, wherein said second antibody comprises a heavy chain variable domain (VH) comprising the three VH CDRs and/or a light chain variable domain (VL) comprising the three VL CDRs of an antibody selected from the group consisting of A5, F5B6H2, C6.5, C6-B1D2, C6 MH3-B1, C6ML3-9, EGFR.B11, EGFR.C10, EGFR.1C10, EGFR.E12, EGFR.E8, F5, HER3.B12, HER3.E12, HER3.F4, HER3.H1, HER3.H3, HER4.B6, HER4.E3, and G98A.

9. The antibody of claim 8, wherein said second antibody comprises a heavy chain variable domain (VH) comprising the three VH CDRs and a light chain variable domain (VL) comprising the three VL CDRs of an antibody selected from the group consisting of A5, F5B6H2, C6.5, C6-B1D2, C6 MH3-B1, C6ML3-9, EGFR.B11, EGFR.C10, EGFR.1C10, EGFR.E12, EGFR.E8, F5, HER3.B12, HER3.E12, HER3.F4, HER3.H1, HER3.H3, HER4.B6, HER4.E3, and G98A.

10. The antibody of claim 8, wherein said second antibody comprises a heavy chain variable domain (VH) and/or a light chain variable domain (VL) of an antibody selected from the group consisting of A5, F5B6H2, C6.5, C6-B1D2, C6 MH3-B1, C6ML3-9, EGFR.B11, EGFR.C10, EGFR.1C10, EGFR.E12, EGFR.E8, F5, HER3.B12, HER3.E12, HER3.F4, HER3.H1, HER3.H3, HER4.B6, HER4.E3, and G98A.

11. The antibody of claim 8, wherein said second antibody comprises a heavy chain variable domain (VH) and a light chain variable domain (VL) of an antibody selected from the group consisting of A5, F5B6H2, C6.5, C6-B1D2, C6 MH3-B1, C6ML3-9, EGFR.B11, EGFR.C10, EGFR.1C10, EGFR.E12, EGFR.E8, F5, HER3.B12, HER3.E12, HER3.F4, HER3.H1, HER3.H3, HER4.B6, HER4.E3, and G98A.

12. The antibody of claim 8, wherein said second antibody is joined to the first antibody by a linker.

13. The antibody of claim 12, wherein said linker is a peptide linker.

14. The antibody of claim 12, wherein said linker is a peptide linker that lacks a proteolytic cleavage site.

15. The antibody of claim 1, wherein said antibody is combined with a pharmaceutically acceptable excipient.

16. An isolated nucleic acid that encodes an isolated antibody that binds to an EGFR family member, wherein said antibody comprises a heavy chain variable domain (VH) comprising the three VH CDRs of the F5B6H2 antibody and/or a light chain variable domain (VL) comprising the three VL CDRs of the F5B6H2 antibody.

17. A vector comprising the nucleic acid sequence of claim 16.

18. A host cell transfected with a nucleic acid that encodes an antibody comprising a heavy chain variable domain (VH) comprising the three VH CDRs of the F5B6H2 antibody and/or a light chain variable domain (VL) comprising the three VL CDRs of the F5B6H2 antibody.

* * * * *